United States Patent
Zhang et al.

(10) Patent No.: US 11,426,206 B2
(45) Date of Patent: *Aug. 30, 2022

(54) PEDICLE SCREW HAVING A REMOVABLE ROD COUPLING

(71) Applicant: GLOBUS MEDICAL, INC., Audubon, PA (US)

(72) Inventors: Hong Zhang, Plano, TX (US); Dan Sucato, Dallas, TX (US)

(73) Assignee: Globus Medical, Inc., Audubon, PA (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/562,739

(22) Filed: Sep. 6, 2019

(65) Prior Publication Data
US 2020/0015859 A1    Jan. 16, 2020

Related U.S. Application Data

(63) Continuation of application No. 15/350,163, filed on Nov. 14, 2016, now Pat. No. 10,433,876, which is a
(Continued)

(51) Int. Cl.
*A61B 17/70* (2006.01)
*A61B 17/88* (2006.01)
(Continued)

(52) U.S. Cl.
CPC ...... *A61B 17/7034* (2013.01); *A61B 17/7001* (2013.01); *A61B 17/705* (2013.01);
(Continued)

(58) Field of Classification Search
CPC .............. A61B 17/7032; A61B 17/705; A61B 17/7052; A61B 17/7034; A61B 17/7074;
(Continued)

(56) References Cited

U.S. PATENT DOCUMENTS

| 4,653,489 A | 3/1987 | Tronzo |
|---|---|---|
| 4,743,260 A | 5/1988 | Burton |

(Continued)

FOREIGN PATENT DOCUMENTS

| JP | 2003250822 A | 9/2003 |
|---|---|---|
| WO | 2008128105 A1 | 10/2008 |

(Continued)

OTHER PUBLICATIONS

Bradford, D.S., et al., "One-stage anterior and posterior hemivertebral resection and arthrodesis for congenital scoliosis". JBJS (1990), 72-A:536-40.
(Continued)

*Primary Examiner* — Lynnsy M Summitt

(57) ABSTRACT

A pedicle screw for spinal fixation having a bone fastener portion a permanent rod coupling, a breakaway portion connected to the permanent rod coupling and a temporary rod coupling. A permanent rod can be positioned in the permanent rod coupling and a temporary rod can be positioned in the temporary rod coupling and when the temporary rod is not needed the temporary rod coupling can be removed by separation at a breakaway portion.

17 Claims, 48 Drawing Sheets

(2) Final Rod Insertion

Related U.S. Application Data continuation of application No. 15/017,023, filed on Feb. 5, 2016, now Pat. No. 9,526,527, which is a continuation of application No. 13/672,150, filed on Nov. 8, 2012, now Pat. No. 9,345,517, which is a continuation-in-part of application No. 13/410,035, filed on Mar. 1, 2012, now Pat. No. 9,579,126, which is a continuation-in-part of application No. 12/364,412, filed on Feb. 2, 2009, now Pat. No. 9,408,641.

(60) Provisional application No. 61/025,761, filed on Feb. 2, 2008, provisional application No. 61/080,162, filed on Jul. 11, 2008.

(51) Int. Cl.
  *A61B 90/00* (2016.01)
  *A61B 17/56* (2006.01)
  *A61B 17/68* (2006.01)

(52) U.S. Cl.
  CPC ...... *A61B 17/7023* (2013.01); *A61B 17/7032* (2013.01); *A61B 17/7052* (2013.01); *A61B 17/7079* (2013.01); *A61B 17/7086* (2013.01); *A61B 17/8863* (2013.01); *A61B 17/701* (2013.01); *A61B 17/7011* (2013.01); *A61B 2017/564* (2013.01); *A61B 2017/565* (2013.01); *A61B 2017/567* (2013.01); *A61B 2017/681* (2013.01); *A61B 2090/037* (2016.02)

(58) Field of Classification Search
  CPC ............ A61B 17/7083; A61B 17/7077; A61B 17/7079; A61B 17/7082; A61B 17/7088
  See application file for complete search history.

(56) References Cited

U.S. PATENT DOCUMENTS

| | | |
|---|---|---|
| 4,772,261 A | 9/1988 | Von Hoff et al. |
| 4,946,458 A | 8/1990 | Harms et al. |
| 5,005,562 A | 4/1991 | Cotrel |
| 5,047,030 A | 9/1991 | Draenert |
| 5,067,955 A | 11/1991 | Cotrel |
| 5,102,412 A * | 4/1992 | Rogozinski ........ A61B 17/7082 606/250 |
| 5,129,349 A | 7/1992 | Glen |
| 5,133,717 A * | 7/1992 | Chopin ............. A61B 17/7055 606/264 |
| 5,176,680 A * | 1/1993 | Vignaud ............ A61B 17/704 606/302 |
| 5,219,349 A | 6/1993 | Krag et al. |
| 5,329,933 A | 7/1994 | Graf |
| 5,385,565 A | 1/1995 | Ray |
| 5,397,363 A | 3/1995 | Gelbard |
| 5,593,407 A | 1/1997 | Reis |
| 5,620,443 A | 4/1997 | Gertzbein et al. |
| 5,630,816 A | 5/1997 | Kambin |
| 5,702,395 A | 12/1997 | Hopf |
| 5,707,372 A | 1/1998 | Errico et al. |
| 5,728,097 A | 3/1998 | Mathews |
| 5,800,407 A | 9/1998 | Eldor |
| 5,871,484 A | 2/1999 | Spievack et al. |
| 5,876,403 A | 3/1999 | Shitoto |
| 5,941,877 A | 8/1999 | Viegas et al. |
| 5,993,449 A | 11/1999 | Schlapfer et al. |
| 6,077,263 A * | 6/2000 | Ameil ................ A61B 17/7032 606/276 |
| 6,090,113 A | 7/2000 | Le Couedic et al. |
| 6,136,002 A | 10/2000 | Shih et al. |
| 6,214,012 B1 | 4/2001 | Karpman et al. |
| 6,248,106 B1 | 6/2001 | Ferree |
| 6,287,309 B1 | 9/2001 | Baccelli et al. |
| 6,331,179 B1 | 12/2001 | Freid |
| 6,423,062 B2 | 7/2002 | Enayati |
| 6,454,769 B2 | 9/2002 | Wagner et al. |
| 6,461,359 B1 | 10/2002 | Tribus et al. |
| 6,488,681 B2 | 12/2002 | Martin et al. |
| 6,517,542 B1 | 2/2003 | Papay et al. |
| 6,554,830 B1 | 4/2003 | Chappius |
| 6,554,834 B1 | 4/2003 | Crozet et al. |
| 6,558,390 B2 | 5/2003 | Cragg |
| 6,565,572 B2 | 5/2003 | Chappius |
| 6,569,164 B1 | 5/2003 | Assaker et al. |
| 6,582,439 B1 | 6/2003 | Sproul |
| 6,610,063 B2 | 8/2003 | Kumar et al. |
| 6,620,195 B2 | 9/2003 | Goble et al. |
| 6,623,485 B2 | 9/2003 | Doubler et al. |
| 6,645,208 B2 | 11/2003 | Apfelbaum et al. |
| 6,663,637 B2 | 12/2003 | Dixon et al. |
| 6,730,095 B2 | 5/2004 | Olson et al. |
| 6,740,086 B2 | 5/2004 | Richelsoph |
| 6,740,090 B1 | 5/2004 | Cragg et al. |
| 6,749,613 B1 | 6/2004 | Conchy et al. |
| 6,755,835 B2 | 6/2004 | Schultheiss et al. |
| 6,780,191 B2 | 8/2004 | Sproul |
| 6,858,030 B2 | 2/2005 | Martin et al. |
| 6,881,215 B2 | 4/2005 | Assaker et al. |
| 6,899,714 B2 | 5/2005 | Vaughan |
| 6,942,698 B1 | 9/2005 | Jackson |
| 6,945,975 B2 | 9/2005 | Dalton |
| 6,964,665 B2 | 11/2005 | Thomas et al. |
| 6,974,460 B2 | 12/2005 | Carbone et al. |
| 6,976,988 B2 | 12/2005 | Ralph et al. |
| 6,981,973 B2 | 1/2006 | McKinley |
| 7,008,433 B2 | 3/2006 | Voellmicke et al. |
| 7,033,392 B2 | 4/2006 | Schmiel et al. |
| 7,041,138 B2 | 5/2006 | Lange |
| 7,118,573 B2 | 10/2006 | Michelson |
| 7,163,539 B2 | 1/2007 | Abdelgany et al. |
| 7,220,262 B1 | 5/2007 | Hynes |
| 7,273,481 B2 | 9/2007 | Lombardo et al. |
| 7,621,914 B2 | 11/2009 | Ralph |
| 7,655,008 B2 * | 2/2010 | Lenke ................ A61B 17/7077 606/60 |
| 7,658,753 B2 | 2/2010 | Carl et al. |
| 7,695,473 B2 | 4/2010 | Ralph et al. |
| 7,766,911 B1 | 8/2010 | Navarro et al. |
| 7,776,072 B2 | 8/2010 | Barry |
| 7,789,897 B2 | 9/2010 | Sanders |
| 7,794,464 B2 * | 9/2010 | Bridwell ............ A61B 17/7032 606/86 A |
| 7,867,255 B2 * | 1/2011 | Miller .................. A61B 17/705 606/250 |
| 7,976,567 B2 * | 7/2011 | Null ..................... A61B 17/705 606/250 |
| 8,007,522 B2 | 8/2011 | Hutchinson |
| 8,083,773 B2 | 12/2011 | Durrani |
| 8,100,955 B2 | 1/2012 | Blain et al. |
| 8,152,838 B2 | 4/2012 | Ensign et al. |
| 8,216,312 B2 | 7/2012 | Gray |
| 8,246,665 B2 * | 8/2012 | Butler .................. A61B 17/705 606/308 |
| 8,277,453 B2 | 10/2012 | Kave et al. |
| 8,388,659 B1 * | 3/2013 | Lab ..................... A61B 17/7037 606/265 |
| 8,657,857 B2 * | 2/2014 | Dall ..................... A61B 17/7035 606/268 |
| 8,663,289 B2 * | 3/2014 | Schwab ............. A61B 17/7037 606/267 |
| 8,728,128 B2 | 5/2014 | Hawkes |
| 8,821,552 B2 | 9/2014 | Reitzig et al. |
| 8,882,803 B2 * | 11/2014 | Iott et al. ............. A61B 17/705 606/246 |
| 8,998,963 B2 | 4/2015 | Ziolo |
| 9,179,957 B2 * | 11/2015 | Ibrahim ............. A61B 17/7091 |
| 9,439,679 B2 * | 9/2016 | Dall ..................... A61B 17/702 |
| 9,615,867 B2 * | 4/2017 | Picetti ................ A61B 17/8605 |
| 10,405,893 B2 * | 9/2019 | Laeng ................ A61B 17/7002 |
| 10,603,077 B2 * | 3/2020 | Zhang ................ A61B 17/7001 |
| 2002/0007183 A1 | 1/2002 | Lee et al. |
| 2002/0013585 A1 * | 1/2002 | Gournay ............ A61B 17/7034 606/272 |

(56) References Cited

U.S. PATENT DOCUMENTS

| | | |
|---|---|---|
| 2002/0095153 A1 | 7/2002 | Jones et al. |
| 2003/0065329 A1 | 4/2003 | Vaughan |
| 2003/0144664 A1 | 7/2003 | Cavagna et al. |
| 2004/0111088 A1 | 6/2004 | Picetti et al. |
| 2004/0158247 A1 | 8/2004 | Sitiso et al. |
| 2005/0203511 A1 | 9/2005 | Ison-MacDonald et al. |
| 2005/0234449 A1 | 10/2005 | Aferzon |
| 2005/0240198 A1 | 10/2005 | Albertson et al. |
| 2005/0277934 A1 | 12/2005 | Vardiman |
| 2006/0036246 A1 | 2/2006 | Carl et al. |
| 2006/0249623 A1 | 2/2006 | Anderson et al. |
| 2006/0173456 A1 | 8/2006 | Hawkes et al. |
| 2006/0195092 A1 | 8/2006 | Barry |
| 2006/0293659 A1 | 12/2006 | Alvarez |
| 2007/0093824 A1* | 4/2007 | Hestad ............... A61B 17/7032 606/261 |
| 2007/0191840 A1* | 8/2007 | Pond ................. A61B 17/7091 623/17.16 |
| 2007/0213715 A1 | 9/2007 | Bridwell et al. |
| 2007/0213716 A1 | 9/2007 | Lenke |
| 2007/0225713 A1 | 9/2007 | Altarac et al. |
| 2007/0233062 A1 | 10/2007 | Berry |
| 2007/0233079 A1* | 10/2007 | Fallin ................. A61B 17/8863 606/86 A |
| 2007/0233089 A1* | 10/2007 | DiPoto ............... A61B 17/7037 606/279 |
| 2007/0270805 A1 | 11/2007 | Miller et al. |
| 2007/0270810 A1 | 11/2007 | Sanders |
| 2007/0270817 A1* | 11/2007 | Rezach ................ A61B 17/705 606/252 |
| 2007/0286366 A1 | 12/2007 | Deboy et al. |
| 2008/0027436 A1 | 1/2008 | Cournoyer et al. |
| 2008/0058805 A1* | 3/2008 | Stuart ................ A61B 17/7007 606/914 |
| 2008/0177323 A1 | 7/2008 | Null et al. |
| 2008/0177330 A1 | 7/2008 | Ralph |
| 2008/0215097 A1 | 9/2008 | Ensign et al. |
| 2008/0255617 A1* | 10/2008 | Cho .................. A61B 17/7031 606/246 |
| 2009/0099605 A1 | 4/2009 | Fallin et al. |
| 2009/0131982 A1* | 5/2009 | Schwab ............. A61B 17/7001 606/246 |
| 2009/0198273 A1 | 8/2009 | Zhang et al. |
| 2009/0198279 A1* | 8/2009 | Zhang ................ A61B 17/705 606/264 |
| 2009/0259254 A1* | 10/2009 | Pisharodi ........... A61B 17/7034 606/246 |
| 2009/0326586 A1 | 12/2009 | Duarte |
| 2010/0042149 A1 | 2/2010 | Chao et al. |
| 2010/0076494 A1 | 3/2010 | Markworth |
| 2010/0234892 A1* | 9/2010 | Mazda ................ A61B 17/705 606/276 |
| 2010/0247600 A1 | 9/2010 | Xia et al. |
| 2010/0249843 A1 | 9/2010 | Wegrzyn, III |
| 2010/0256683 A1 | 10/2010 | Iott et al. |
| 2011/0137358 A1 | 6/2011 | Manninen |
| 2012/0221053 A1* | 8/2012 | Copt ................. A61B 17/7035 606/251 |
| 2012/0221057 A1 | 8/2012 | Zhang et al. |
| 2013/0090691 A1 | 4/2013 | Zhang et al. |

FOREIGN PATENT DOCUMENTS

| | | |
|---|---|---|
| WO | 2009097623 A2 | 8/2009 |
| WO | 2009097624 A2 | 8/2009 |

OTHER PUBLICATIONS

Compere, E.L., et al., "Excision of hemivertebrae for correction of congenital scoliosis: report of two cases". JBJS (1932), 14-A:555-62.

Deviten, V. et al., "Excision of hemivertebrae in the management of congenital scoliosis involving the thoracic and thoracolumbar spine". JBJS (2001), 83-B:496-500.

Floman, Y., et al. "Osteotomy of the fusion mass in scoliosis". JBJS (1982), 64-A:1307-16.

Leatherman, K.D., et al. "Two-stage corrective surgery for congenital deformities of the spine". JBJS (1979), 61-B:324-8.

Suk, S., et al. "Posterior vertebral column resection for severe spinal deformities." Spine (2002), 27:2374-82.

Suk, S., et al. "Posterior vertebral column resection for severe rigid scoliosis". Spine (2005), 30:1682-87.

Suk, S., et al. "Posterior vertebral column resection in fixed lumbosacral deformity". Spine (2005), 30:E703-10.

Tokunaga, M., et al. "Vertebral decancellation for severe scoliosis". Spine (2000), 25:469-74.

Wiles, P., "Resection of dorsalvertebrae in congenital scoliosis". JBJS (1951), 33-A:151-4.

Berguiristain, J.L., et al. "Experimental Scoliosis by Epiphysiodesis in Pigs". International Orthopaedics (1980), 3:317-321.

* cited by examiner (1) Temporary Rod Insertion (3) Temporary Rod Removal (2) Final Rod Insertion

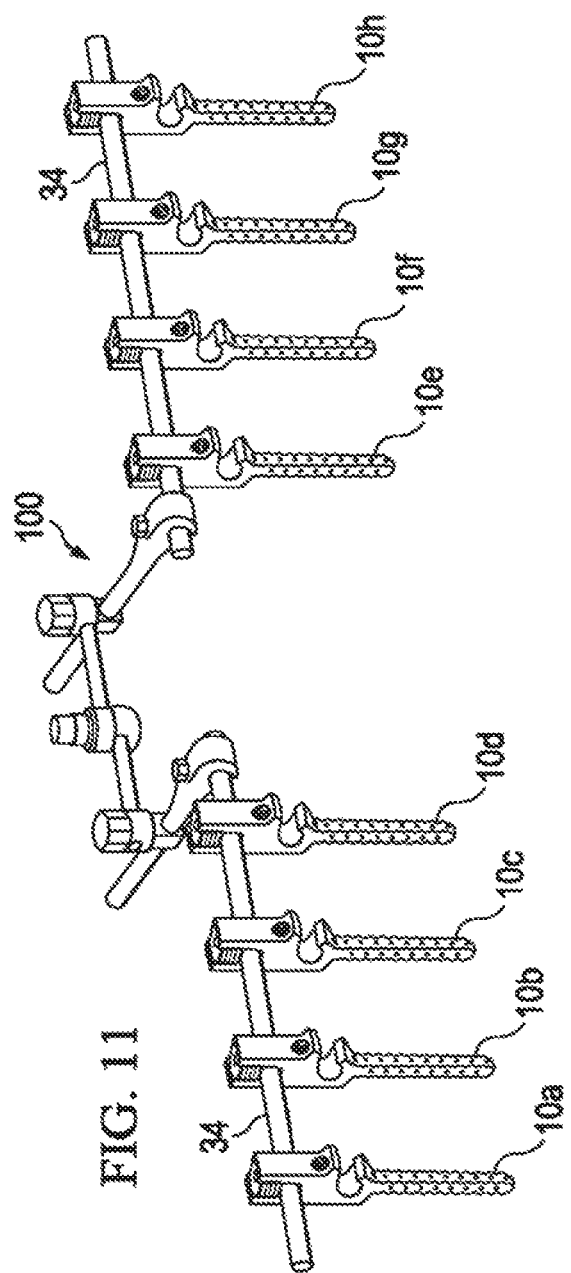
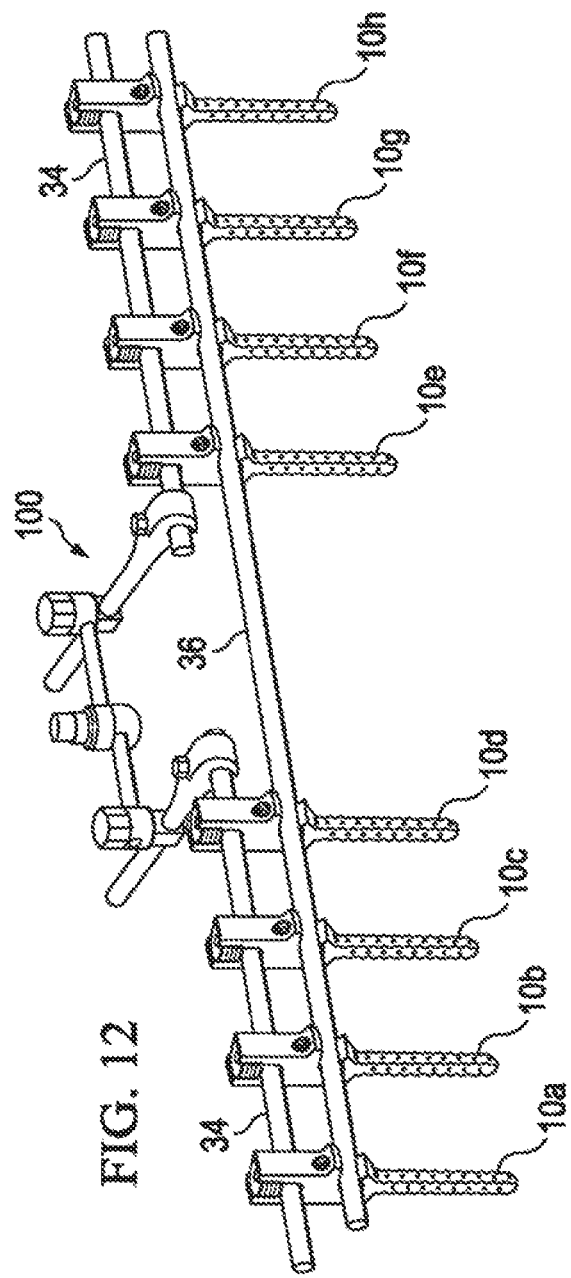

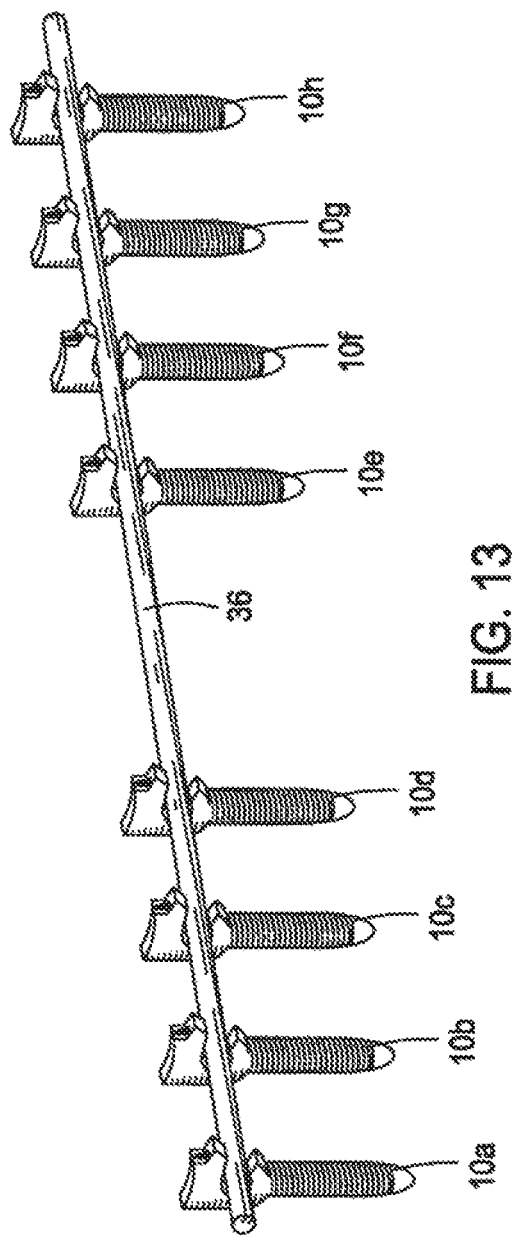

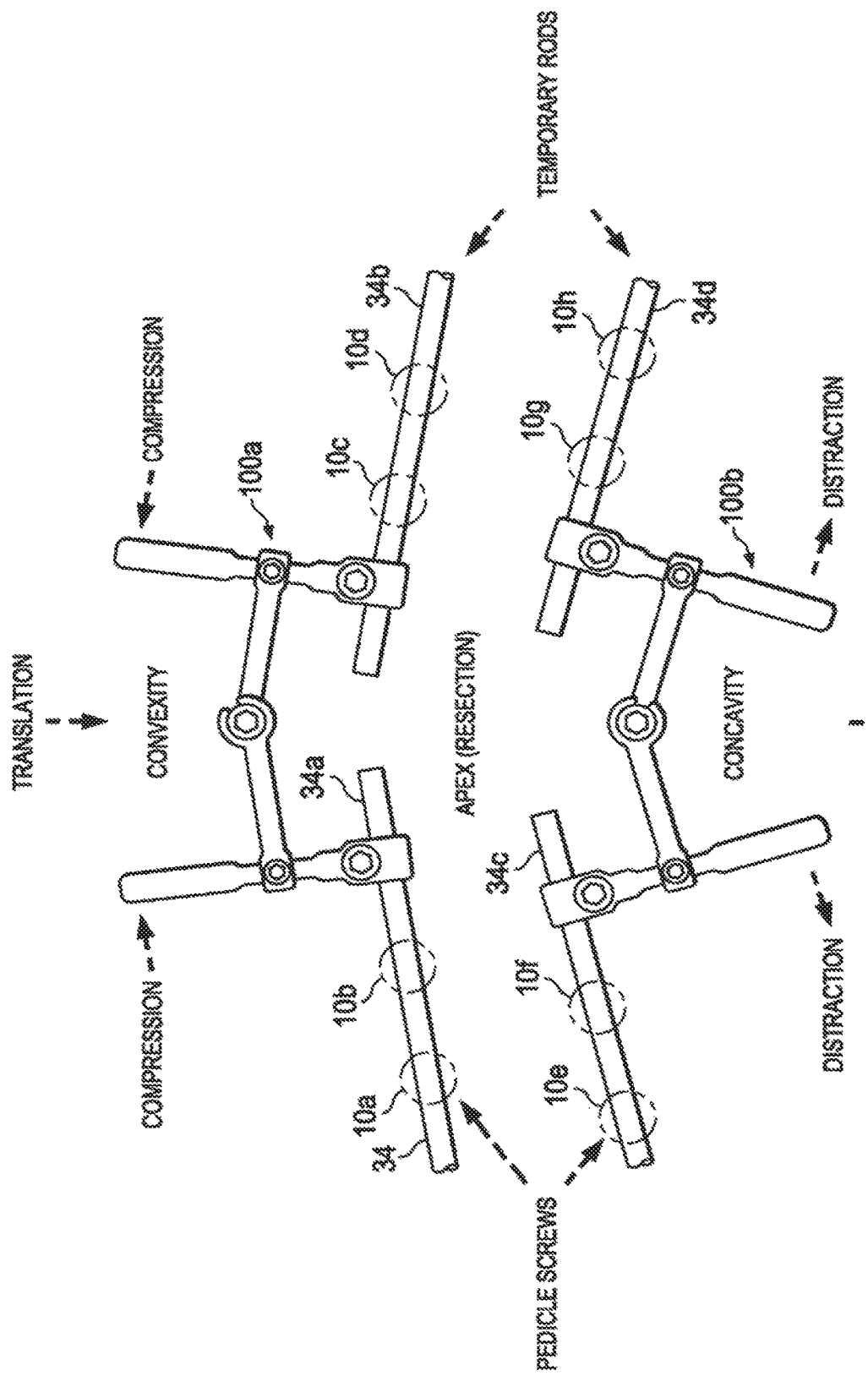

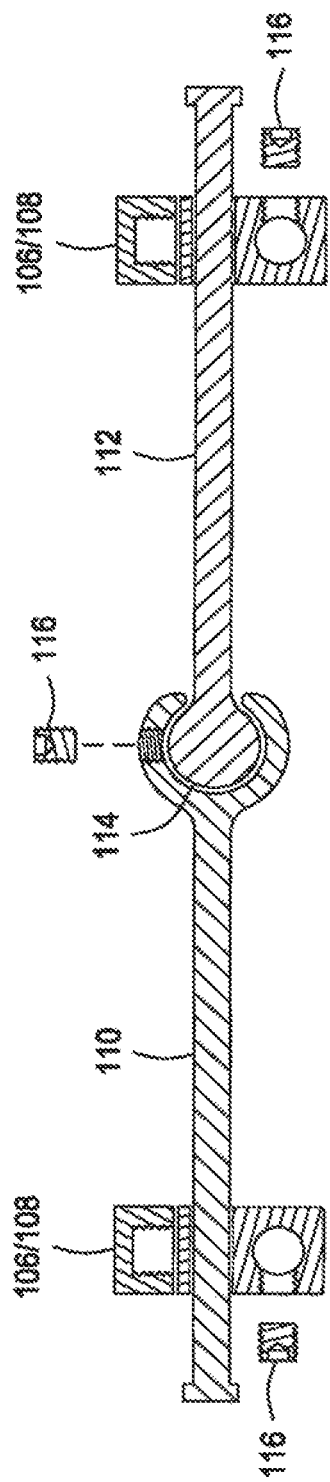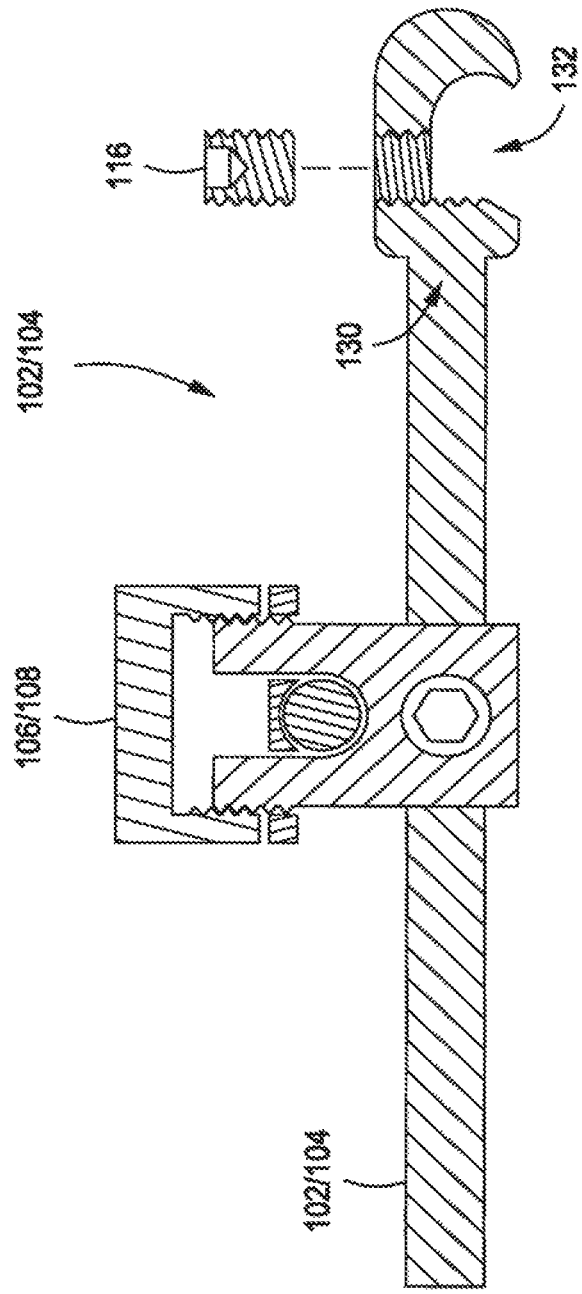

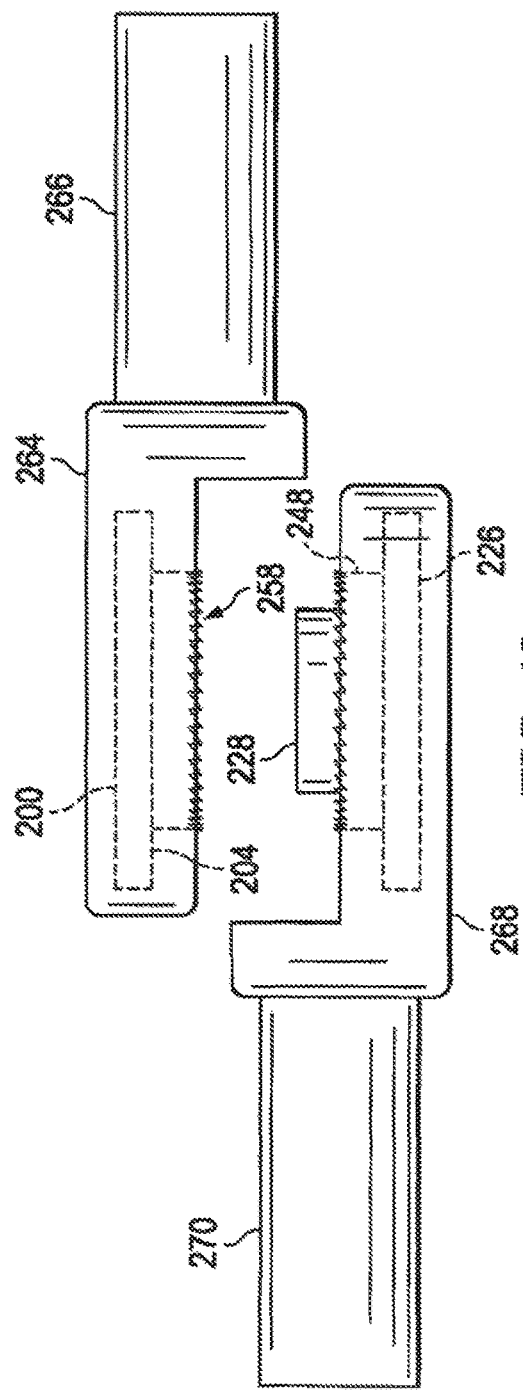
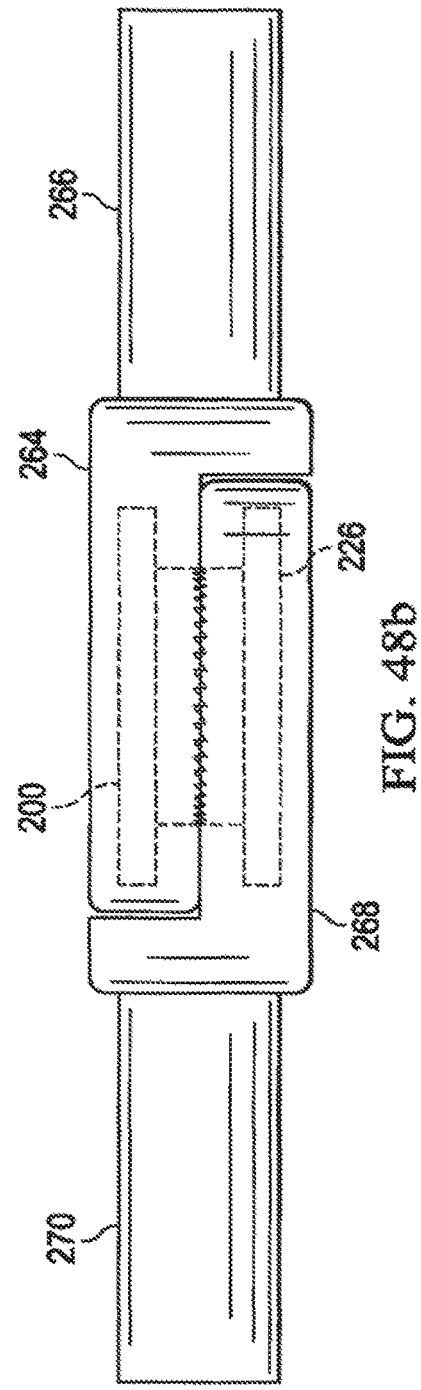

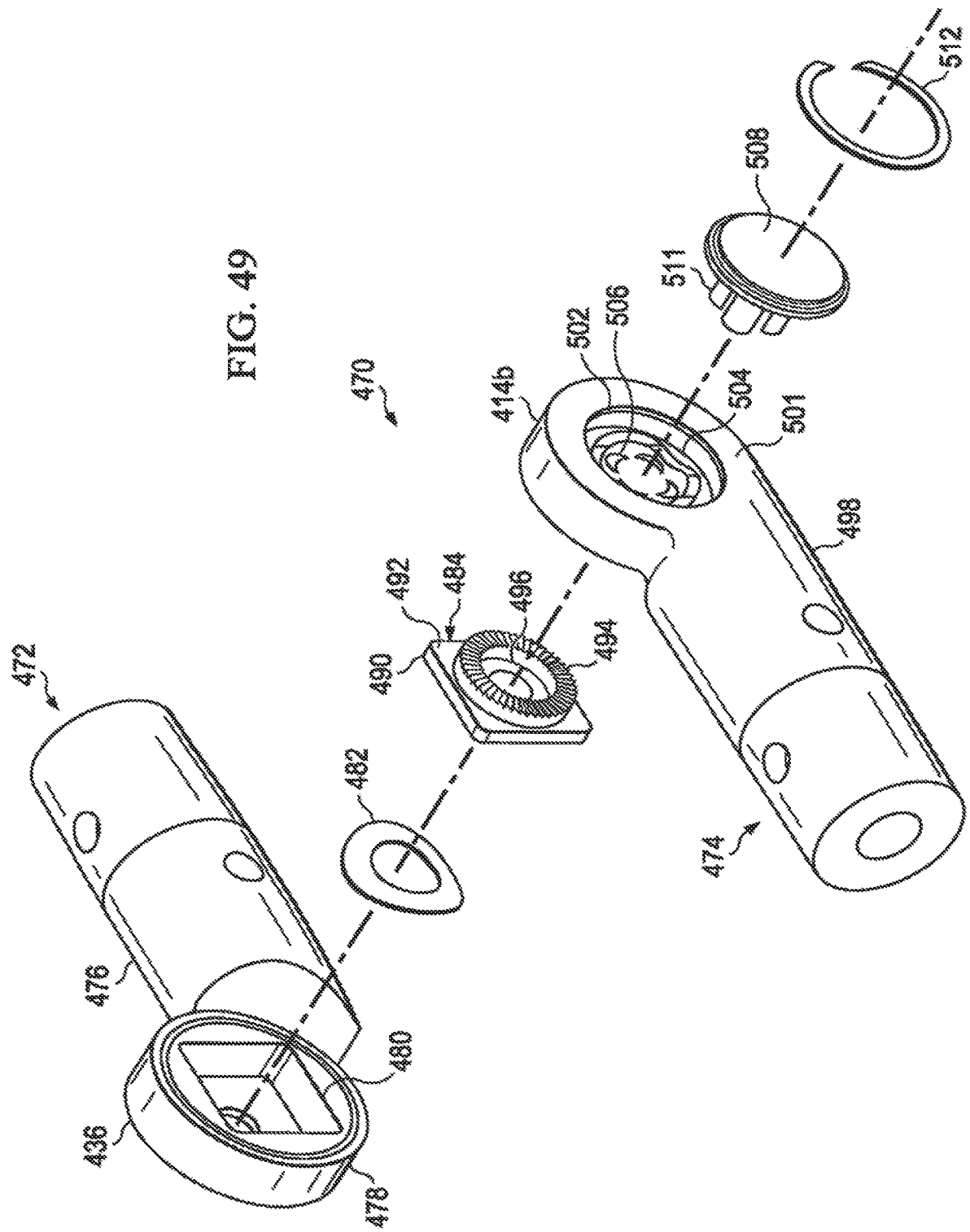

PEDICLE SCREW HAVING A REMOVABLE ROD COUPLING

CROSS-REFERENCE TO RELATED APPLICATIONS

This application is a Continuation of U.S. patent application Ser. No. 15/350,163, filed Nov. 14, 2016 (published as U.S. Pat. Pub. No. 2017-0056074), which is a Continuation of U.S. patent application Ser. No. 15/017,023, now U.S. Pat. No. 9,526,527, filed Feb. 5, 2016, which is a Continuation of U.S. patent application Ser. No. 13/672,150, filed on Nov. 8, 2012, now U.S. Pat. No. 9,345,517, which is a Continuation-In-Part of U.S. patent application Ser. No. 13/410,035 filed Mar. 1, 2012, now U.S. Pat. No. 9,579,126, which is a Continuation-In-Part of U.S. patent application Ser. No. 12/364,412 filed Feb. 2, 2009, now U.S. Pat. No. 9,408,641, which claims priority to U.S. Provisional Application Ser. No. 61/025,761, filed Feb. 2, 2008, and to U.S. Provisional Application Ser. No. 61/080,162 filed Jul. 11, 2008, the contents of each which are incorporated herein by reference in their entireties for all purposes.

FIELD OF THE INVENTION

The present invention relates in general to the field of bone fixation, and more particularly, to a novel pedicle screw having a removable rod coupling for use during the surgical correction of mild to severe rigid spinal deformities.

BACKGROUND OF THE INVENTION

Without limiting the scope of the invention, its background is described in connection with pedicle screws. In rigid severe spine deformity with coronal or sagittal decompensation, translation of the spinal column is necessary for restoration of trunk balance as well as deformity correction. However, the conventional correction methods, such as posterior correction only or anterior release and posterior instrumentation, are usually unsatisfactory. Therefore, a more aggressive approach, such as reconstructive techniques, is necessary. In 1922, Maclennan[1] first illustrated vertebrectomy and demonstrated an apical resection from a posterior-only approach with postoperative casting for the treatment of severe scoliosis. Several authors[2-8] have subsequently reported their experience with vertebrectomy, mostly for congenital scoliosis. In 1987, Bradford[9] performed both anterior and posterior vertebral column resection (VCR) with spinal shortening and posterior instrumentation and fusion demonstrating excellent restoration of coronal with relatively few complications. Leatherman[6] introduced a two-stage anterior and posterior correction procedure for congenital spinal deformity. Bradford and Bochie-Adjei[10] also reported a single stage anterior and posterior resection of hemivertebra and spinal arthordesis. However, the anterior-posterior vertebral column resection (VCR) has disadvantages such as long operative time, potential significant blood loss, and risk of intraoperative neurologic impairment due to the spinal column segment instability during the resection and the correction procedure.

In 2002, Suk[11-13] introduced a technique of a single posterior approach to perform VCR (PVCR) that offered significant advantages over the combined anterior-posterior VCR. The surgery consisted of temporary stabilization of the vertebral column with segmental pedicle screw fixation, resection of the vertebral column at the apex of the deformity via the posterior route, followed by gradual deformity correction and global fusion. In the surgical technique, multiple pedicle screws were utilized proximal and distal to the vertebral resection to securely fix the spine prior to any bony resection. Provisional single rod placement is performed during the bony resection to prevent sudden spinal column translations which may result in spinal cord injury. The vertebral column resection and deformity correction were carried out either by exchanging the temporary pre-contoured rods one by one or by in situ rod bending. However, these techniques have a number of disadvantages: 1) the risk of intraoperative mishaps due to the instability resulting from exchanging the temporary rods may produce spinal cord injury; 2) limitation in deformity correction secondary to a "one-time" correction maneuver utilized using the Suk technique; 3) short segment fixation using the provisional rods since multiple exchanges prevent long rod utilization; and 4) additional surgical time necessary with multiple removal and insertion of the temporary provisional rods.

One such fixation system is taught in U.S. Pat. No. 7,220,262, issued to Hynes. Briefly, the spinal fixation system and related methods include pedicle screws secured in two columns, one along each side of the spine. Cross support rods have ends connected to pedicle screw heads. A longitudinally extending rod is supported on the cross supports and recessed in the cavity created by removal of portions of spinous processes, providing a reduced profile of the installed construct. Several types of cross supports are shown, such as: arms from the screws inward to rings or yokes connecting the longitudinal rod; cross rods with ends connected to the screws and having centrally-located yokes for the longitudinal rod; cross rods with articulating longitudinal rod portions fixed or swiveled to them. These cross rods may have end portions angled posterior toward anterior to accommodate lateral positioned pedicle screws, but shorter cross rods without angled end portions enable medialized pedicle screw orientation.

U.S. Publication No. US20070270810, filed by Sanders is directed to a pedicle screw spinal rod connector arrangement. Briefly, a pedicle screw spinal rod connector arrangement is provided that includes in a body having an opening for mounting a head of an inserted pedicle screw. A bracket connected with the body forms a lateral restraint. A bridge is connected with and extends over the body. A spinal rod-receiving slot is provided between the bridge and the bracket. The connector arrangement also has a wedge axially offset from the pedicle screw moveable downward by a setscrew mounted with the bridge. The wedge imparts a locking force on the pedicle screw head and a generally lateral locking force on the spinal rod.

Yet another example is shown in U.S. Publication No. US20070233062, filed by Berry for a pedicle screw system with offset stabilizer rod. In this example, an improved pedicle screw system is provided with an offset stabilizer rod for the internal fixation of the spine. The pedicle screw system includes at least two multi-angle pedicle screw units adapted for anchored securement to patient bone, and an elongated stabilizer rod extending there between. Each pedicle screw unit includes a bone screw associated with an anchor bracket defining a laterally offset and upwardly open channel or trough for receiving and supporting the stabilizer rod. A securement member such as a set screw is fastened to the anchor bracket for compressively retaining the stabilizer rod within the bracket channel or trough. The securement member may also bear against the associated bone screw for compressively retaining the screw in position relative to the anchor bracket.

SUMMARY OF THE INVENTION

The present invention solves various problems of current spinal fixation systems and the control of the positioning of temporary rods during spinal surgery. The present invention allows the surgeon to stabilize the spine, effectively derotate the spine, safely translate the spine, and when required, easily derotate and translate the spine to treat spinal deformities.

The present invention provides a pedicle screw for spinal fixation comprising: a bone fastener portion, wherein the bone fastener portion is at least partially threaded; a permanent rod coupling comprising a bottom surface connected to the bone fastener portion, a middle section positioned between the bottom surface and a top surface, a lateral rod opening in a portion of the middle section adapted to receive a permanent rod, a threaded bore that extends from the top surface into the lateral rod opening, a permanent rod fastener mated to fit the threaded bore to extend into the lateral rod opening, wherein the permanent rod fastener can engage a permanent rod positioned in the lateral rod opening, and a transition region on a portion of the top surface; a breakaway portion in the transition region; a temporary rod coupling connected to the transition region, wherein the temporary rod coupling comprises a temporary rod channel adapted to receive a temporary rod, an upper threaded opening that extends into the temporary rod channel, and an upper rod fastener mated to the upper threaded opening, wherein the upper rod fastener can engage the temporary rod positioned in the temporary rod channel; wherein the permanent rod is positioned in the lateral rod opening and secured by the permanent rod fastener during the bone alignment and the temporary rod is temporarily positioned in the temporary rod channel and secured by the upper rod fastener during a bone realignment and when the temporary rod is not needed the temporary rod coupling can be removed at the transition region by separation at the breakaway portion to leave the top surface.

The permanent rod fastener, the upper rod fastener or both are threaded. The lateral rod opening and the temporary rod channel may be generally perpendicular. The temporary rod channel and the bone fastener portion may be generally parallel. The lateral rod opening and the bone fastener portion may be generally perpendicular. The permanent rod fastener, the upper rod fastener or both may further include a locking pin to prevent movement. The bone fastener may be permanently attached to the permanent rod coupling. The bone fastener may be semi-permanently attached to the permanent rod coupling to allow the permanent rod coupling to be positioned at a variable angle relative to the bone fastener.

The present invention provides a method of spinal fixation using pedicle screws by fastening two or more pedicle screws into two or more vertebra, wherein the each of the two or more pedicle screws comprise a bone fastener portion; a permanent rod coupling comprising a bottom surface connected to the bone fastener portion, a middle section positioned between the bottom surface and a top surface, a lateral rod opening in a portion of the middle section adapted to receive a permanent rod, a threaded bore that extends from the top surface into the lateral rod opening, a permanent rod fastener mated to fit the threaded bore to extend into the lateral rod opening, wherein the permanent rod fastener can engage a permanent rod positioned in the lateral rod opening, and a transition region on a portion of the top surface; a breakaway portion in the transition region; a temporary rod coupling connected to the transition region, wherein the temporary rod coupling comprises a temporary rod channel adapted to receive a temporary rod, an upper threaded opening that extends into the temporary rod channel, and an upper rod fastener mated to the upper threaded opening, wherein the upper rod fastener can engage the temporary rod positioned in the temporary rod channel; and interconnecting the two or more pedicle screws by securing the permanent rod in the lateral rod opening of at least two of the two or more pedicle screws, securing the temporary rod in the temporary rod channel of at least two of the two or more pedicle screws, or both. The method may further include the step of removing the temporary rod from the temporary rod channel. The may further include the step of breaking the temporary rod coupling at the breakaway portion of the transition region to leave the top surface.

The present invention provides a pedicle screw kit for spinal fixation comprising two or more pedicle screws, wherein each of the two or more pedicle screws comprise a bone fastener portion, wherein the bone fastener portion is at least partially threaded; a permanent rod coupling comprising a bottom surface connected to the bone fastener portion, a middle section positioned between the bottom surface and a top surface, a lateral rod opening in a portion of the middle section adapted to receive a permanent rod, a threaded bore that extends from the top surface into the lateral rod opening, a permanent rod fastener mated to fit the threaded bore to extend into the lateral rod opening, wherein the permanent rod fastener can engage a permanent rod positioned in the lateral rod opening, and a transition region on a portion of the top surface; a breakaway portion in the transition region; a temporary rod coupling connected to the transition region, wherein the temporary rod coupling comprises a temporary rod channel adapted to receive a temporary rod, an upper threaded opening that extends into the temporary rod channel, and an upper rod fastener mated to the upper threaded opening, wherein the upper rod fastener can engage the temporary rod positioned in the temporary rod channel; wherein the permanent rod is positioned in the lateral rod opening and secured by the permanent rod fastener during the bone alignment and the temporary rod is temporarily positioned in the temporary rod channel and secured by the upper rod fastener during a bone realignment and when the temporary rod is not needed the temporary rod coupling can be removed at the transition region by separation at the breakaway portion to leave the top surface. The kit may further include a breakaway tool adapted to fit the temporary rod coupling to break off the temporary rod coupling. The kit may further include one or more rod link reducers, at least one permanent rod, at least one temporary rod, one or more leverage handles or a combination thereof.

BRIEF DESCRIPTION OF THE DRAWINGS

For a more complete understanding of the features and advantages of the present invention, reference is now made to the detailed description of the invention along with the accompanying FIGURES and in which:

FIGS. 11, 12, and 13 show the first step in a spinal fixation process.

FIG. 14 shows the use of the rod link reducer and pedicle screw of the present invention.

FIG. 27 is a picture that illustrates a cross sectional view of the rod-link reducer on the coronal plane.

FIG. 28 is a picture that illustrates a cross sectional view of the rod-link reducer on the sagittal plane.

FIGS. 48A and 48B are images of the joint adapted into a larger device.

FIG. 49 is an exploded isometric image of the joint adapted into a larger device.

DETAILED DESCRIPTION OF THE PREFERRED EMBODIMENTS

Figure 2A:
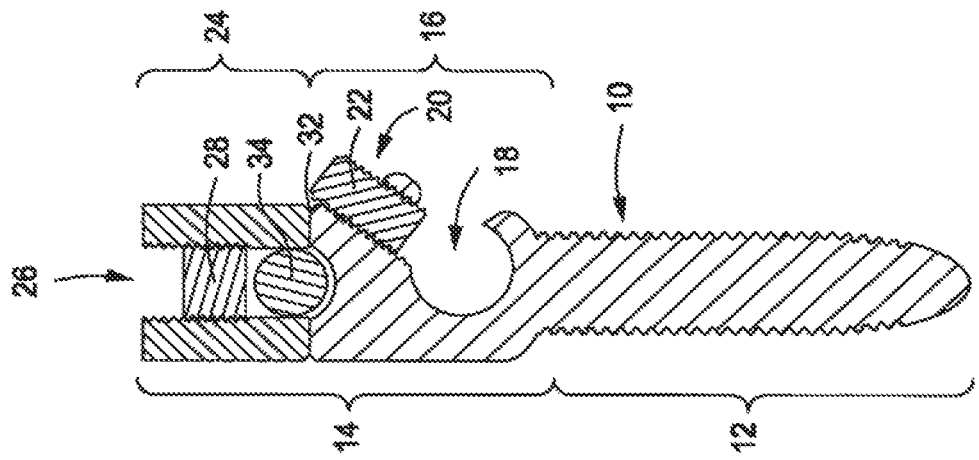
FIGS. 2A-2C show a cross-sectional view of the pedicle screw in operation.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Posterior vertebral column resection (PVCR) can be used for correction of the most severe spinal deformities. Current implant strategies used for more common and moderate spinal deformity are not ideal for those complex cases. Therefore, they do not provide continuous stability of the spine as one transition between resection and correction, are cumbersome, and the application of correction forces are not ideal. The new system disclosed herein was designed specifically to surgically treat severe spinal deformity.

The treatment of severe rigid spinal deformity is a demanding and difficult surgical challenge. The PVCR has been considered to be an effective alternative to the conventional anteriorposterior VCR in severe rigid spinal deformity. However, the current implant strategies used during PVCR allow for limited correction, potential risk of spinal cord injuries, and long operative time. This new instrumentation system of the present invention offers: 1) better maintenance of spinal stability throughout the surgical procedure to reduce risk of the spinal cord injuries; 2) more reliable reconstruction of the vertebral column; 3) better and easier correction of the deformity; and 4) shorter operative time.

The novel pedicle screw/rod-link reducer posterior instrumentation system was developed to provide a safer, easier and improved deformity correction, as well as shorter surgical time for the PVCR of the severe spinal deformity. Biomechanical evaluation of this system demonstrated spinal stability throughout the surgical procedure to reduce the risk of spinal cord injuries.

The temporary rod/rod-link reducer construct provided similar stiffness and stability compared to the provisional and final rod constructs. This new system offers a safer, easier and improved deformity correction, as well as shorter surgical time for the PVCR of the severe spinal deformity.

Significance: Current implant strategies used for more common and moderate spinal deformity are not ideal for the most severe spinal deformities. A novel pedicle screw/rod-link reducer has been designed to offer better maintenance of spinal stability throughout the surgical procedure to reduce risk of the spinal cord injuries. This system therefore provides a safer, easier and improved deformity correction, as well as shorter surgical time for the PVCR of the severe spinal deformity.

Implant Components: The instrumentation system of the present invention includes one or more of the following components: a pedicle screw, a rod-link reducer, reduction handle, temporary long rod, and final rod. The pedicle screw includes a threaded shank for insertion into the bone and a screw head having a first aperture and a second aperture. The first aperture has a basic "U" (tulip) shape (top-loading component) that extends from the top of the screw head and is open on both sides of the screw head to receive a first longitudinal member (a temporary rod) and a set of female threads formed in the inner walls of the first aperture. A first compression member engages the set of female threads of the first aperture and the face of the first compression member contacts the first longitudinal member. The second aperture has a basic "C" shape (side-loading component) that lines up superior to the threaded shank and inferior to the first aperture. The second aperture is open on both sides of the head to receive a second longitudinal member (a final rod). The second aperture also includes a second set of female threads that accommodate a second compression member that screwably engages the second set of female threads, and the face of the second compression member contacts the second longitudinal member. There is a breakaway mechanism between the first and second apertures.

The rod-link reducer has a basic "H" shape that rigidly links and locks the first longitudinal members (temporary rods). The rod-link reducer includes: 1) two top-tightening locking mechanisms (break-off set screws) which provide access and ensure the adequate grip on the temporary rods by the set screws; 2) an adjustable central mechanism functioning in a multi-axial manner, allowing attachment to the rod at any orientation in the coronal, sagittal, and transverse planes, said mechanism allowing for compression, distraction, derotation and cantilever method; 3) two adjustable lateral mechanisms (break-off set screws) which allow the locking mechanisms to adequately attach to the temporary rods; and 4) two squared ends that connect with two reduction handles.

The reduction handle is a column shape and has two portion ends. The first end has a squared access that connects with the squared end of the rod-link reducer. The second end is a solid column. The temporary rod and the final rod are the diameter of 5.5 mm rods those are made of stainless steel or titanium.

In operation, the present invention is used as follows: With the spine exposed posteriorly, the pedicle screw is inserted segmentally, except for the resected levels (apex). The spine is then divided into cephalad and caudal portions by the resected levels. At the cephalad portion, two temporary rods are fixed on the convex and concave side via the first aperture of the pedicle screw respectively. Another two temporary rods is then similarly fixed at the caudal portion. The two temporary rods on the concave side are then connected with a rod-link reducer and locked to the shape of the deformity without any attempt at correction. Resection of the vertebral column is then performed at the convex side of the apex. Following resection on the convex side, another rod-link reducer is connected and locked on the two convex temporary rods. The resection of the remaining vertebra is then performed on the concave side.

Deformity correction is performed by loosening the adjustable central mechanism of the rod-link reducer on the convex side with the reduction handles, which is then gradually compressed to shorten the resected gap. During the compression, the resected gap on the convexity, the central part of rod-link reducer on the concavity is gradually loosened to match the compression/shortening on the convexity.

After deformity correction, two final rods are fixed on the convex and concave side via the second aperture of the pedicle screw respectively. The two rod-link reducers are then unlocked and all temporary rods are removed. A custom wrench is then used to remove the first aperture parts of the pedicle screw.

The pedicle screw and any of its components including the bone fastener, threads, neck and screwhead, are comprised of a non-organic material that is durable and that can be implanted in a human body, such as titanium, stainless steel, spring steel, aluminum, Niobium, carbon fiber, ceramics, polymers, composites or any relatively hard material (e.g. Titanium-Aluminium-Niobium-alloy). Generally, the material selected is biocompatible, that is, compatible with the surrounding bone and tissue.

The present invention provides a substantial improvement in addressing clinical problems indicated for surgical treatment of chronic or acute spinal injuries, including traumatic spinal injuries, scoliosis (abnormal lateral curvature of the spine), kyphosis (abnormal forward curvature of the spine, often in the thoracic spine), excess lordosis (abnormal backward curvature of the spine, often in the lumbar spine), spondylolisthesis (forward displacement of one vertebra over another, often in a lumbar or cervical spine) and other disorders caused by abnormalities, disease or trauma, such as ruptured or slipped discs, degenerative disc disease, fractured vertebra, and the like.

The present inventors recognize that there are other disadvantages of the current implant strategies used during Posterior Vertebral Column Resection (PVCR) that have been overcome by designing a new pedicle screw posterior instrumentation system. The present invention includes screws, methods, kits and systems that provide a safer, easier and better correction, as well as shorter operation time method, for the PVCR of the severe spinal deformity. The present invention takes advantage of the top-loading and side-loading current designs as well as a universal connecting link to provide three-dimensional correction. These components provide: 1) continued stabilization of the spine during bony resection as well as correction; 2) allow for controlled correction of the spine using both rods; and 3) provide the ability to place the permanent rods while the long provisional rod is in place so that instability is not created.

The present invention includes: 1) a pedicle screw with a screw head that can receive two rods. The bone screw head includes two rod-receivers. One receiver member is basic "U" shape (top-loading component) that extends from the top of the screw head to receive a temporary rod. Another receiver member has a basic "C" shape (side-loading component) that is inferior to the first receiver. The second receiver receives a final rod. There is also a breakaway mechanism between the first and second apertures so that the first aperture can be removed while the final rod is fixed; 2) a rod-link reducer has a basic "H" shape that rigidly links and locks the temporary rods, which allows attachment to the rod at any orientation in the coronal, sagittal, and transverse planes so as to make compression, distraction, derotation and cantilever method; 3) a reduction handle that connects with the rod-link reducer; and 4) a 5.5 mm diameter rod. For the PVCR of severe spinal deformity, this instrumentation system would provide: 1) better maintenance of spinal stability throughout the surgical procedure to reduce risk of the spinal cord injuries; 2) more reliable reconstruction of the vertebral column; 3) better and easier correction of the deformity; and 4) shorter operative time.

More particularly, the present invention includes a rod link reducer for a spinal fixation system. The rod link reducer includes a first and a second spinal rod manipulator; a first spinal rod manipulator joint connected to the first spinal rod manipulator and a second spinal rod manipulator joint connected to the second spinal rod manipulator; a first and a second translatable transverse shaft connected to the first and second joints, respectively; and a universal reducer connected to both the first and second translatable transverse shafts, wherein the reducer, the shafts and the linkers provide movement and temporary fixation of a spine that has been manipulated into a final position during spinal surgery. In one aspect, the spinal rod manipulator is further defined as comprising a handle and a rod attachment fixation point, wherein the rod attachment fixation point at least partially surrounds a rod with a semi-permanent fastener. In another aspect, the first, the second or both the first and second translatable transverse shafts connects to the universal reducer and are capable of sliding to increase or decrease the distance between the first and second joints. The universal reducer can be, for example, a ball joint, a universal joint, a pivot, a slot, a collar, a bearing, a dove-tail, a ball-joint, a gimbal, a level, or a sleeve that permits movement of the translatable transverse shafts in two or more dimensions. In another aspect, the universal reducer includes a fastener that semi-permanently fixes the position of the reducer in relation to the first, the second or both translatable transverse shafts. The first and second joints may each include an independent fastener that semi-permanently fixes the relative position of the first spinal rod manipulator to the first translatable transverse shaft, the second spinal rod manipulator to the second translatable transverse shaft or both the first and second spinal rod manipulator to the first and second translatable transverse shafts, respectively. Any component of the rod link reducer may be comprised of titanium, stainless steel, spring steel, aluminum, Niobium and alloys thereof, carbon fiber, ceramics, polymers, composites, or combinations thereof.

In another embodiment, the present invention includes a method of correcting a spinal deformity by fastening two or more pedicle screws into two or more vertebra; interconnecting the pedicle screws with two or more temporary rods; connecting a link reducer between the temporary rods, the rod link reducer having a first and a second spinal rod manipulator; a first spinal rod manipulator joint connected to the first spinal rod manipulator and a second spinal rod manipulator joint connected to the second spinal rod manipulator; a first and a second translatable transverse shaft connected to the first and second joints, respectively; and a universal reducer connected to both the first and second translatable transverse shafts, wherein the reducer, the shafts and the linkers provide movement and temporary fixation of a spine that has been manipulated into a final position during spinal surgery. Next, the user correct the position of the spine by manipulating the temporary rods attached to the pedicle screws; interconnects the pedicle screws with a permanent fixation rod; and finally removes the temporary rod. One example of a pedicle screw for use with the present invention may include a bone fastener and a rod coupling head, the rod coupling head comprising a lower and an upper rod coupling: the lower rod coupling including a lateral rod opening adapted to receive a permanent rod; an angled bore extends into the lateral rod opening; and a permanent rod fastener in the angled bore to engage a permanent rod in the lateral rod opening; and a upper rod coupling having: an upper rod opening adapted to receive a temporary rod, wherein the upper rod opening is formed to receive a temporary rod fastener, wherein the upper rod coupling is detachable from the lower rod coupling at a transition, wherein a temporary rod is temporarily affixed into the upper rod opening during a bone realignment and a permanent rod is positioned in the lateral rod opening and engaged by the permanent rod fastener upon final bone alignment. In one aspect, the spinal rod manipulator is further defined as comprising a handle and a rod attachment fixation point, wherein the rod attachment fixation point at least partially surrounds a rod with a semi-permanent fastener. In another aspect, the first, the second or both the first and second translatable transverse shafts connect to the universal reducer and are capable of sliding to increase or decrease the distance between the first and second joints. The universal reducer may include a ball joint, a universal joint, a pivot, a slot, a collar, a bearing, a dove-tail, a ball-joint, a gimbal, a level, or a sleeve that permits movement of the translatable transverse shafts in two or more dimensions. In another aspect, the universal reducer may include a fastener that semi-permanently fixes the position of the reducer in relation to the first, the second or both translatable transverse shafts. The first and second joints may each include an independent fastener that semi-permanently fixes the relative position of the first spinal rod manipulator to the first translatable transverse shaft, the second spinal rod manipulator to the second translatable transverse shaft, or both the first and second spinal rod manipulator to the first and second translatable transverse shafts, respectively.

The present invention also includes a kit that includes a rod link reducer of a spinal fixation system, the rod link reducer having a first and a second spinal rod manipulator; a first spinal rod manipulator joint connected to the first spinal rod manipulator and a second spinal rod manipulator joint connected to the second spinal rod manipulator; a first and a second translatable transverse shaft connected to the first and second joints, respectively; and a universal reducer connected to both the first and second translatable transverse shafts, wherein the reducer, the shafts and the linkers provide movement and temporary fixation of a spine that has been manipulated into a final position during spinal surgery. The kit may also include two or more pedicle screws into two or more vertebra, the pedicle screw including a bone fastener and a rod coupling head, the rod coupling head comprising separate lower and upper lower rod couplings: the lower rod coupling including: a lateral rod opening adapted to receive a permanent rod; an angled bore extends into the lateral rod opening; and a permanent rod fastener in the angled bore to engage a permanent rod in the lateral rod opening; and a upper rod coupling including: an upper rod opening adapted to receive a temporary rod, wherein the upper rod opening is formed to receive a temporary rod fastener; and two or more temporary rod fasteners. The kit may also include at least one of two or more permanent rods, two or more temporary rods, one or more rod link reducers, a plurality of pedicle screws and one or more leverage handles.

Figure 1:
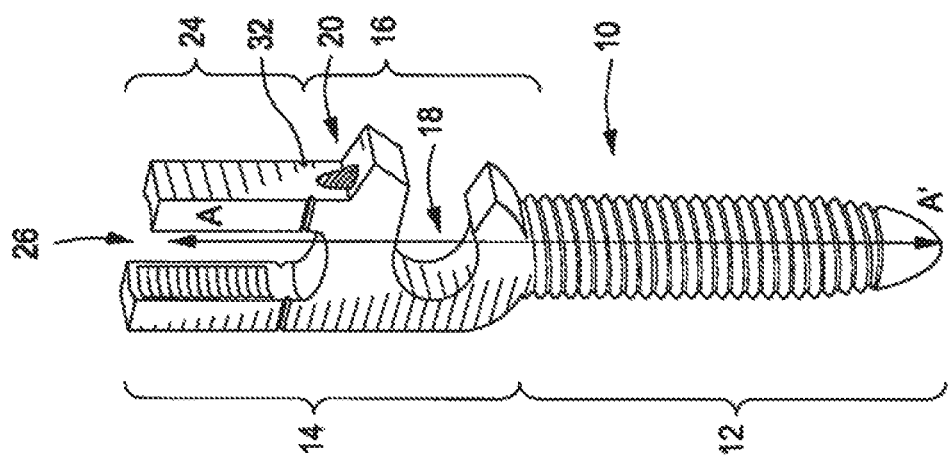
FIG. 1 shows one embodiment of the pedicle screw of the present invention.

FIG. 1 shows one embodiment of the pedicle screw 10 of the present invention. The pedicle screw 10 includes a bone fastener 12 and a rod coupling head 14. The rod coupling head 14 includes a lower rod coupling 16 having a lower rod opening 18, depicted in a lateral configuration. The lower rod opening 18 may have any angle so long as the material of the pedicle screw 10 that surrounds the lower rod opening 18 is sufficiently strong to retain and affix a permanent rod. The lower rod coupling 16 also includes a bore 20, through which a permanent rod fastener 22 can be inserted to fasten a permanent rod. As in the case of the lower rod opening 18, the material of the pedicle screw 10 surrounding the bore 20 will also be sufficiently strong to retain and affix a permanent rod. The upper rod coupling 24 has an upper rod opening 26. The upper rod coupling 24 is formed to permit the user to insert a temporary rod using a temporary rod fastener 28. The lower and upper rod couplings 16 and 24, respectively will often be made of unitary construction. For illustration purposes, and not necessarily as an element or limitation, a transition 32 is denoted. In unitary embodiments, the transition 32 may be modified (e.g., notched, cut, scratched or weakened) to provide for the breakage of the upper rod coupling 24. In another embodiment, the transition 32 may provide a semi-permanent attachment between the lower rod coupling 16 and the upper rod coupling 24, such that the transition is a universal joint, a pivot, a slot, a collar, a bearing, a dove-tail, a ball-joint, a gimbal, a level, or a sleeve. Likewise, the lower rod coupling 16 and the bone fastener may be connected with a universal joint, a pivot, a slot, a collar, a bearing, a dove-tail, a ball-joint, a gimbal, a level, or a sleeve. When made in a unitary construction, the pedicle screw 10 may be machined, sintered, cast, welded or glued as long as the pedicle screw is of sufficient strength for the bone fixation application.

Figure 2C:
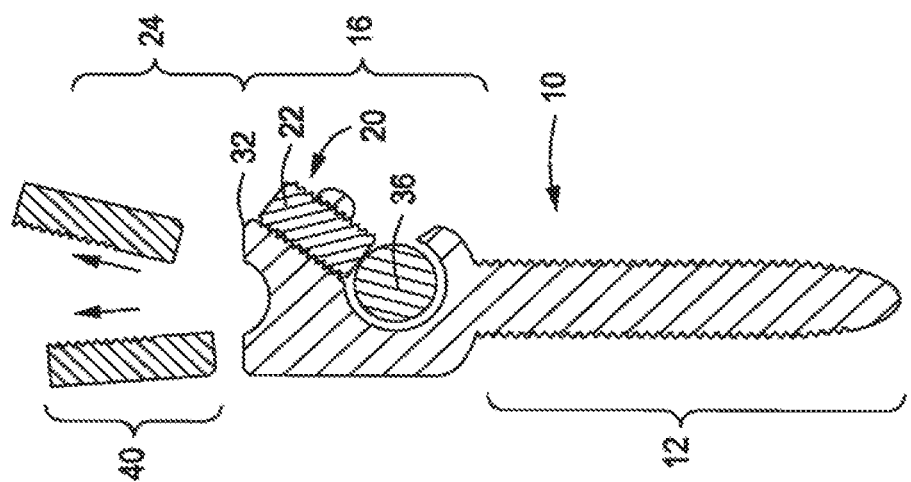
Figure 2B:
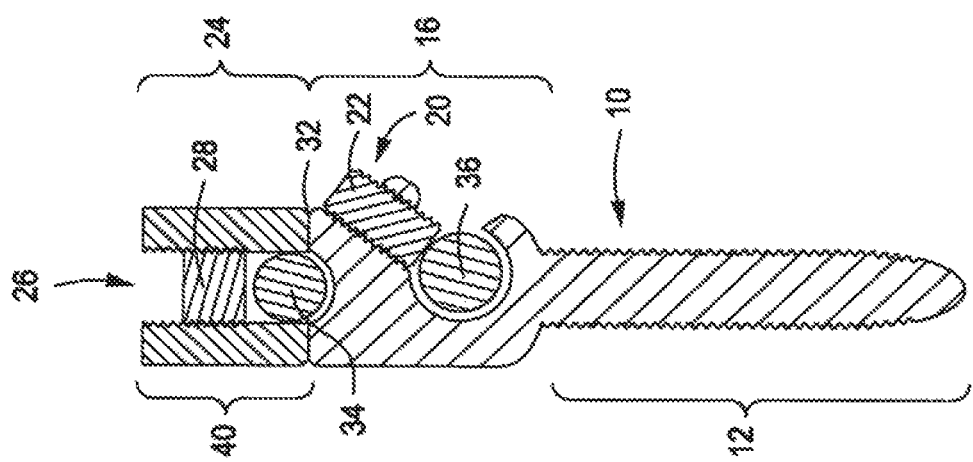

FIGS. 2A to 2C show a cross-sectional view of the pedicle screw 10 in operation. In FIG. 2A, the pedicle screw has been affixed to a bone (not depicted), and a temporary rod 34 has been inserted into the upper rod opening 26 and semi-permanently affixed using the temporary rod fastener 28. In the embodiment depicted, the upper rod opening 26 is shown internally threaded, and the temporary rod fastener 28 is shown externally threaded. The skilled artisan will recognize that the present invention also includes fastener embodiments in which the threading is reversed, the threading is external to the upper rod coupling, and the fastener is internally threaded, the fastener is a cap, the fastener and the coupling snap together, are wedged together, twist and lock. Likewise, the permanent rod fastener is also able to engage the permanent rod in a variety of manners, including pins, latches, threading, snapping, wedging and locking. The permanent rod may even be glued or welded.

FIG. 2B shows the addition of the permanent rod 36 in addition to the temporary rod 34. Next, the temporary rod fastener 28 and the temporary rod are removed (not depicted). Finally, FIG. 2C shows the final assembly in which the upper rod coupling is removed completely by breaking the upper rod coupling into tabs 40 at breakpoints 38.

Figures 3A, 3B:
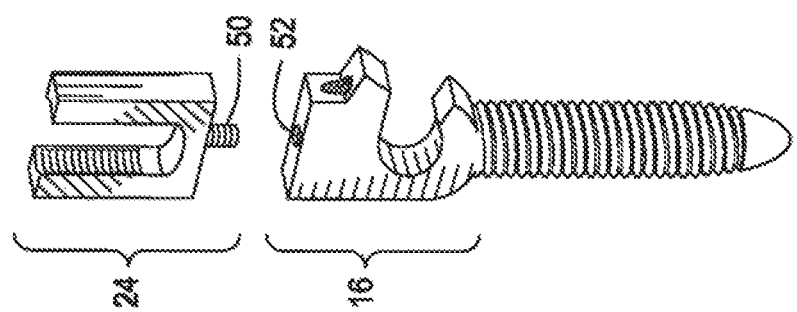
FIGS. 3A and 3B show an isometric view and a cross-sectional view, respectively, of the pedicle screw.

FIGS. 3A and 3B shows an isometric view and a cross-sectional view, respectively, of the pedicle screw 10 in which the lower rod coupling 16 and the upper rod coupling 24 are connected, and in which a screw portion 50 is fastened into opening 52, allowing the potential for some rotations about the axis of the screw portion 50. After the permanent rod has been affixed into the pedicle screw 10, the upper rod fastener 24 is removed.

FIGS. 3A and 3B show an isometric view and a cross-sectional view, respectively, of the pedicle screw 10 in which the lower rod coupling 16 and the upper rod coupling 24 are connected, and in which a screw portion 50 is fastened into opening 52, allowing the potential for some rotations about the axis of the screw portion 50. After the permanent rod has been affixed into the pedicle screw 10, the upper rod fastener 24 is removed.

Figures 4A, 4B:
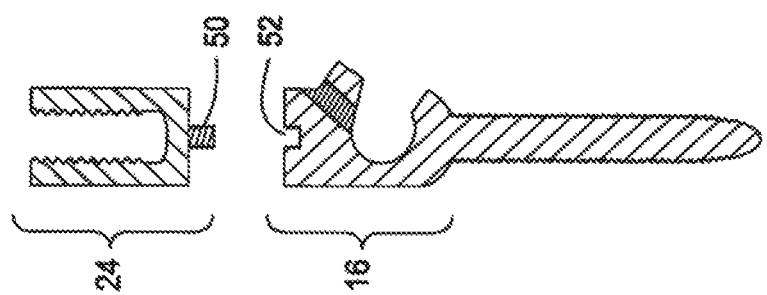
FIGS. 4A and 4B show an isometric view and a cross-sectional view, respectively, of the pedicle screw.

FIGS. 4A and 4B show an isometric view and a cross-sectional view, respectively, of the pedicle screw 10 in which the lower rod coupling 16 and the upper rod coupling 24 are connected by and in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. The screw 54 also permits control over the mechanical force required to rotate the upper rod coupling 24. For configurations in which the lower rod coupling 16 and the upper rod coupling 24 are separate, the interface between the two may be smooth, rough or patterned (e.g., random or non-random) or coated.

Figures 5A, 5B:
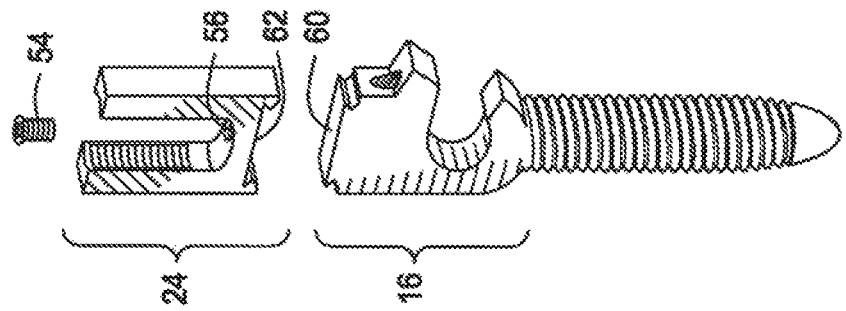
FIGS. 5A and 5B show an isometric view and a cross-sectional view, respectively, of the pedicle screw.

FIGS. 5A and 5B show an isometric view and a cross-sectional view, respectively, of the pedicle screw 10 in which the lower rod coupling 16 and the upper rod coupling 24 are connected by and in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of an opening 60 that dove-tails with a notch 62. The notch 62 can even be placed at an angle or can also be made square such that the upper rod coupling 24 can be placed parallel or perpendicular to the direction of the permanent or temporary rods.

Figures 6A, 6B:
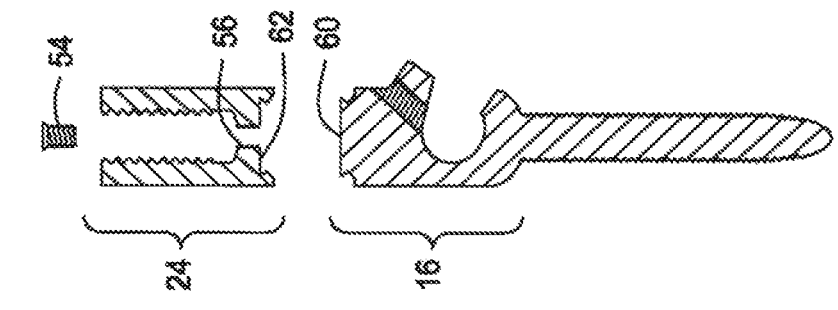
FIGS. 6A and 6B show an isometric view and a cross-sectional view, respectively, of the pedicle screw.

FIGS. 6A and 6B show an isometric view and a cross-sectional view, respectively, of the pedicle screw 10 in which the lower rod coupling 16 and the upper rod coupling 24 are connected by and in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of a slit 60 that dove-tails with an external notch 62. The notch 62 can even be placed at an angle or can also be made square such that the upper rod coupling 24 can be placed parallel or perpendicular to the direction of the permanent or temporary rods.

Figures 7A, 7B:
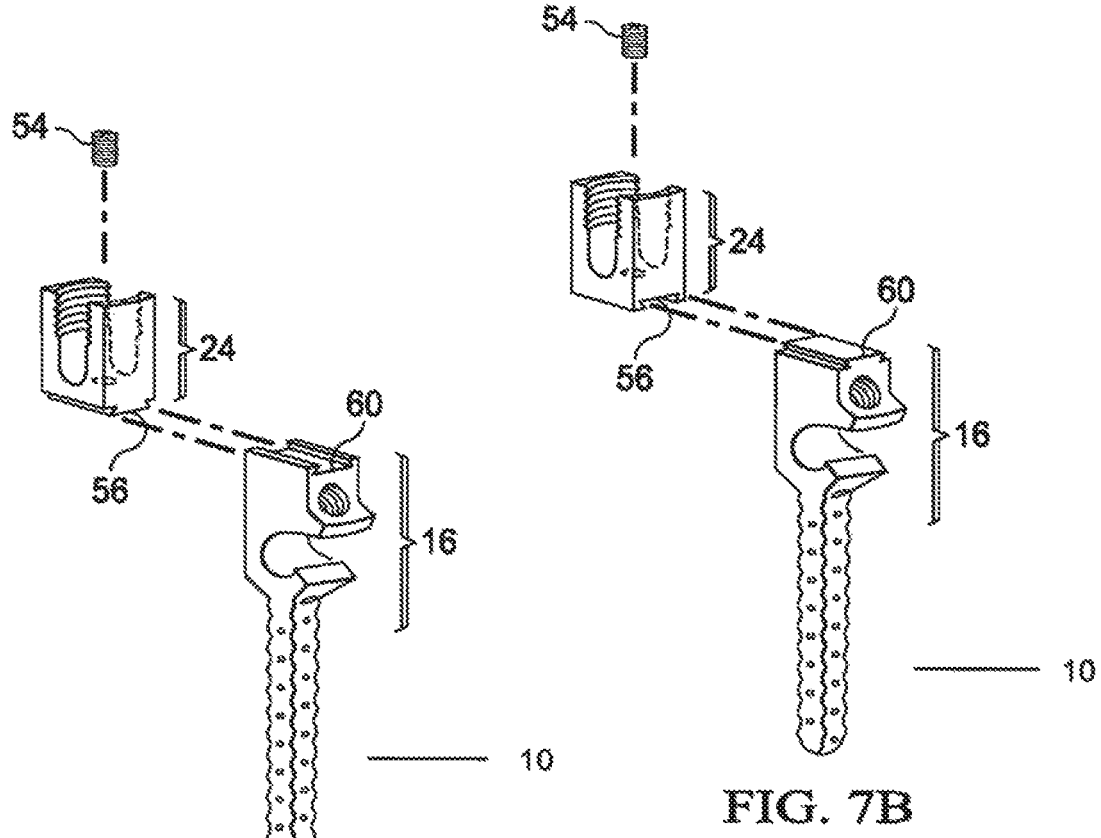
FIGS. 7A and 7B show an isometric view and a cross-sectional view, respectively, of the pedicle screw.

FIGS. 7A and 7B show an isometric view and a cross-sectional view, respectively, of the pedicle screw 10 in which the lower rod coupling 16 and the upper rod coupling 24 are connected by and in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of dove-tail joints (shown in two different configurations). The notch 62 can even be placed at an angle or can also be made square such that the upper rod coupling 24 can be placed parallel or perpendicular to the direction of the permanent or temporary rods.

Figure 8:
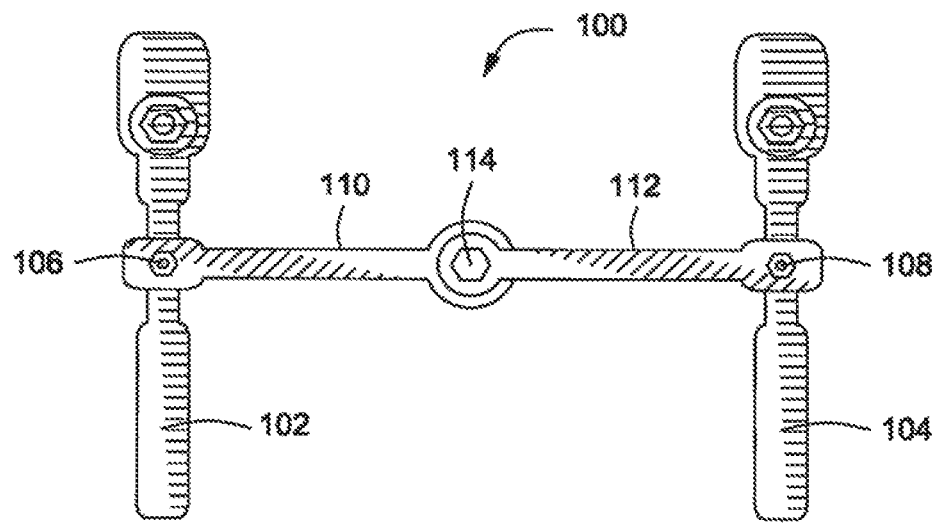
FIG. 8 shows a rod link reducer 100 for use with the present invention.

FIG. 8 is an isometric view of a rod link reducer 100 for use with the present invention. The rod link reducer 100 includes first and second spinal rod manipulators 102, 104, which are connected to a first spinal rod manipulator joint 106 connected to the first spinal rod manipulator 102 and a second spinal rod manipulator joint 108 connected to the second spinal rod manipulator 104. First and second translatable transverse shafts 110, 112 connected to the first and second joints 106, 108, respectively, which are connected to a reducer 114 connected to both the first and second translatable transverse shafts 110, 112, wherein the reducer 114, the shafts 110, 112 and the linkers 106, 108 provide movement and temporary fixation of a spine that has been manipulated into a final position during spinal surgery.

Figure 9:
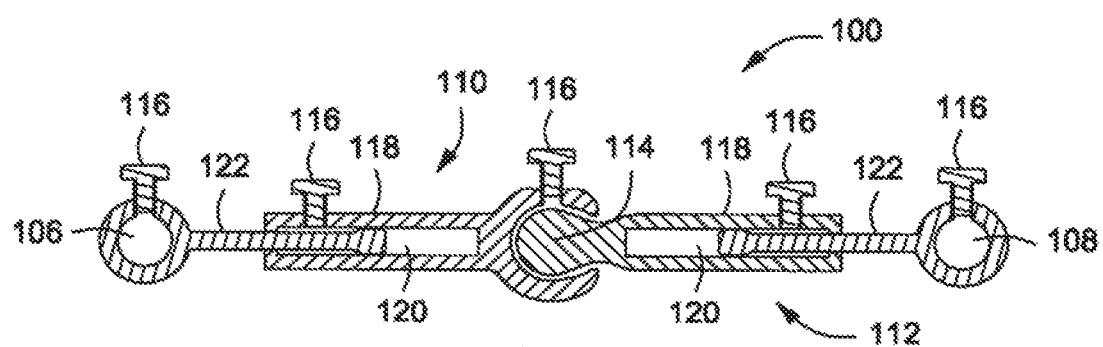
FIG. 9 is a cross-sectional side view of one embodiment of the rod link reducer 100 of the present invention.

FIG. 9 is a cross-sectional side view of one embodiment of the rod link reducer 10 present invention, shown in this embodiment with screws 116. The skilled artisan will recognize that the screws 16 provide reversible mechanical fixation between the different parts of the system that can be tightened and loosened during spinal adjustments. Any given joint may include some friction or resistance during use up to and including total fixation. The screws 116 can be replaced or include pins, set screws, cotter pins, internal or external compression, compression fittings, collared fittings, screw-drives or even electrical, pneumatic or hydraulic movement or pressure. In the embodiment depicted, first and second translatable transverse shafts 110, 112 as shown as adjustment sleeves slidably fitted within a housing 118 is an axial bore 120 and within the axial bore a strut 122 in which the screw 116 serves as a fastener positioned to secure the strut 122 within the housing 118, wherein the struts 112 allow for coarse longitudinal movement of the strut 122 with respect to the strut housing 118. The skilled artisan will recognize that the strut-bore configuration can be reversed (bore-strut) or replaced with side-by-side struts, internal-external slidable pins within a groove, screw-drives, magnetic drives, electrical, pneumatic or hydraulic drives so long as the translatable transverse shafts 110, 112 permit the user to expand and/or contract one or both the translatable transverse shafts 110, 112.

Figure 10:
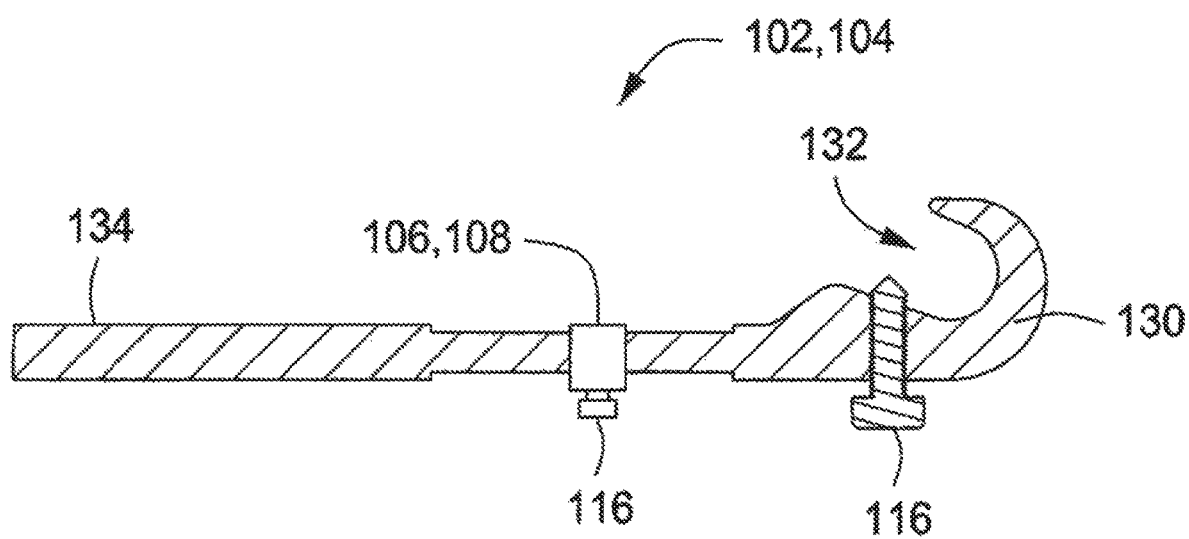
FIG. 10 is a side view of one embodiment of a rod manipulator.

FIG. 10 is a side view of one embodiment of rod manipulators 102, 104. In this side view, screws 116 are shown as well as either first or second joint 106, 108. The rod manipulators 102, 104 include a head 130 that has an opening 132 that first a rod (temporary or permanent) for spinal fixation. The screw 116 is used to engage and retain the rod. The rod manipulators 102, 104 are comprised of a material with sufficient tensile strength to allow the manipulator to fasten to the rod but also to permit the user to translate movement from the handle 134 into the rod in any direction. The handle 134 may itself also include a coating (not depicted) to improve the grip of a user during use or may be shaped to permit a second handle to attach to the handle 134 to increase the leverage of a user when manipulating a spine during spinal fixation surgery. Again, while this embodiment is shown with screws, any fastening method (pins, set-screws, compression, collets, etc.) may be used to fasten the various components of the rod link reducer of the present invention.

The rod link reducer 100 may be used in conjunction with existing spinal screw and rod fixation systems or may be used in conjunction with the pedicle screw 10. The size and thickness of rods may be varied depending on the type of surgery, tensile strength required and preference of the user.

FIG. 11 shows the first step in a spinal fixation process. In this embodiment, a temporary rod 34 has been attached to pedicle screws 10 (while not depicted, the pedicle screws may be attached individual vertebra. Examples of conditions that may be treated using the present invention include kyphosis, lordosis, scoliosis or combinations thereof. A rod link reducer 100 is shown connected to the temporary rod 34 and the spine (not shown) has been aligned. In FIG. 12, the permanent rod 36 is introduced into the pedicle screw 10 while the rod link reducer 110 holds the entire assembly in place while the permanent rod is permanently affixed to the pedicle screws 10. Finally, FIG. 13 shows the final spinal rod assembly after removing the temporary rod and the breakable tabs from the pedicle screws 10.

FIG. 14 shows the advantage provided by the rod link reducer 100 of the present invention. In this top view of the operation of the present invention, two rod link reducers 100a, 100b are connected to two pairs of temporary rods 34a-d and pedicle screws 10a-h. By compressing, distracting or rotating the rod link reducers 100a, 100b, the user can manipulate the spine in all directions necessary for spinal alignment and fixation. Furthermore, the user is able to compress, distract, and translate any of the spinal segments until arriving at a final position. The rod link reducer 100 is tightened upon final positioning and the permanent rod can be inserted into the pedicle screws. Furthermore, the rod link reducers 100a, 100b can be tightened in a single plane at a time while still manipulating the rest of the spine in the other planes.

The present invention can be used to correct mild to severe spinal deformities, including sever deformities. The present invention includes the following advantages: a reduced risk of intraoperative mishaps due to the instability caused by exchanging the temporary rods with the permanent rod, it increases the directions in which the deformities can be corrected and reduces the number of tools, and surgical time caused by temporary rod failure or slipping that occurs between the final positioning of the temporary rods and the fixation of the permanent rod. It has been found that the present invention allows the surgeon to shorten the duration of the operation and also increases the extent of correction in a single procedure.

Figure 15:
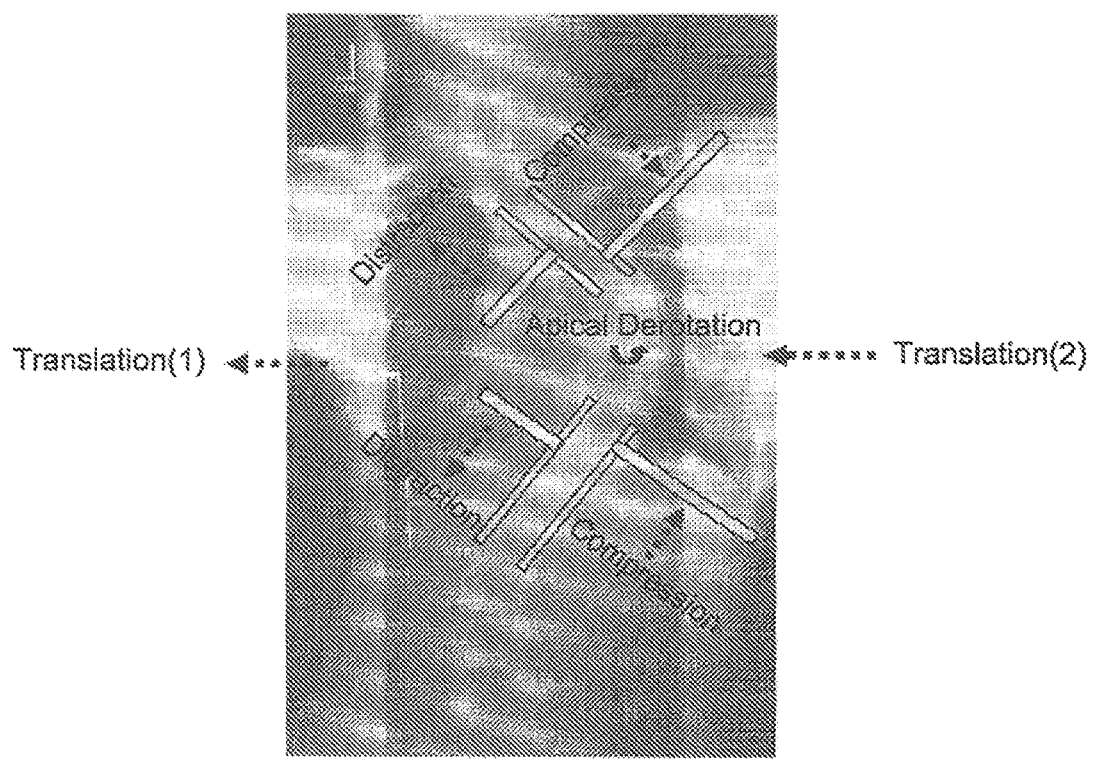
FIG. 15 shows an overlay of the planning and tools for a surgical procedure to correct a severe spinal deformity.

FIG. 15 shows an overlay of the planning and tools for a surgical procedure to correct a severe spinal deformity. An x-ray is shown of a malformed spine and the tools are overlaid to plan the positioning of the pedicle screws, rods and rod link reducer. Next, the user determines the various different steps in the correction, including the compression, distraction, apical derotation and translation of one or both pairs of temporary rods. Also shown are optional tools or handles to increase the leverage of the surgeon, taking into account the accessibility of tools due to the translation and rotation of the underlying spine prior to treatment. In certain cases, the steps may be alternated to maximize the leverage of the rod link reducers in different direction, thereby maximizing efficiency of the movement, increasing the effectiveness of the procedure and minimizing the time of the procedure.

Figure 16A:
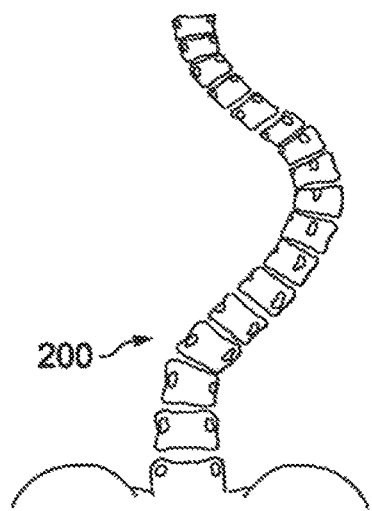
FIGS. 16A-16E show a procedure that includes distraction, translation and apical derotation for correction of a single severe spinal curve.
Figure 16B:
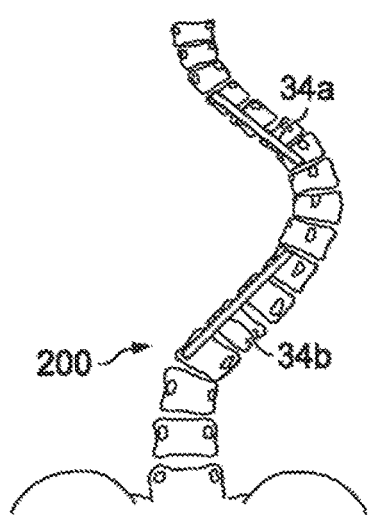
Figure 16C:
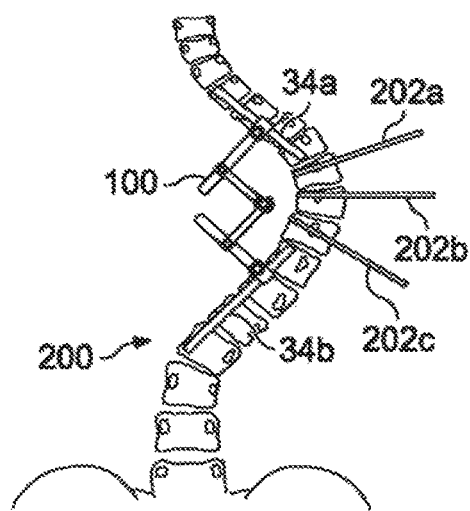
Figure 16D:
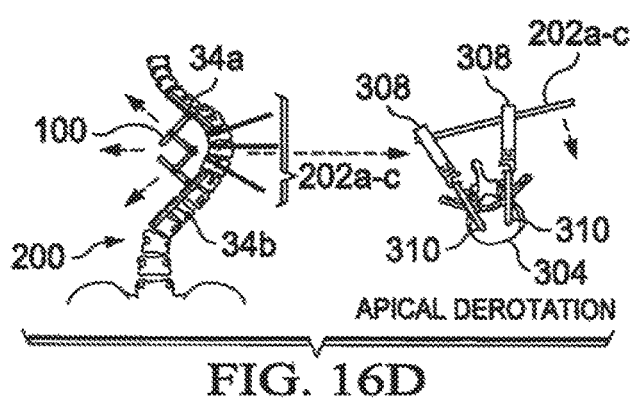
Figure 16E:
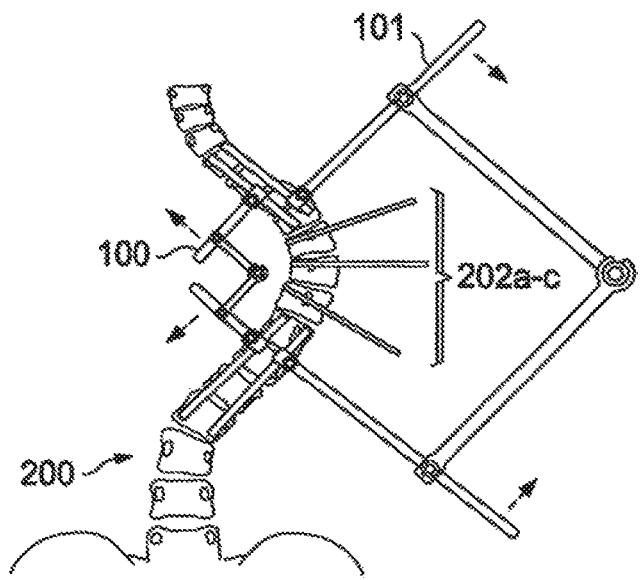

FIGS. 16A to 16E shows a procedure of the present invention that includes distraction, translation and apical derotation. FIG. 16A shows a single right thoracic rigid curve 200. FIG. 16B shows the first step in the procedure in which temporary rods 34a and 34b, which are fixed at a proximal portion of the spine and another one fixed at distal portion of the curve about a concavity. The temporary rods 34a, 34b are attached to the single right thoracic rigid curve 200 using pedicle screws (not depicted) on either end of the site for distraction, translation and apical derotation. One example of the pedicle screws that may be used in the procedure is pedicle screw 10. FIG. 16C shows the rod link reducer 100 connected to temporary rods 34a and 34b on the concavity. Next, derotation instruments 202a-c are attached to the apical vertebrae. FIG. 16D shows the combined distraction, translation and apical derotation of the spine in which the rod link reducer 100 is used for the distraction and translation (arrows) and the derotation instruments 202a-c, seen as a cross-sectional view of the spine at a vertebrae 304, are used alone or in combination (in this instance) for apical derotation via linker 308 attached to pedicle screws 310. The skilled artisan will recognize that these tools may be used for a distraction, translation and/or apical rotation, however, most procedures will involve combinations of these manipulations. FIG. 16E shows a variation of the combined distraction, translation and apical derotation outlined in FIGS. 16A-16D in which pairs of temporary rods 34a, 34b are shown in parallel along the proximal and distal segments of the spine. A second rod link reducer 101 is shown as two provisional rods 34 are on the concavity. Convex provisional compression is to help the curve correction.

Figure 17A:
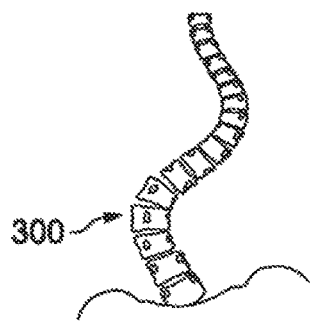
FIGS. 17A-17E show a procedure for correction of a double major severe spinal curve (Thoracic and Lumbar curve).
Figure 17B:
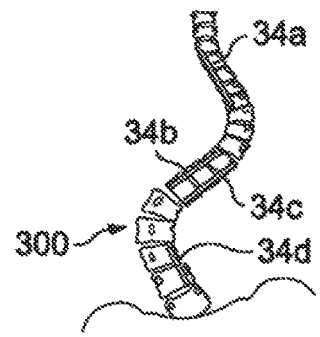
Figure 17C:
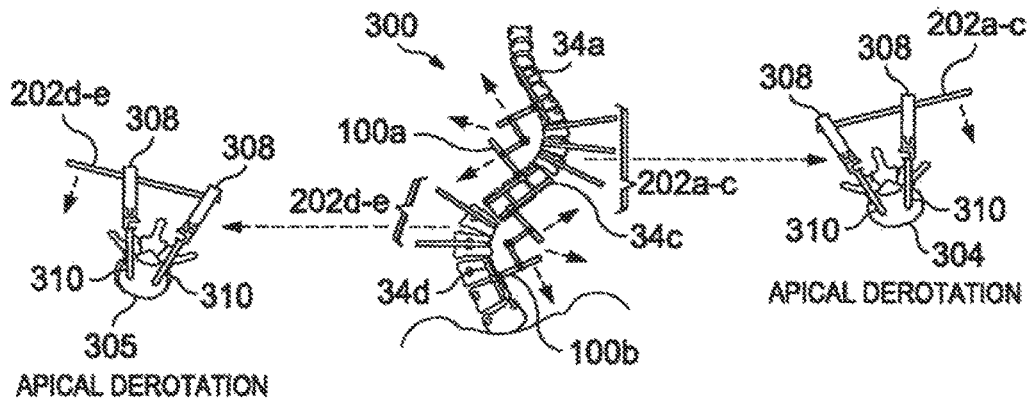
Figure 17D:
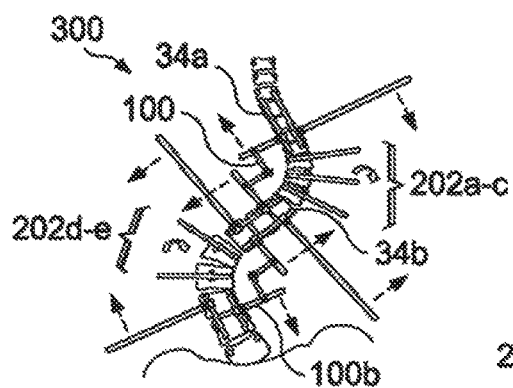
Figure 17E:
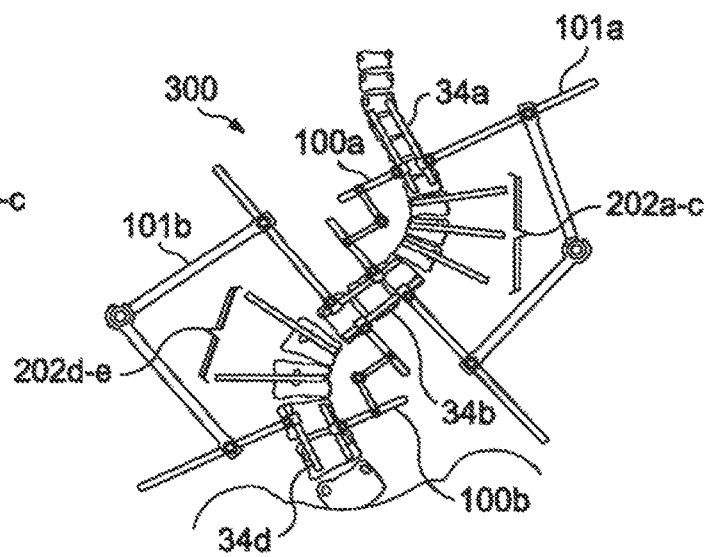

FIGS. 17A to 17E shows the use of the rod link reducer 100 on a spinal convexity. FIG. 17A shows a double major rigid curve 300 onto which two temporary rods 34a, 34b are on the concavity of the thoracic curve and two temporary rods 34c, 34d are on the concavity of the lumbar curve. FIG. 17C shows the attachment of two rod-link reducers 100 fixed on the concavity for both curves, respectively. Next, the combined distraction, translation and apical derotation for both curves is depicted in which derotation instruments 202a-c and 202d-e are attached to the vertebrae 304, 305 through pedicle screws 306 via linkers 308. The linkers 308 serve as attachment points for the derotation instruments 202a-e and can be used to increase the leverage for the distraction, translation and apical derotation. FIG. 17E shows the positioning of a pair of convex temporary rods at each site used for compression maneuvers to help in the correction of the two curves using two rod link reducer 100, 101 about each of the treatment sites.

Figure 18:
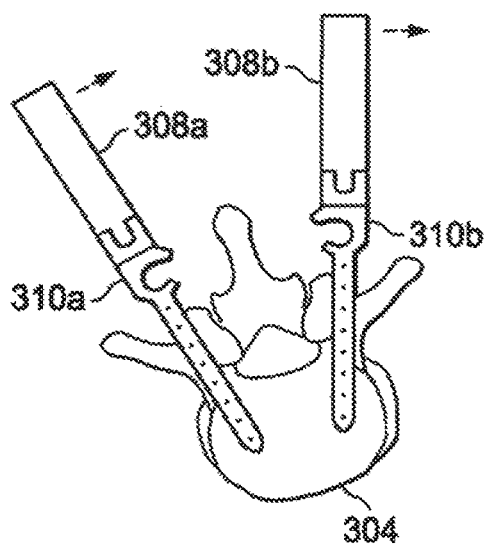
FIG. 18 is a detailed view of one embodiment of an apical derotation without linking the two pedicle screws.

FIG. 18 is a detailed view of one embodiment of an apical derotation without linking the two pedicle screws 310a,b. In this embodiment, the linkers 308a,b are used directly to aid in the apical rotation of a single vertebrae 304 without a linked derotation instrument.

Figure 19:
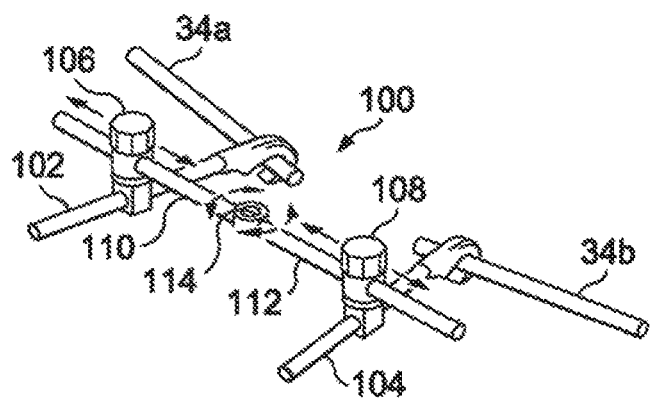
FIG. 19 is an isometric view of a design of the rod-link reducer of the present invention.
Figure 20:
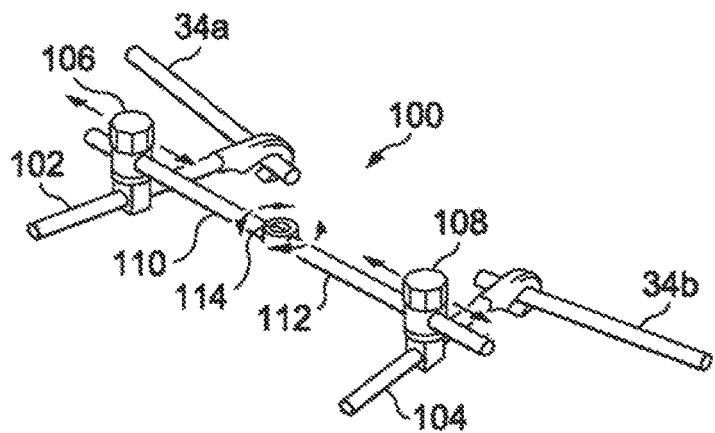
FIG. 20 is an isometric view of another design of the rod-link reducer of the present invention.
Figure 21:
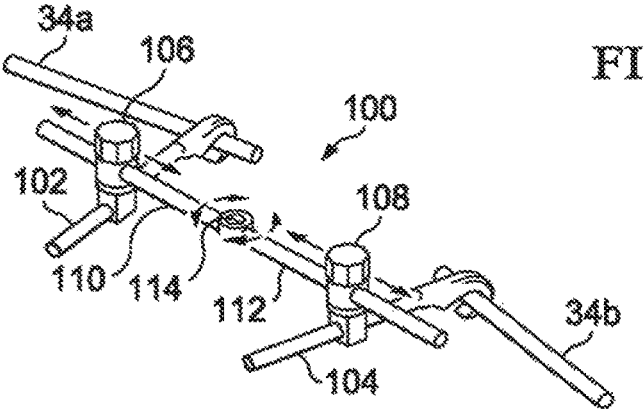
FIG. 21 is an isometric view of another design of the rod-link reducer of the present invention.

FIGS. 19, 20 and 21 shows various designs of the rod-link reducer 100. FIG. 19 shows a rod link reducer 100 that includes a universal connecter on the central portion. The rod link reducer 100 includes first and second spinal rod manipulators 102, 104, which are connected to a first spinal rod manipulator joint 106 connected to the first spinal rod manipulator 102 and a second spinal rod manipulator joint 108 connected to the second spinal rod manipulator 104. First and second translatable transverse shafts 110, 112 slides through joints 106, 108, respectively. The joints 106, 108 can tighten to fix the transverse shafts 110, 112 individually. In FIG. 19, the two translatable transverse shafts 110, 112 have movement around a reducer 114, which is depicted as a single reducer with universal movement. In one example, the reducer 114 may be fixed to act as a straight rod to limit the movement of the first and second spinal rod manipulators 102, 104 in two planes. FIGS. 20 and 21 show the rotation between the rod-connecter. This design is stronger and easy to install, and give surgeons more freedom during surgery.

As the skilled artisan will appreciate, the first and second translatable transverse shafts 110, 112 may be in-line, as depicted in FIGS. 19-21, or may be parallel on two separate planes allowing the first and second translatable transverse shafts to extend past the ends of the opposite shaft. By allowing the first and second translatable transverse shafts to move in parallel, the distance between first and second spinal rod manipulators 102, 104 can be reduced to a minimum in certain manipulations. As can also be seen from these figures, the first and second rod manipulator joints 106, 108 can slide toward or away from the temporary rods 34a,b. The configuration presented herein allows six degrees of freedom in any direction, while also providing the necessary strength and leverage to perform complex spinal deformity surgery in a reduced space.

Figure 22C:
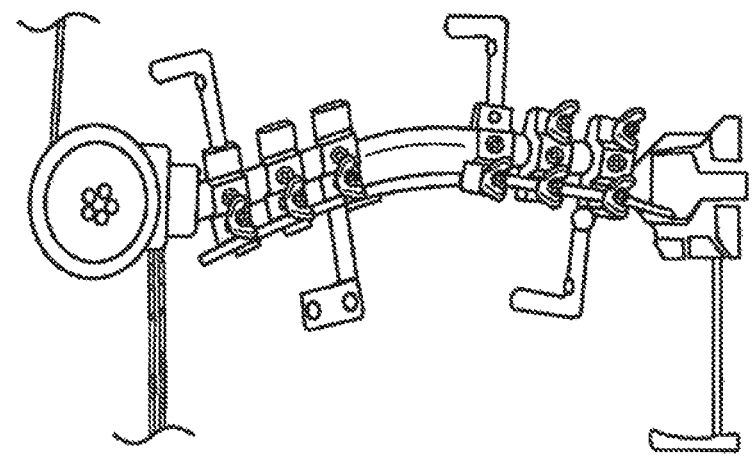
FIGS. 22A-22C show a six-segment plastic spine model which was instrumented to test three constructs: (A) temporary rod/apical rod-link reducer (left panel); (B) provisional rod (center panel); and (C) final rod (right panel).
Figure 22B:
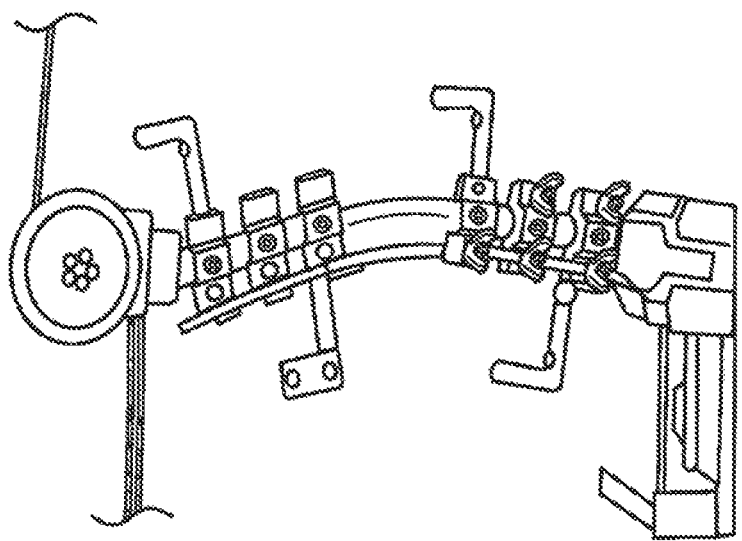
Figure 22A:
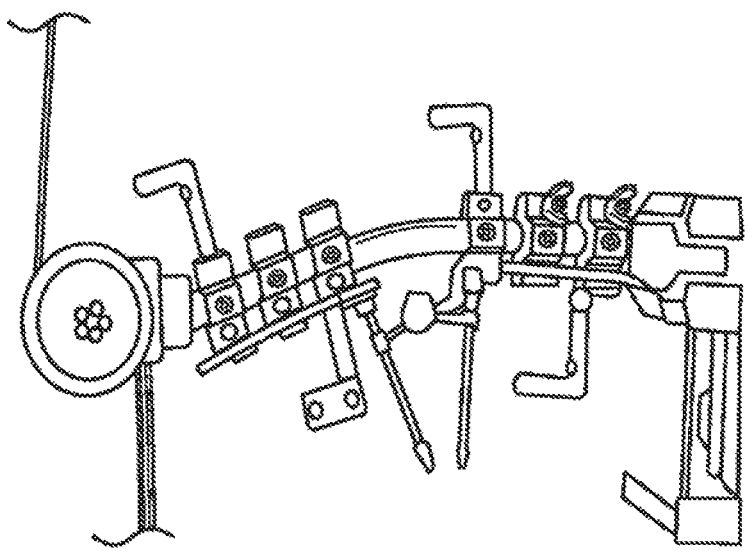

FIG. 22A to 22C shows the new pedicle screw and apical rod-link reducer posterior instrumentation system that includes: (A) pedicle screw with a screw head that can receive two 5.5-mm rods (provisional and final rods) with a breakaway mechanism between the two rod-receivers; and (B) a rod-link reducer rigidly linking the provisional rods at the apex, allowing attachment to the rod at any orientation so as to easily make compression, distraction, derotation and cantilever maneuver. While the deformity is corrected using the provisional rod/rod-link reducer, the final rod is fixed and then the provisional ones are removed. A six-segment plastic spine model was instrumented to model three constructs: (A) provisional rod/apical rod-link reducer; (B) provisional rod;

and (C) final rod. The spines were tested using pure bending motions. Segmental range of motion (ROM) was recorded using a three-dimensional motion analysis system.

Figure 23:
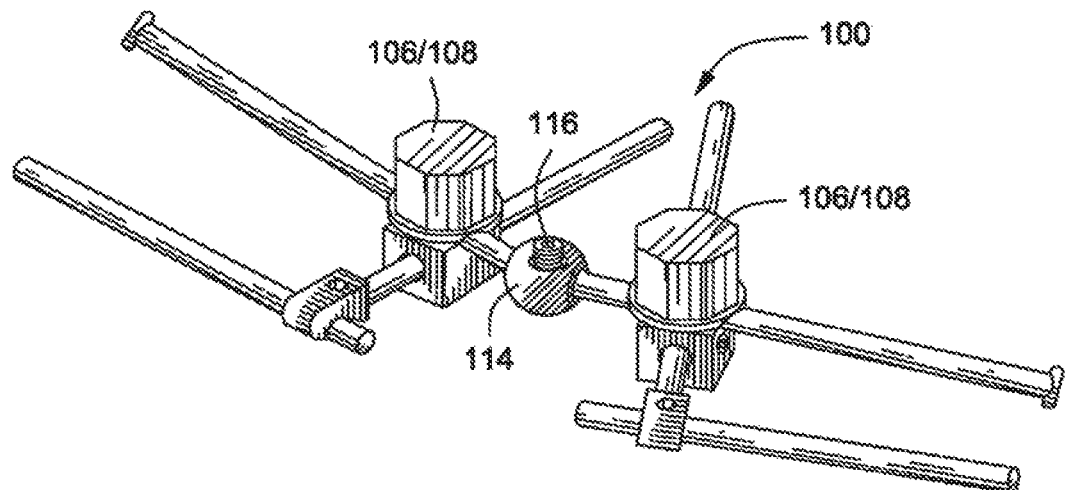
FIG. 23 is a picture that illustrates a perspective view of a rod-link reducer which links and locks the provisional rods on the concavity.
Figure 24:
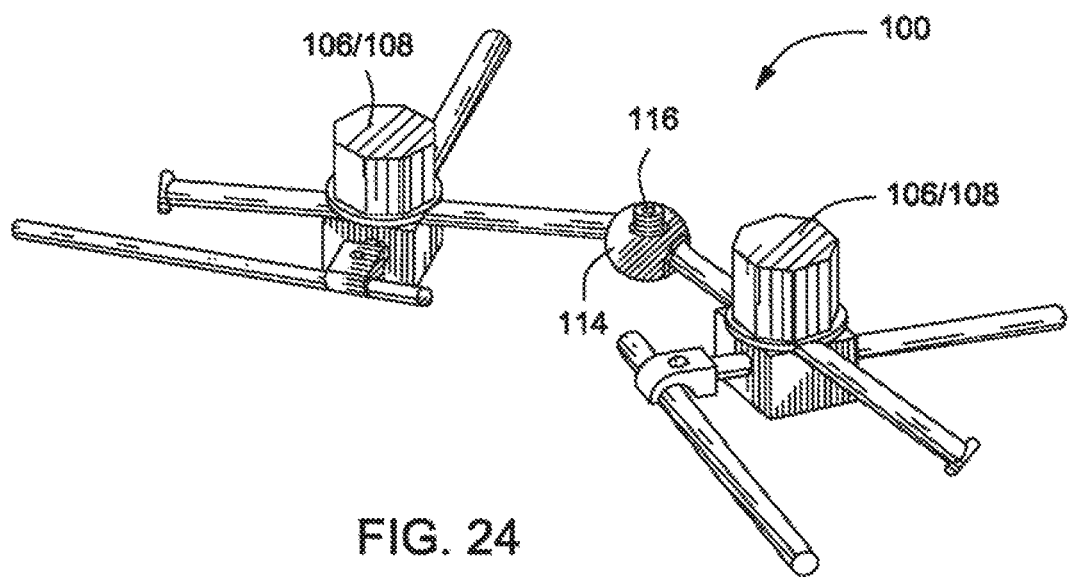
FIG. 24 is a picture that illustrates a perspective view of a rod-link reducer which links and locks the provisional rods on the convexity.

FIG. 23 is a drawing illustrating a perspective view of the rod-link reducer 100 which links and locks the first and second translatable transverse shafts 110, 112. The reducer 114 provides a mechanism to rotate the device on the concavity. For example, the reducer 114 can have a ball bearing like mechanism controlled by the screw 116 as seen in FIG. 23. FIG. 24 is a drawing illustrating a perspective view of the rod-link reducer 100 which links and locks the first and second translatable transverse shafts 110,112. The reducer 114 provides a mechanism to rotate the device on the convexity.

Figure 25:
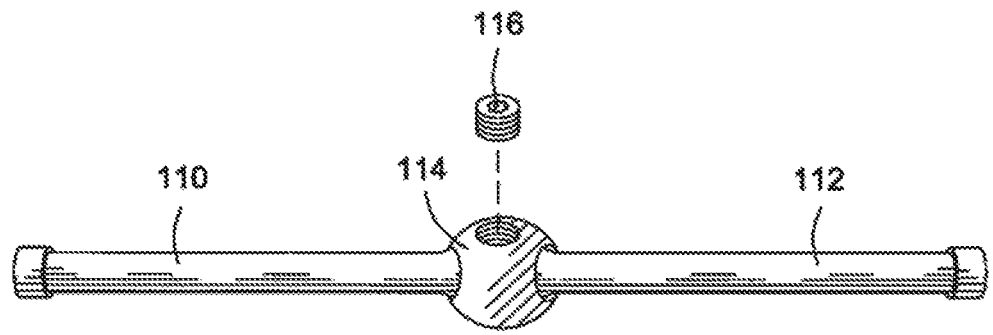
FIGS. 25-26 are pictures illustrating a perspective view of the parts of the rod-link reducer.
Figure 26:
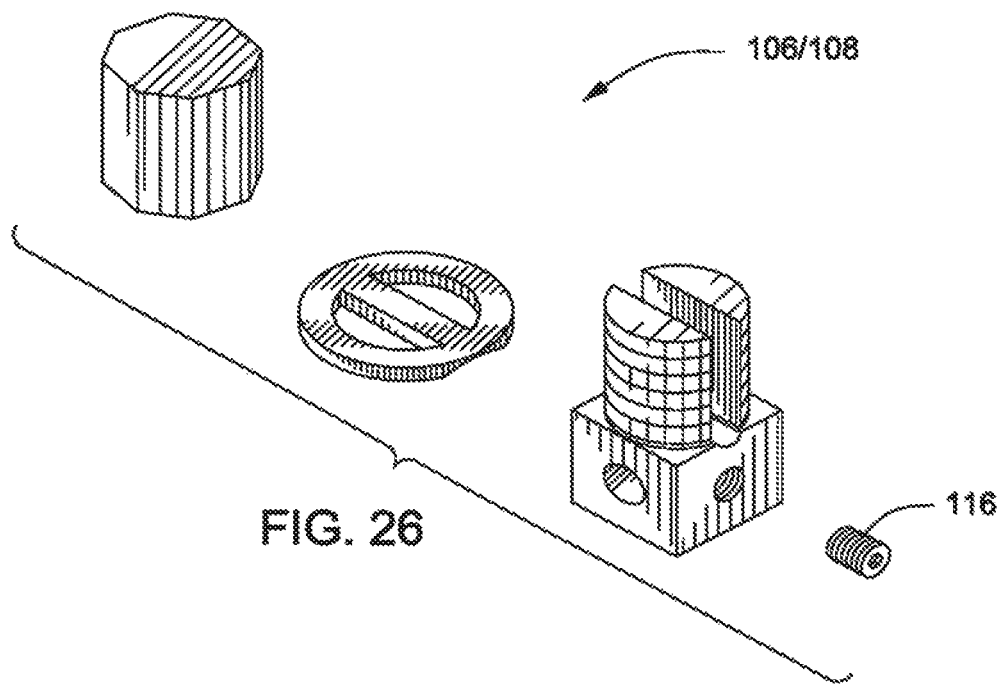

FIGS. 25 and 26 are diagrams illustrating perspective views of the parts of the rod-link reducer 100. Specifically, FIG. 25 shows the first and second translatable transverse shafts 110,112, and the reducer 114 and the screw 116. FIG. 26 shows the parts of the either first or second joint 106,108.

FIG. 27 is a diagram showing the combination of parts from FIGS. 25 and 26 with the first and second translatable transverse shafts 110,112, reducer 114, the screw 116, and either first or second joint 106,108.

FIG. 28 is a diagram similar to FIG. 10 with a side view of one embodiment of rod manipulators 102,104. In this side view screws 116 are shown as well as either first or second joint 106,108. The rod manipulators 102,104 include a head 130 that has an opening 132 that first a rod (temporary or permanent) for spinal fixation. The screw 116 is used to engage and retain the rod. In particular, the cross sections of the either first or second joint 106,108 are shown.

Figure 29:
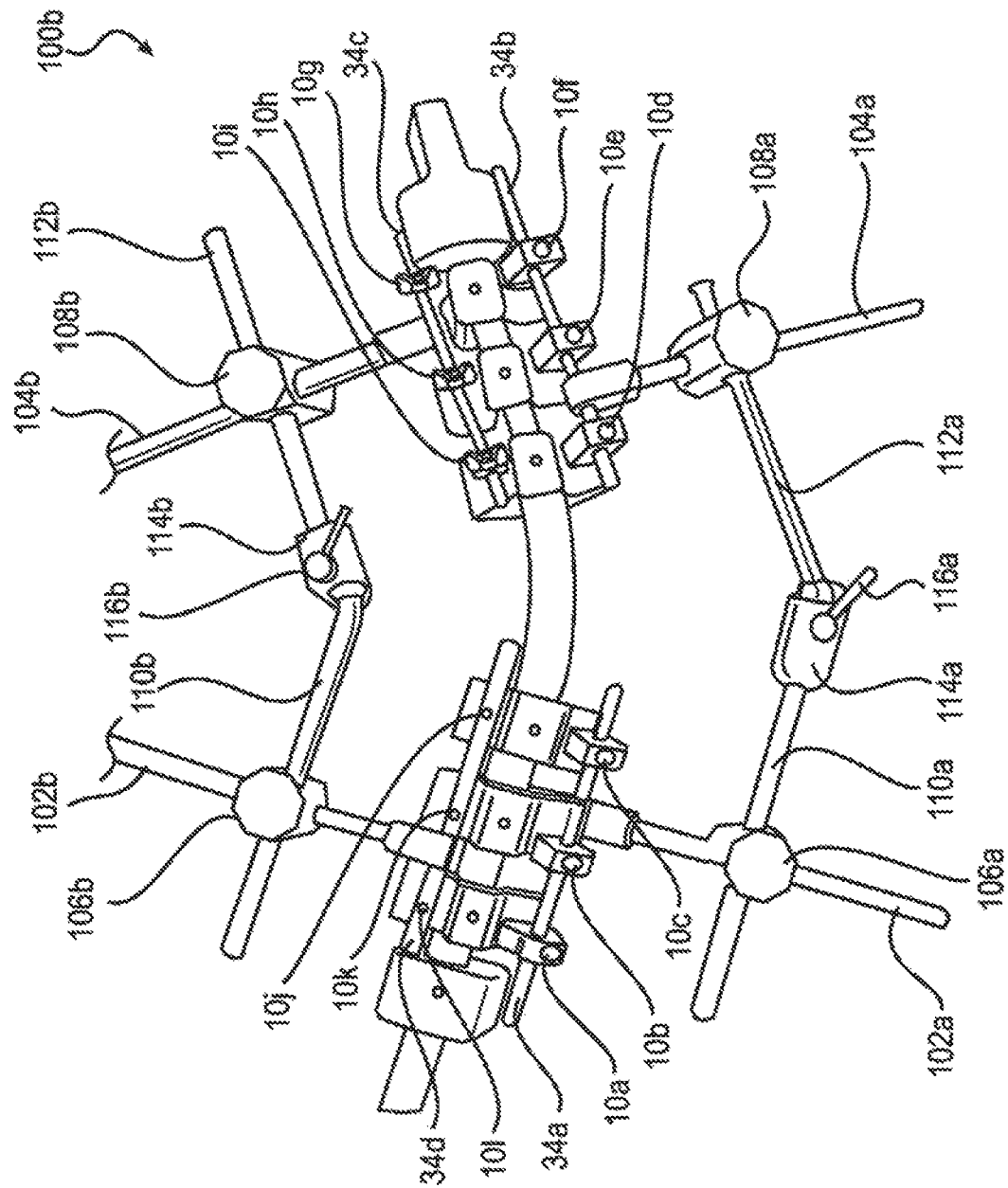
FIG. 29 is an image that shows the pedicle screws, provisional rods, and two rod-link-reducers which are fixed in a coronal curve deformity model.

FIG. 29 is an image of two rod-link reducers 100a,100b which links and locks the first and second translatable transverse shafts 110a,b and 112a,b. The reducer 114a,b provides a mechanism to rotate the device on the concavity. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d,e,f,g,h,i,j,k,ld affixed to the pedicle screws 10a,b,c,d,e,f,g,h,i,j,k,l in the spine for alignment.

Figure 30:
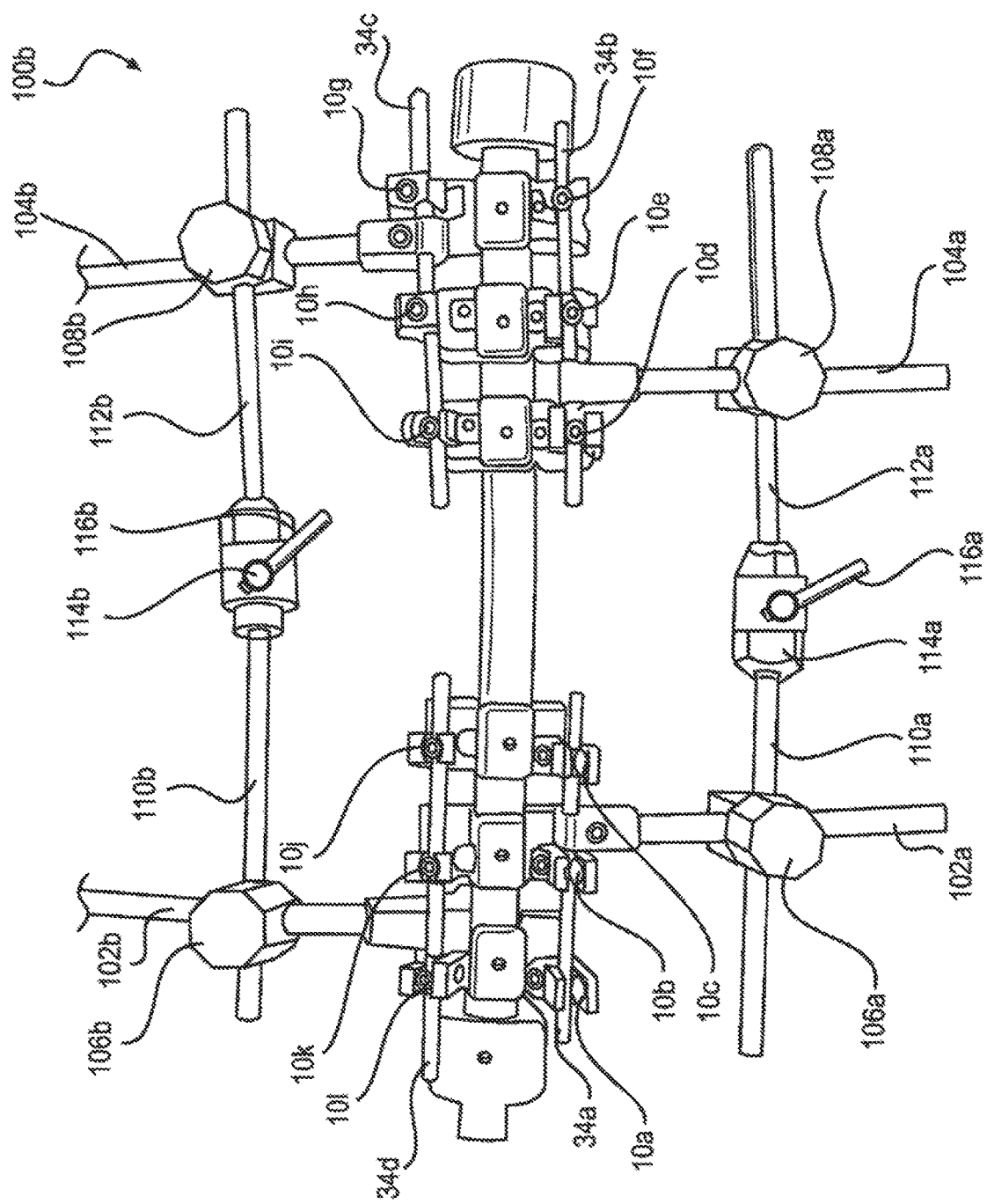
FIG. 30 is an image that shows the rod-link-reducers correcting the coronal curve.

FIG. 30 is an image of two rod-link reducers 100a,b which link and lock the first and second translatable transverse shafts 110a,b and 112a,b showing the reducers correcting the coronal curve. The reducers 114a,b provide a mechanism to rotate the device on the concavity. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d,e,f,g,h,i,j,k,ld affixed to the pedicle screws 10a,b,c,d,e,f,g,h,i,j,k,l in the spine for alignment.

Figure 31:
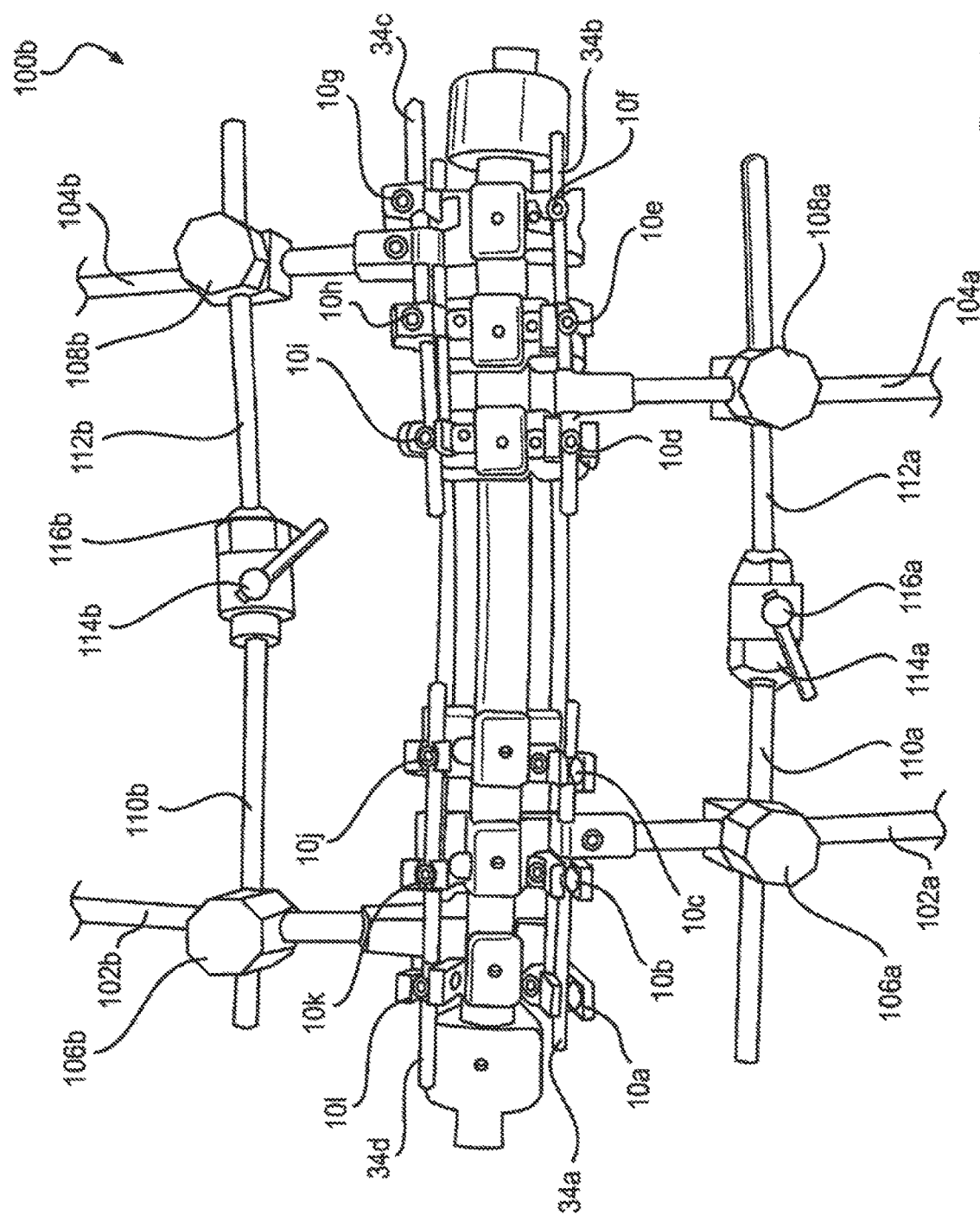
FIG. 31 is an image that shows the provisional rods, the rod-link-reducers, and the final rods with a spine that has been corrected.

FIG. 31 is an image that shows the rod-link-reducers and the provisional rods and the final rods with the spine which is corrected. The reducer 114a,b provides a mechanism to rotate the device on the concavity. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d, e,f,g,h,i,j,k,ld affixed to the pedicle screws 10a,b,c,d,e,f,g,h, i,j,k,l in the spine for alignment. In addition to the temporary rods 34a,b,c,d,e,f,g,h,i,j,k,ld, permanent rods 36a,b are introduced into the pedicle screws 10a,b,c,d,e,f,g,h,i,j,k,l while the rod link reducers 100a,b holds the entire assembly in place. FIG. 31 shows the permanent rods 36a,b with the temporary rods 34a,b,c,d,e,f,g,h,i,j,k,ld and the rod link reducers 100a,b in position.

Figure 32:
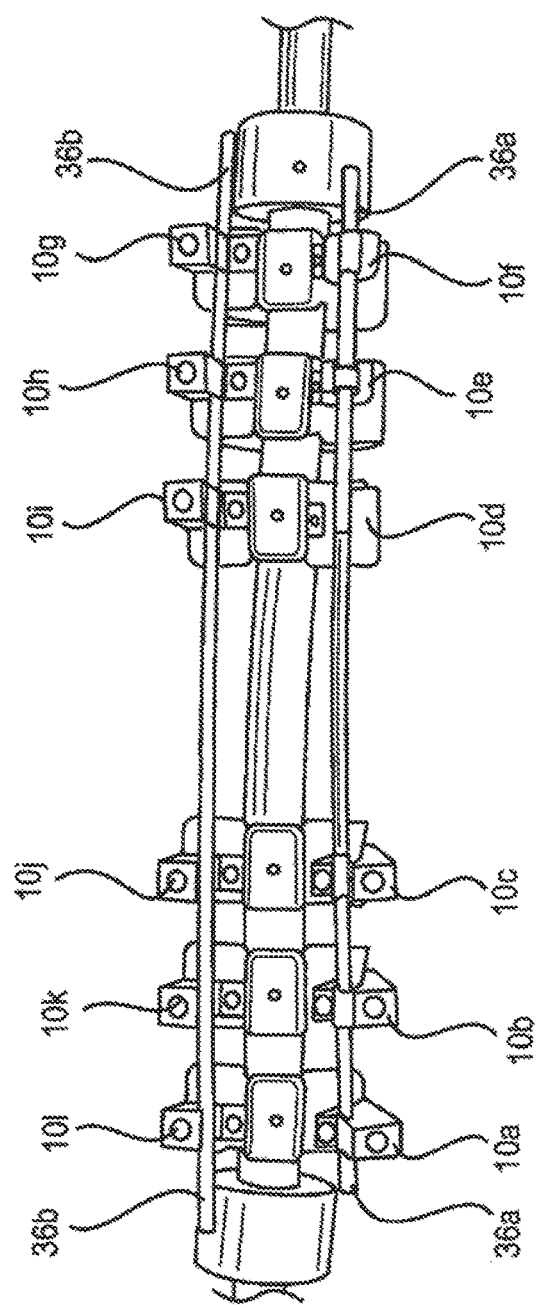
FIG. 32 is an image that shows the final rods with a spine that has been corrected.

FIG. 32 is an image that shows the final rods with the spine which is corrected. FIG. 32, the permanent rods 36a,b are introduced into the pedicle screws 10a,b,c,d,e,f,g,h,i,j,k,l while the rod link reducer (not shown) holds the entire assembly in place while the permanent rods 36a,b are permanently affixed to the pedicle screws 10a,b,c,d,e,f,g,h, i,j,k,l. FIG. 32 shows the final spinal rod assembly after removing the temporary rods (not shown) and the breakable tabs from the pedicle screws 10a,b,c,d,e,f,g,h,i,j,k,l.

Figure 33:
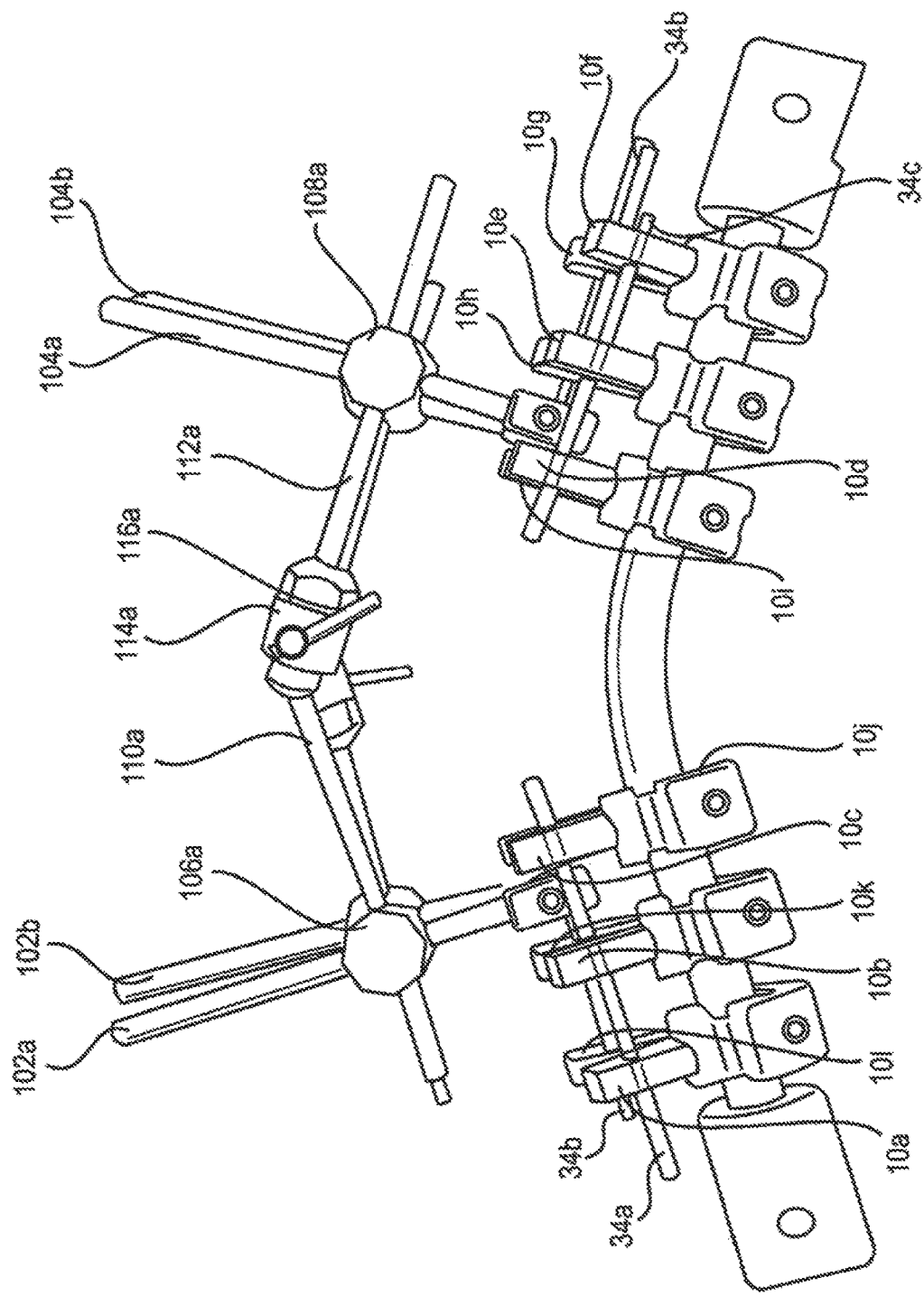
FIG. 33 is an image that shows the rod-link-reducers to correct the sagittal curve to the normal kyphosis.

FIG. 33 is an image that shows the rod-link-reducers correct the sagittal curve to the normal kyphosis. The reducer 114a,b provides a mechanism to rotate the device. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d,e,f,g,h,i,j,k,ld affixed to the pedicle screws 10a,b,c,d,e,f,g,h,i,j,k,l in the spine for alignment.

Figure 34:
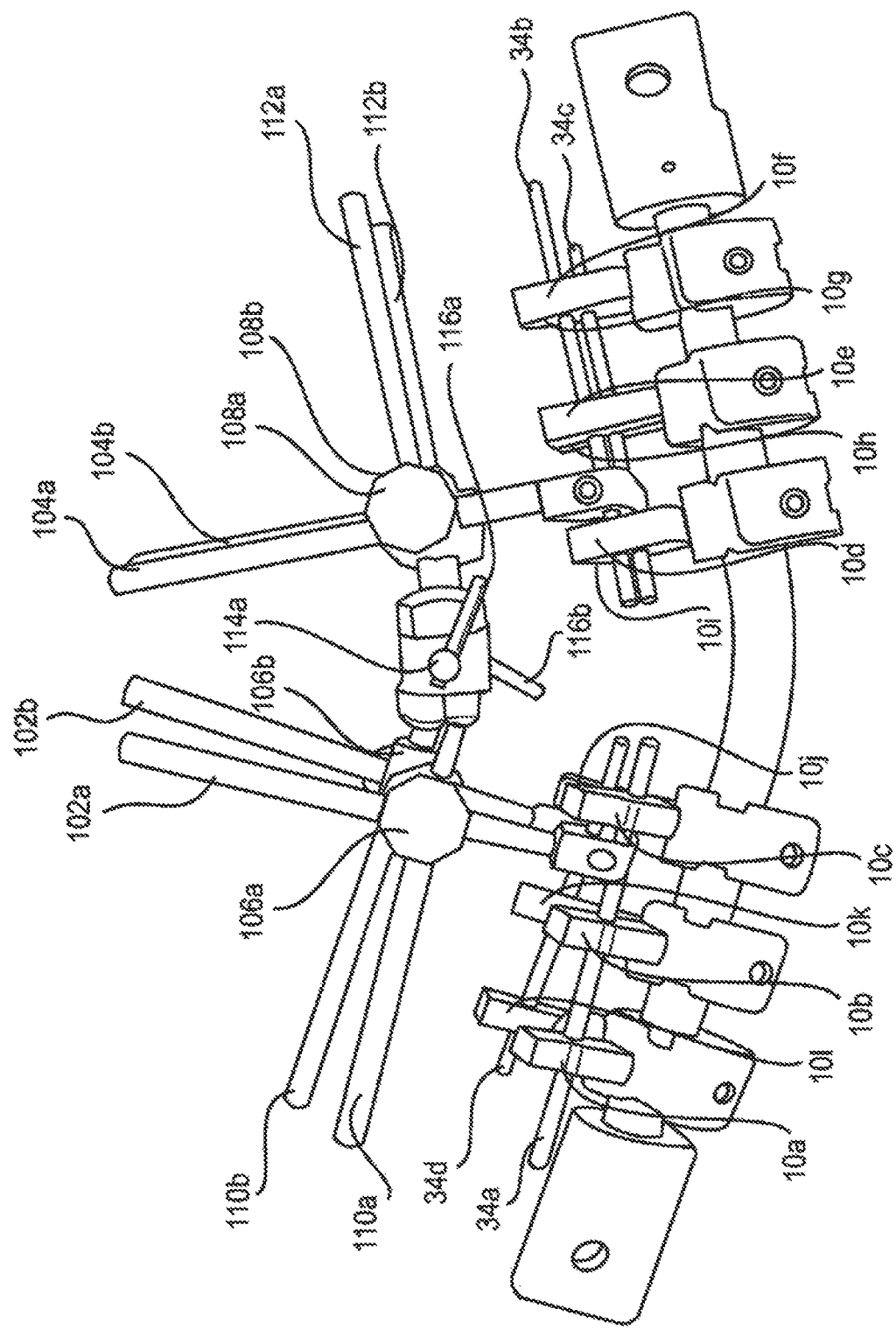
FIG. 34 is an image that shows the rod-link-reducers to correct the sagittal curve to the normal lordosis.

FIG. 34 is an image that shows the rod-link-reducers correct the sagittal curve to the normal lordosis. The reducer 114a,b provides a mechanism to rotate the device. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d,e,f,g,h,i,j,k,l d affixed to the pedicle screws 10a,b,c,d,e,f,g,h,i,j,k,l in the spine for alignment. The skilled artisan will recognize that the instant invention may be used to correct all forms of alignments including kyphosis and lordosis.

Figure 35:
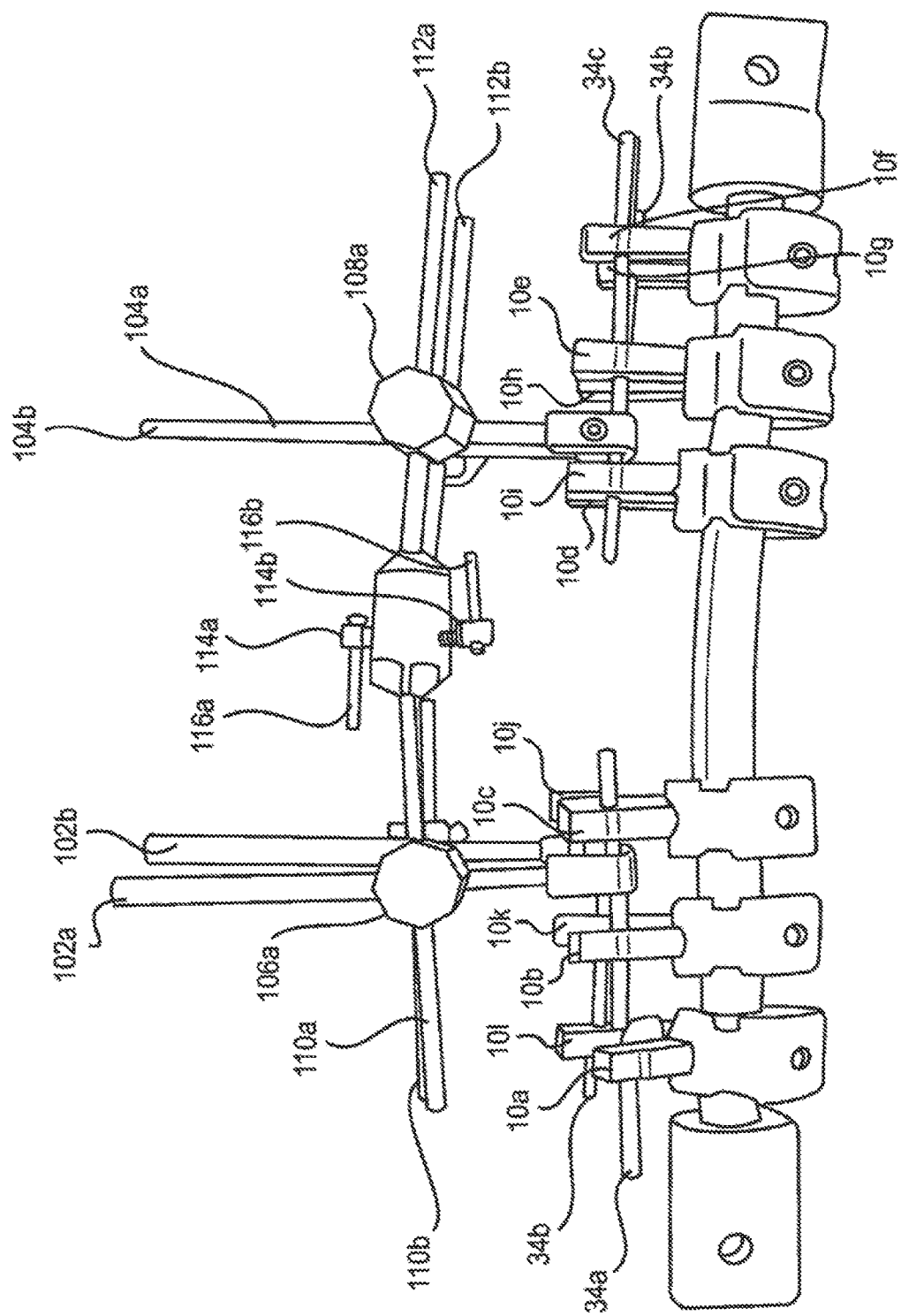
FIG. 35 is an image that shows the pedicle screws, provisional rods, and two rod-link-reducers fixed in a sagittal curve deformity model.

FIG. 35 is an image that shows the pedicle screws, provisional rods, and two rod-link-reducers are fixed in a sagittal curve deformity model. The reducer 114a,b provides a mechanism to rotate the device. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d, e,f,g,h,i,j,k,l d affixed to the pedicle screws 10a,b,c,d,e,f,g,h, i,j,k,l in the spine for alignment.

Figure 36:
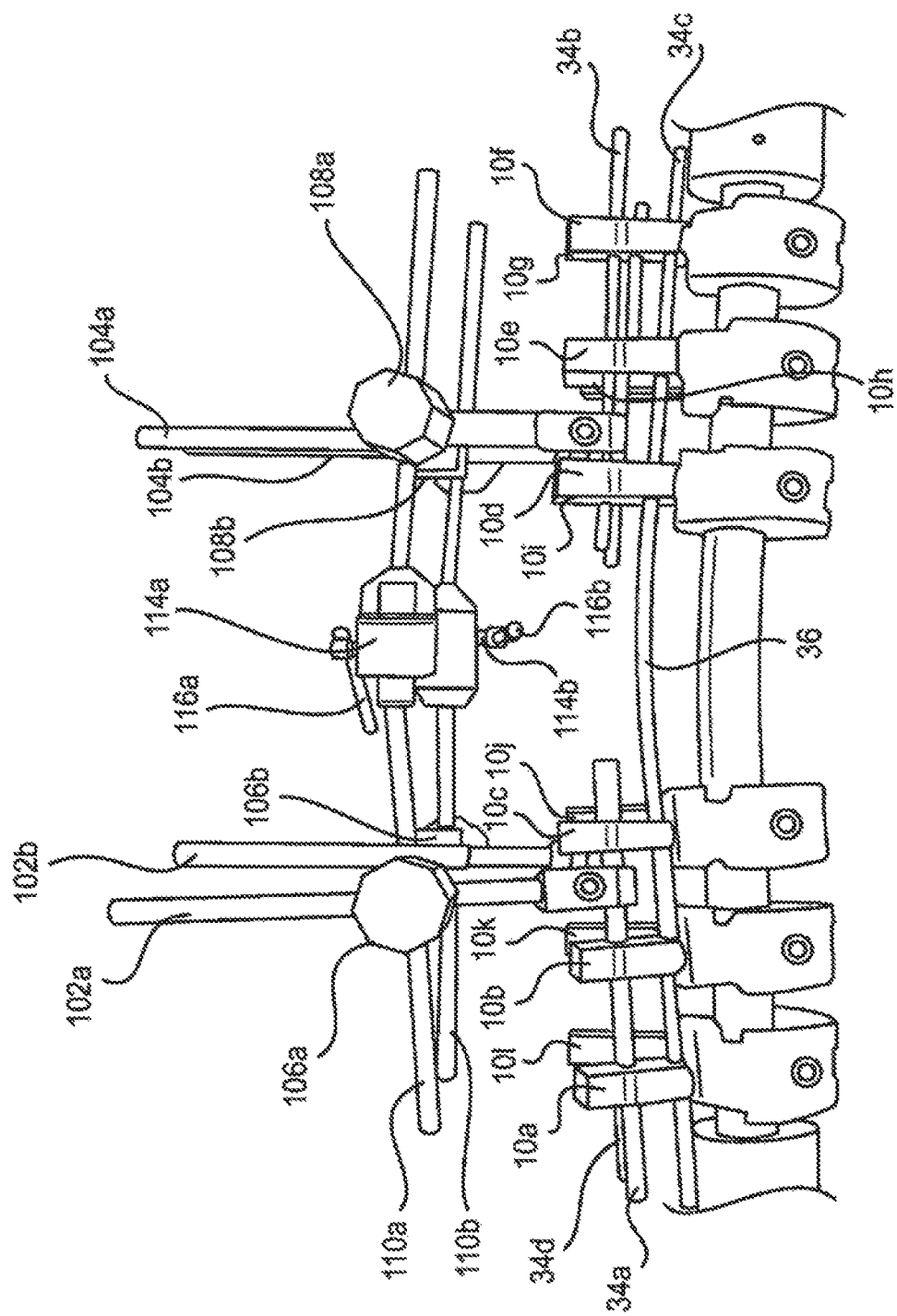
FIG. 36 is an image that shows the final rod insertion after the sagittal curve correction.

FIG. 36 is an image that shows the final rod insertion after the sagittal curve correction. FIG. 36 is an image that shows the rod-link-reducers and the provisional rods and the final rods with the spine which is corrected. The reducer 114a,b provides a mechanism to rotate the device on the concavity. For example, the reducer 114 can have a ball bearing like mechanism controlled by the screw 116a,b. The rod link reducer 100a,b includes first and second spinal rod manipulators 102a,b and 104a,b, which are connected to a first spinal rod manipulator joint 106a,b connected to the first spinal rod manipulator 102a,b and a second spinal rod manipulator joint 108a,b connected to the second spinal rod manipulator 104a,b. First and second translatable transverse shafts 110a,b, 112a,b slides through joints 106a,b, 108a,b, respectively. The joints 106a,b and 108a,b can tighten to fix the transverse shafts 110a,b and 112a,b individually. The two translatable transverse shafts 110a,b, 112a,b have movement around the reducer 114a,b, which is depicted as a single reducer with universal movement. The first and second spinal rod manipulators 102a,b and 104a,b are connected to the temporary rods 34a,b,c,d affixed to the pedicle screws 10a,b,c,d,e,f,g,h,i,j,k,l in the spine for alignment. In addition to the temporary rods 34a,b,c,d, permanent rod 36 are introduced into the pedicle screws 10a,b,c,d,e,f, g,h,i,j,k,l while the rod link reducers 100a,b holds the entire assembly in place. FIG. 36 shows the permanent rod 36 with the temporary rods 34a,b,c,d and the rod link reducers 100a,b in position.

Figure 37:
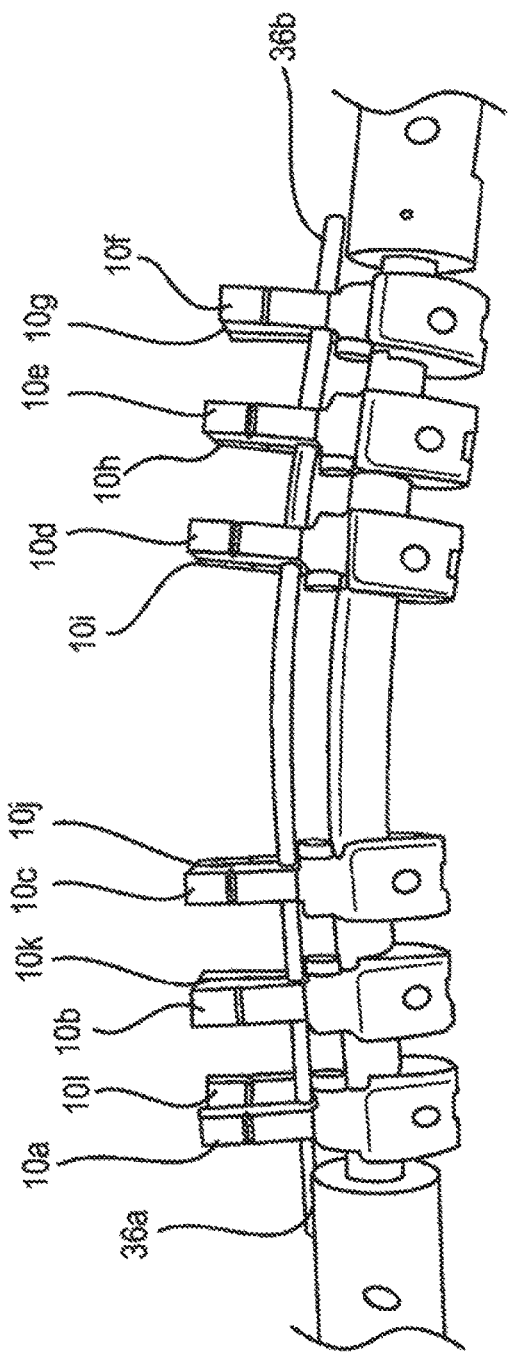
FIG. 37 is an image that shows the final rods with a spine that has been corrected.

FIG. 37 is an image that shows the final rods are with the spine which is corrected. FIG. 37, the permanent rod 36 are introduced into the pedicle screws 10a,b,c,d,e,f,g,h,i,j,k,l while the rod link reducer (not shown) holds the entire assembly in place while the permanent rod 36 are permanently affixed to the pedicle screws 10a,b,c,d,e,f,g,h,i,j,k,l. FIG. 37 shows the final spinal rod assembly after removing the temporary rods (not shown) and the breakable tabs from the pedicle screws 10a,b,c,d,e,f,g,h,i,j,k,l.

It was found that while using the present invention, there were no significant differences in the ROM between the three constructs except right lateral bending in which the provisional rod/rod-link and the provisional rod constructs ROM were greater than the final rod construct (P=0.005) (Table 1).

TABLE 1

Range of Motion (Degree) in the Three Constructs

| | Provisional Rod + Rod Link | Provisional Rod | Final Rod |
|---|---|---|---|
| Flexion | 4.3 ± 1.7 | 3.1 ± 0.2 | 3.2 ± 0.5 |
| Extension | 1.3 ± 0.1 | 1.2 ± 0.3 | 1.8 ± 0.6 |
| Left Lateral Bending | 1.8 ± 0.8 | 1.9 ± 1 | 2.1 ± 0.6 |
| Right Lateral Bending* | 2.2 ± 0.3 | 2.3 ± 0.5 | 1.6 ± 0.1 |

*ANOVA P-Value = 0.005, Provisional Rod + Rod Link and Provisional Rod Construct ROM > Final Rod Construct.

The provisional rod/rod-link reducer construct provided similar stiffness and stability compared to the provisional and final rod constructs. This new system offers a safer, easier and improved deformity correction, as well as shorter surgical time for the PVCR of the severe spinal deformity.

The novel pedicle screw/rod-link reducer offers better maintenance of spinal stability throughout the surgical procedure to reduce risk of the spinal cord injuries. This system therefore provides a safer, easier and improved deformity correction, as well as shorter surgical time for the PVCR of the severe spinal deformity.

The present invention overcomes the following disadvantages of existing systems, namely, the limitation for the apical vertebral derotation and translation. Another disadvantage of existing systems is the difficulty for concave rod derotation and/or translation which result in pedicle screw loosening with damage to the spinal cord. The present invention overcomes both of these advantages by providing a stable, sturdy platform for use of temporary and permanent rods using a single pedicle screw. The pedicle screw of the present invention maximizes the structural-mechanical properties of each fixation point (the lower versus the upper rod coupling) for each specific type of rod (permanent or temporary) while at the same time maximizing the efficiency of the surgical procedure with less tools and equipment. Furthermore, surgeons are already familiar with similar tools and fasteners and do not need to learn new procedures, techniques or the use of new tools.

The present invention provides short provisional or temporary rods used to acquire purchase to the spinal column. The rods are attached to the vertebrae above and below the area of deformity via pedicle screws. To convey three dimensional corrective forces to the spine, the links must attach securely and rigidly to the provisional rods. Freedom of motion in any plane cannot be tolerated. Therefore, a simple slot or hole in the links that captures the provisional rod is not sufficient.

Figure 38B:
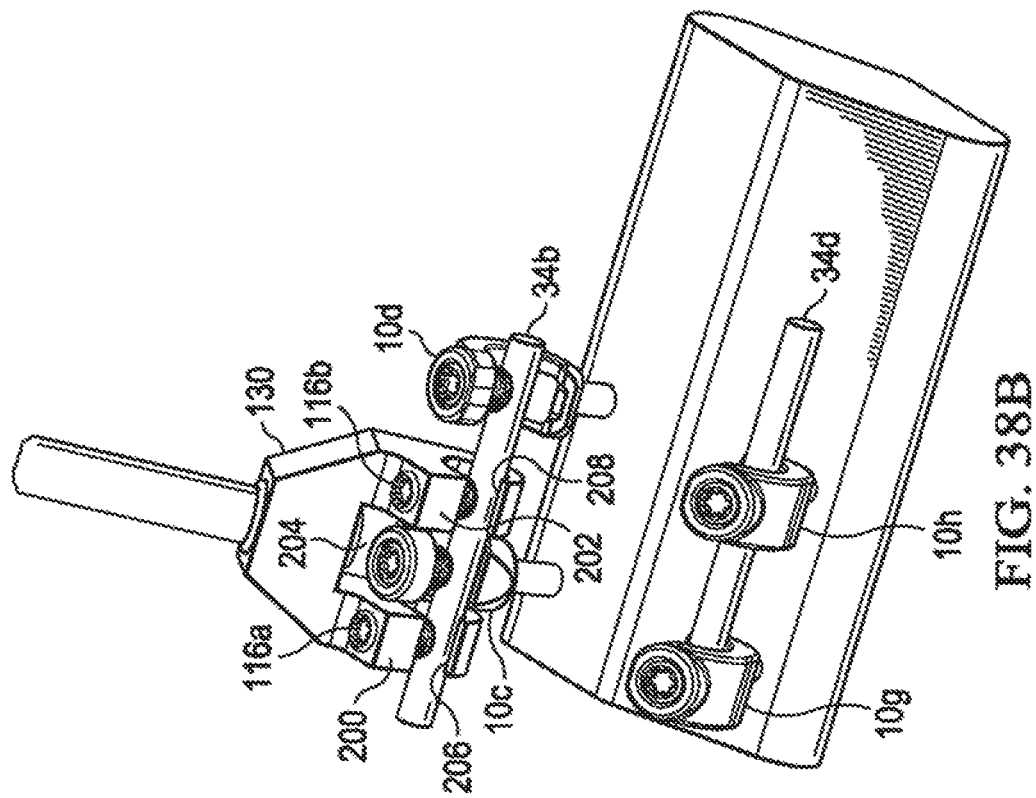
FIGS. 38A and 38B are images of different embodiments of the present invention that show the rigid mechanical connection between the provisional rods and the links.
Figure 38A:
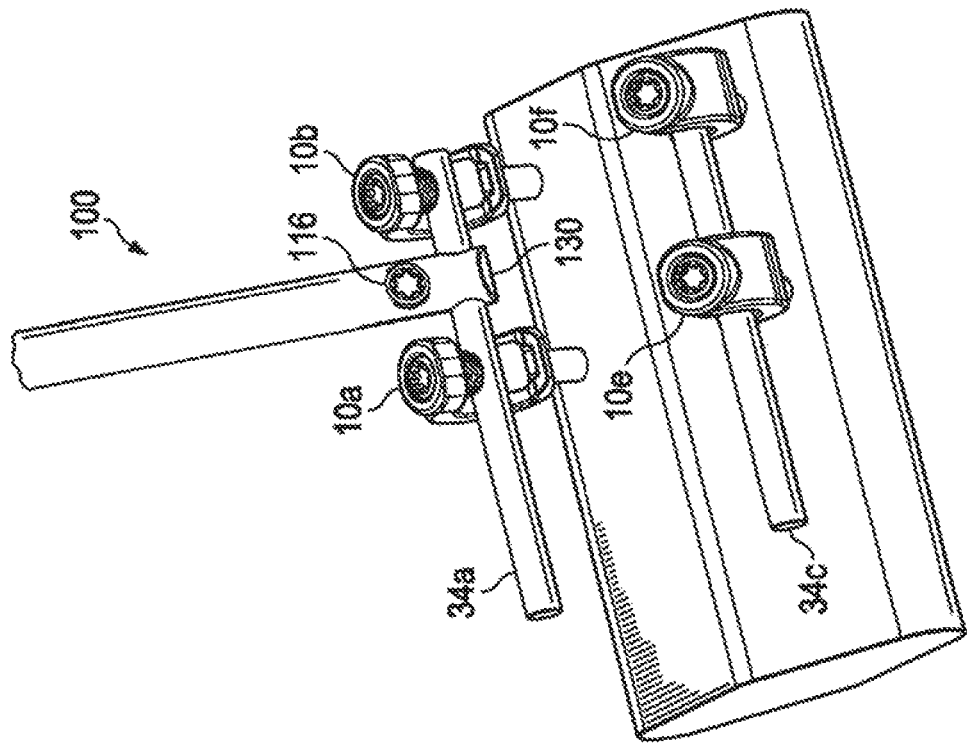

FIGS. 38A and 38B are images of different embodiments of the present invention that show the rigid mechanical connection between the provisional rods and the links. FIGS. 38A and 38B illustrate the temporary rods 34*a*-34*d* attached to pedicle screws 10*a*-10*h*. FIG. 38A is an image of a rod manipulator 102 positioned between pedicle screws 10*a* and 10*b*. The rod manipulator 102 includes a head 130 that has an opening not shown to connect to the temporary rod 34*a*, and screw 116 is used to engage and retain the temporary rod 34*a*. FIG. 38B is an image of a rod manipulator 104 surrounding pedicle screw 10*c*. The rod manipulator 102 includes a head 130 having a first jaw 200 and a second jaw 202 separated by jaw aperture 204. The first jaw 200 includes a first rod coupling aperture 206 connected to the temporary rod 34*b* and screw 116*a* is used to engage and retain the temporary rod 34*b*. The second jaw 202 includes a second rod coupling aperture 208 connected to the temporary rod 34*b* and screw 116*b* is used to engage and retain the temporary rod 34*b*.

Figure 39:
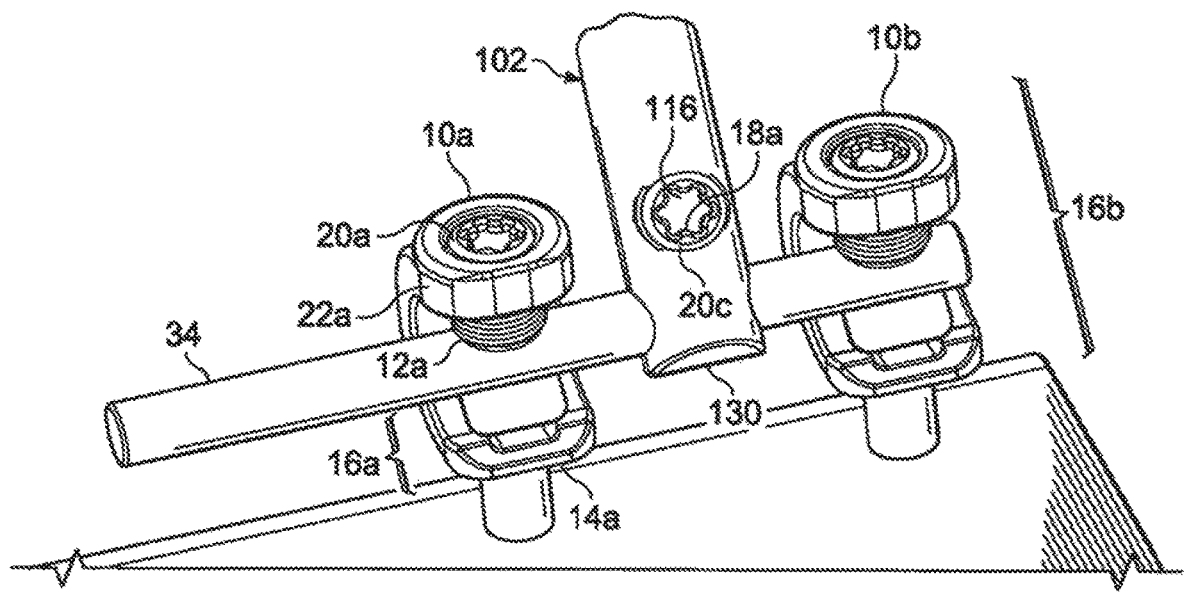
FIG. 39 is a top view of one embodiment of the present invention that shows the rigid mechanical connection between the provisional rods and the links.

FIG. 39 is a top view of one embodiment of the present invention that shows the rigid mechanical connection between the provisional rods and the links. This embodiment of attachment is efficient and compact but does not permit attachment of the link to the provisional rod after the rod has been attached to the pedicle screws. A rod manipulator 102 is shown positioned between pedicle screws 10*a* and 10*b*. Each of the pedicle screws 10*a* and 10*b* includes a bone fastener 12*a*,*b* and a rod coupling head 14*a*,*b*. The rod coupling head 14*a*,*b* includes a lower rod coupling 16*a*,*b* having a lower rod opening 18*a*,*b*, depicted in a lateral configuration. The lower rod opening 18 may have any angle so long as the material of the pedicle screw 10*a*,*b* that surrounds the lower rod opening 18*a*,*b* is sufficiently strong to retain and affix a permanent rod. The lower rod coupling 16*a*,*b* also includes a bore 20*a*,*b*, through which a permanent rod fastener 22*a*,*b* can be inserted to fasten a permanent rod 34. As in the case of the lower rod opening 18*a*,*b*, the material of the pedicle screws 10*a* and 10*b* surrounding the bore 20*a*,*b* will also be sufficiently strong to retain and affix a permanent rod. The rod manipulator 102 includes a head 130 that has an opening (not shown) to connect to the temporary rod 34, and screw 116 is inserted into bore 20*c* to engage and retain the temporary rod 34. The rod manipulator 102 is made from a material with sufficient tensile strength to allow the manipulator to fasten to the rod but also to permit the user to translate movement into the rod in any direction. Again, while this embodiment is shown with screws, any fastening method (pins, set-screws, compression, collets, etc.) may be used to fasten the various components of the rod link reducer of the present invention. In this embodiment, the link cannot be removed from the provisional rod without removing the provisional rod from the screws. This is the most expedient way to remove the link and rod when they are no longer needed, such as in preparation for placement of the final rod.

Figure 40:
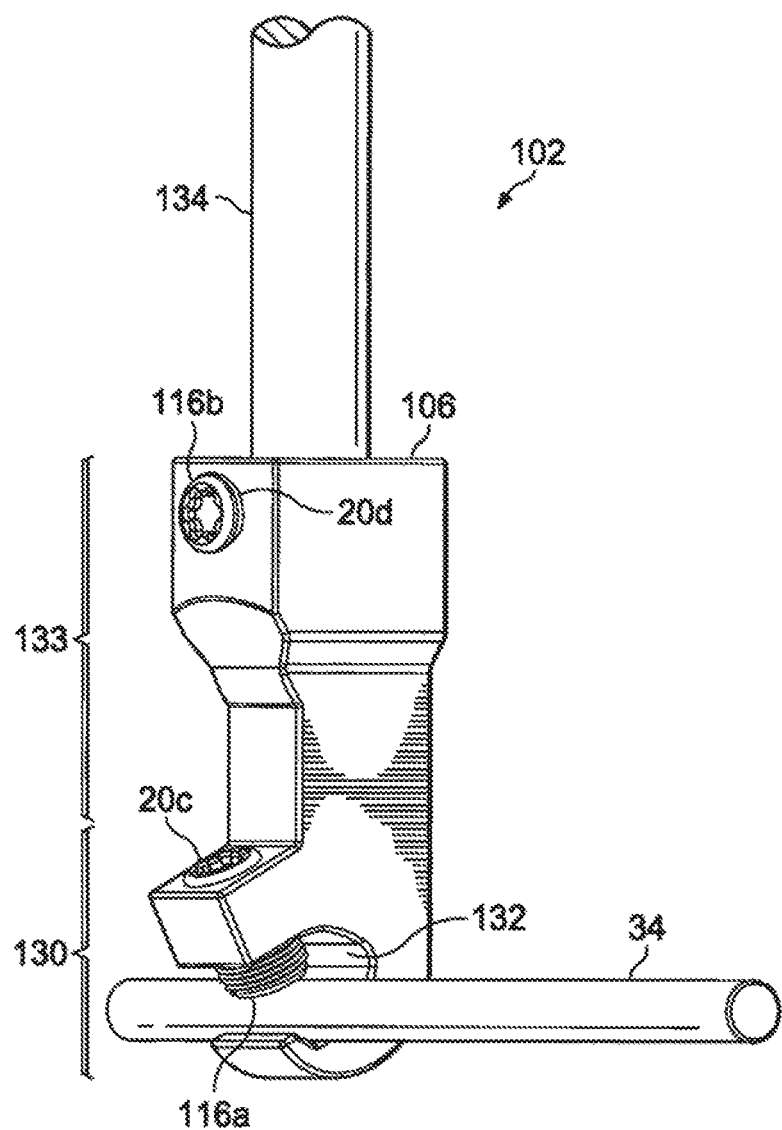
FIG. 40 is a bottom side view of one embodiment of the rod manipulator.

FIG. 40 is a bottom side view of one embodiment of the rod manipulator 102. In this view, screw 116 is shown, as well as first joint 106. This embodiment allows the attachment of a link that has already been secured to the spine. The rod manipulator 102 includes a head 130 that has an opening 132 that first a rod 34 for spinal fixation. The screw 116*a* in aperture 20*c* is used to engage and retain the rod 34. The rod manipulator 102 includes a body portion 133 that includes the first joint 106. The first joint 106 includes an aperture (not shown) to accept a rod or tool. In one embodiment, the handle 134 is inserted into the aperture (not shown) and secured by tightening screw is 116*b* in aperture 20*d*. The rod manipulator 102 may be used in conjunction with existing spinal screw and rod fixation systems. The size and thickness of rods may be varied depending on the type of surgery, tensile strength required and preference of the user.

Figure 41:
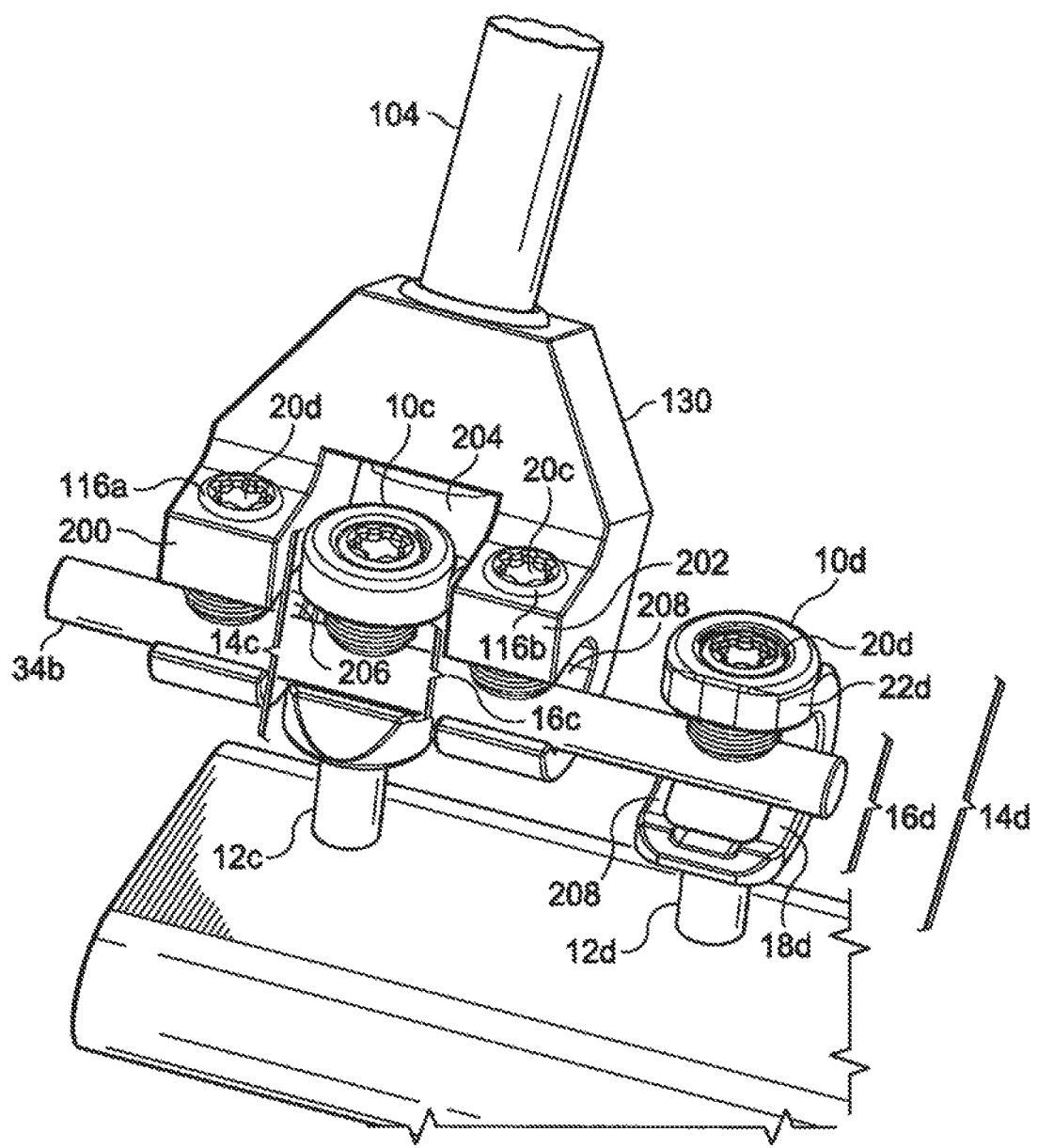
FIG. 41 is a side view of a wide stance embodiment of the present invention that shows the rigid mechanical connection between the provisional rods and the links.

FIG. 41 is a side view of a wide stance embodiment of the present invention that shows the rigid mechanical connection between the provisional rods and the links. The space between malformed vertebrae can be quite narrow at times. A grip narrow enough to fit between them may not be sufficiently stable under bending loads to be effective. The advantage of this double hook/screw grip is that the hooks can be narrow while still enabling a wide stable grip on the rods. In addition, two set screws are better than one to prevent rotation on the small diameter rods. Again, it is possible to use fluted or faceted rods and a corresponding profile on the hooks to enhance rotational stability. FIG. 41 is an image of a rod manipulator 104 positioned between pedicle screws 10*c* and 10*d*. Each of the pedicle screws 10*c* and 10*d* includes a bone fastener 12*c*,*d* and a rod coupling head 14*c*,*d*. The rod coupling head 14*c*,*d* includes a lower rod coupling 16*c*,*d* having a lower rod opening 18*c*,*d*, depicted in a lateral configuration. The lower rod opening 18 may have any angle so long as the material of the pedicle screw 10*c*,*d* that surrounds the lower rod opening 18*c*,*d* is sufficiently strong to retain and affix a permanent rod. The lower rod coupling 16*c*,*d* also includes a bore 20*c*,*d*, through which a permanent rod fastener 22*c*,*d* can be inserted to fasten a permanent rod 34*b*. As in the case of the lower rod opening 18*c*,*d*, the material of the pedicle screws 10*c* and 10*d* surrounding the bore 20*c*,*d* will also be sufficiently strong to retain and affix a permanent rod 34*b*. The rod manipulator 104 surrounds pedicle screw 10*c*. The rod manipulator 104 includes a head 130 having a first jaw 200 and a second jaw 202 separated by jaw aperture 204. The first jaw 200 includes a first rod coupling aperture 206 connected to the temporary rod 34*b* and screw 116*a* inserted into the bore 20*d* is used to engage and retain the temporary rod 34*b*. The second jaw 202 includes a second rod coupling aperture 208 connected to the temporary rod 34*b* and screw 116*b* inserted into the bore 20*c* is used to engage and retain the temporary rod 34*b*.

Figure 42:
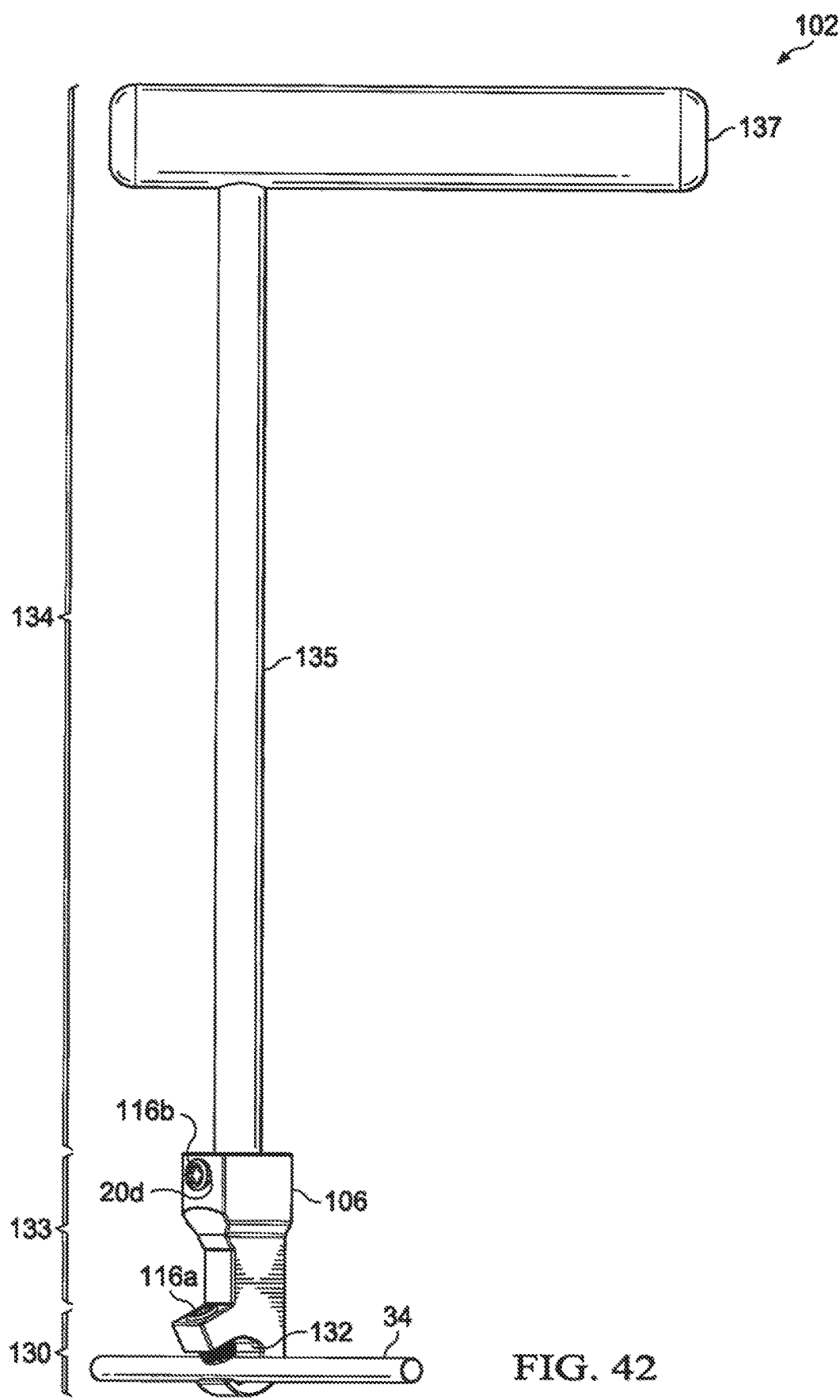
FIG. 42 is a bottom side view of one embodiment of the rod manipulator.

FIG. 42 is a bottom side view of one embodiment of the rod manipulator 102. The rod manipulator 102 provides a means to torque the links about their axes, in addition to bending forces and axial pushing or pulling forces. In situations where the anatomy precludes placing the links at the appropriate angle to correct the deformity, the prior art device cannot be used to good advantage. By providing the links with a T-handle which enables twisting, the planar restriction of the device is eliminated. An intuitive combination of bending, twisting and displacement now enable true three dimensional spinal deformity correction. In this view screw is 116 are shown as well as first joint 106. The rod manipulator 102 includes a head 130 that has an opening 132 that first a rod 34 for spinal fixation. The screw 116*a* is used to engage and retain the rod 34. The rod manipulator 102 includes a body portion 133 that includes the first joint 106. The first joint 106 includes an aperture (not shown) to accept a rod or tool. In one embodiment, the handle 134 is inserted into the aperture (not shown) and secured by tightening screw is 116*b* in aperture 20*d*. The handle includes a shaft 135 attached at one end to the first joint 106 and a second bar or "T" bar 137. Although other shapes and configurations may be used. The rod manipulator 102 may be used in conjunction with existing spinal screw and rod fixation systems. The size and thickness of rods may be varied depending on the type of surgery, tensile strength required and preference of the user.

Figure 43:
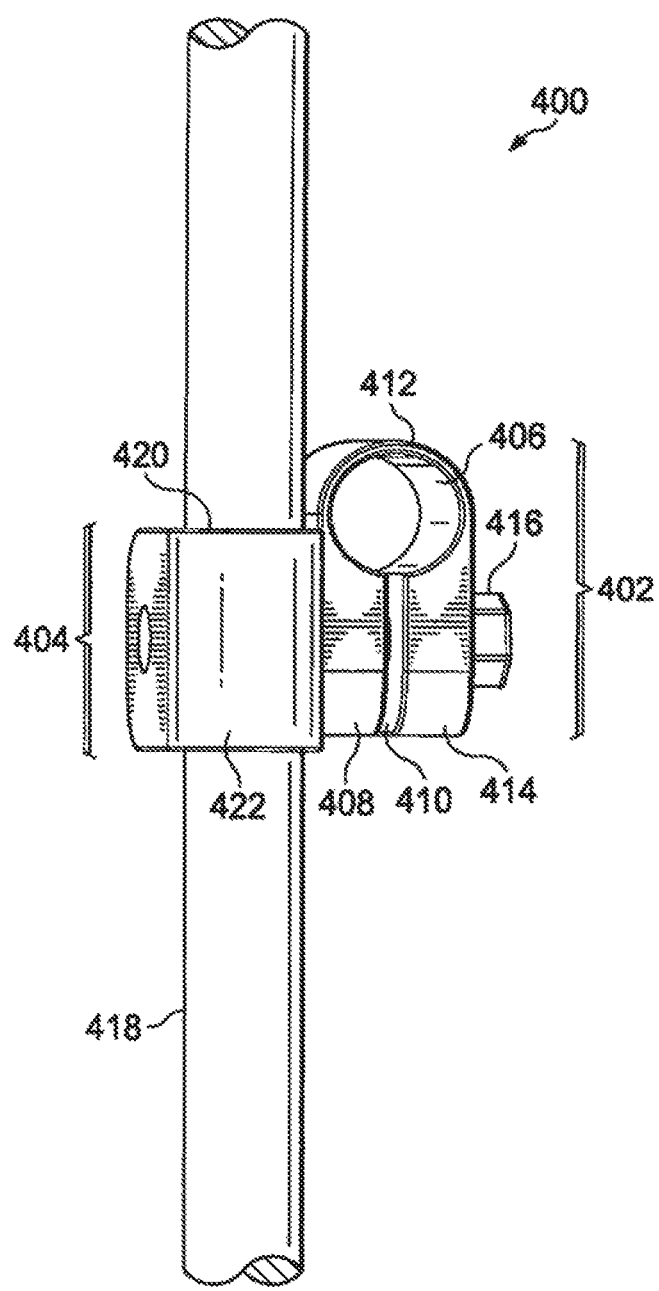
FIG. 43 is a side view of one embodiment of a rod clamp of the present invention.

FIG. 43 is a side view of one embodiment of a rod clamp 400 of the present invention. The purpose of the connecting bar is to lock and hold the links in a particular orientation once the correction has been achieved but still permit free movement of the links during the correction procedure. The links are given round shafts so that the clamps can rotate on them. Existing rod to rod external fixation clamps are used to connect a rigid bar between the links. The result is a connection which provides universal motion but can be securely locked when the two rod-to-rod clamps are tightened. The rod clamp 400 has a first side 402 and a second side 404 connected through a central point (not shown). The first side 402 has a first rod aperture 406 sized to fit a rod (not shown). The first side 402 has a first end 408 that extends to a slot 410 and extends in a curve 412 to form first rod aperture 406 extending to second end 414 adjacent to first side 402 separated by slot 410. The rod clamp 400 includes bolt (not shown) that extends through the second end 414, the slot 410 and first end 408 being capped by nut 416. In operation, a rod (not shown) may be placed in the first rod aperture 406. The nut 416 is tightened, compressing the slot 410 bringing second end 414 and the first end 408 closer together, and in turn reducing the size of the first rod aperture 406 to frictionally fit the rod (not shown) in position. The second side 404 displays the rod 418 inserted into second rod aperture 420 made from the curve 422.

Figure 44:
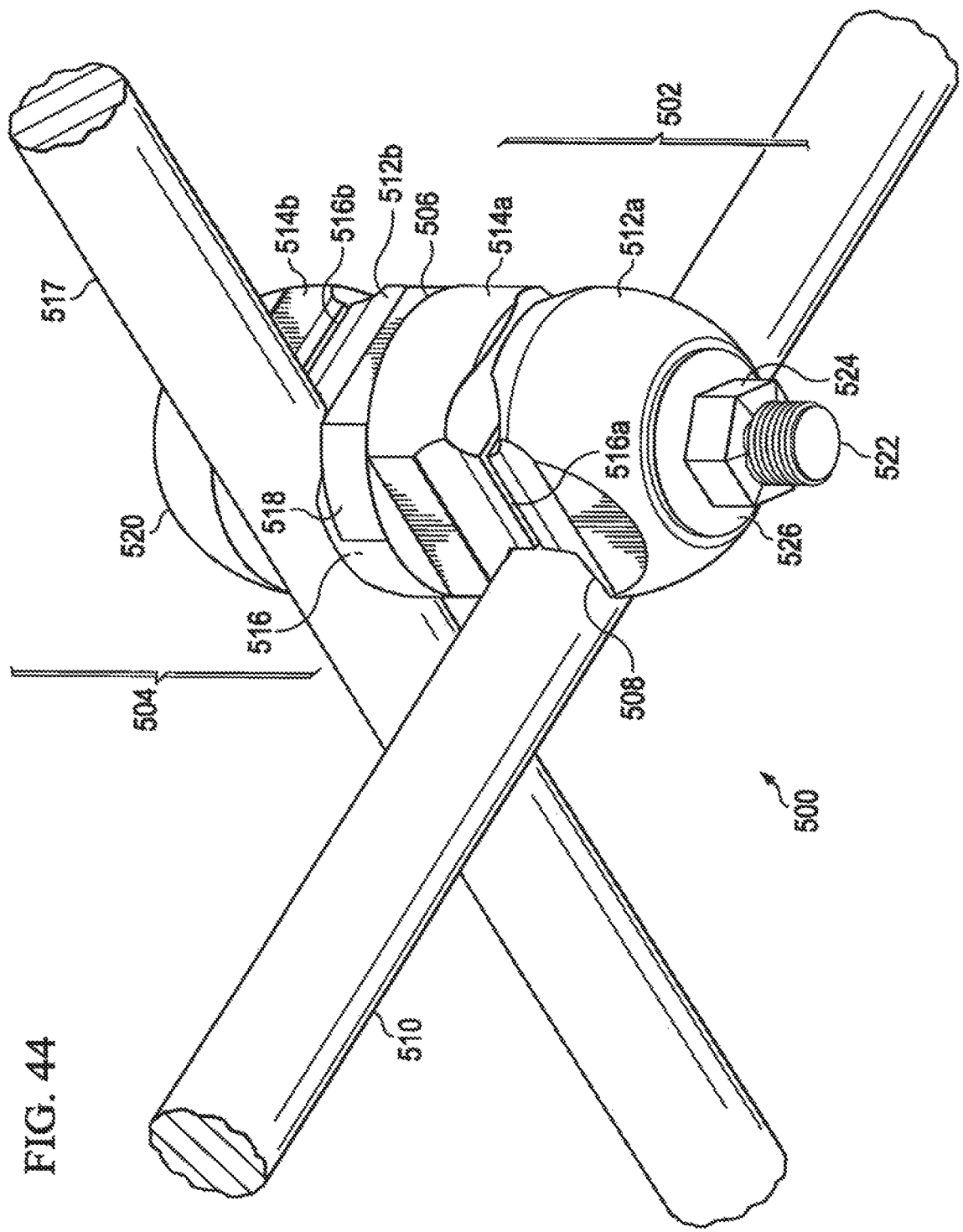
FIG. 44 is a side view of one embodiment of a rod clamp 500 of the present invention.

FIG. 44 is a view of one embodiment of a rod clamp 500 of the present invention. The rod clamp 500 has a first side 502 and a second side 504 connected through a connection junction 506. The first side 502 has a first rod aperture 508 sized to fit a first rod 510. The first side 502 has a first end 512a that mates to second end 514a separated by the slot junction 516a. The first end 512a has a first tab (not shown) and the second end 514a has a second tab (not shown) that form a first rod aperture 508 when the first end 512a and the second end 514a are mated. The second side 504 has a second rod aperture 516 sized to fit a second rod 517. The first side 502 has a first end 512b that mates to second end 514b by slot junction 516b. The first end 512 has a first tab 518 and the second end 514 has a second tab 520 that form a second rod aperture 516 when the first end 512b and the second end 514b are mated. The rod clamp 500 is secured by extending the bolt 522 through the first side 502, the connection junction 506 and the second side 504 and securing with nut 524 and washer 526. The bolt 522 extends through the first end 512a into the slot junction 516a to mate to the second end 514a. The bolt 522 extends through the connection junction 506 into the first end 512b that mates to second end 514b through slot junction 516b to secure the first side 502 relative to the second side 504. In operation, a first rod 510 is inserted into the first rod aperture 508 of the first side 502 and a second rod 517 is inserted into the second rod aperture 516b of the second side 504. The nut 524 is tightened compressing the first side 502 to compress the first rod aperture 508 and also compress the second side 504 and in turn the second rod aperture 516 and the connection junction 506. These clamps can be fully encircling or partially encircling or a combination thereof. Partial or clamshell construction enables snapping the clamp onto a link at any point along the shaft. Full encirclement insures that the clamp will not accidentally disengage from the link when in the loosened state. A hybrid clamp composed of a partial half on one side and a fully encircling one on the other would insure that the clamps stay retained on one part while allowing that part to be easily attached to other components. In addition, the connections between any of the first and second portions or the faces of mating of surfaces may be textured, faceted or splinned to enhance rotational stability.

Figure 45:
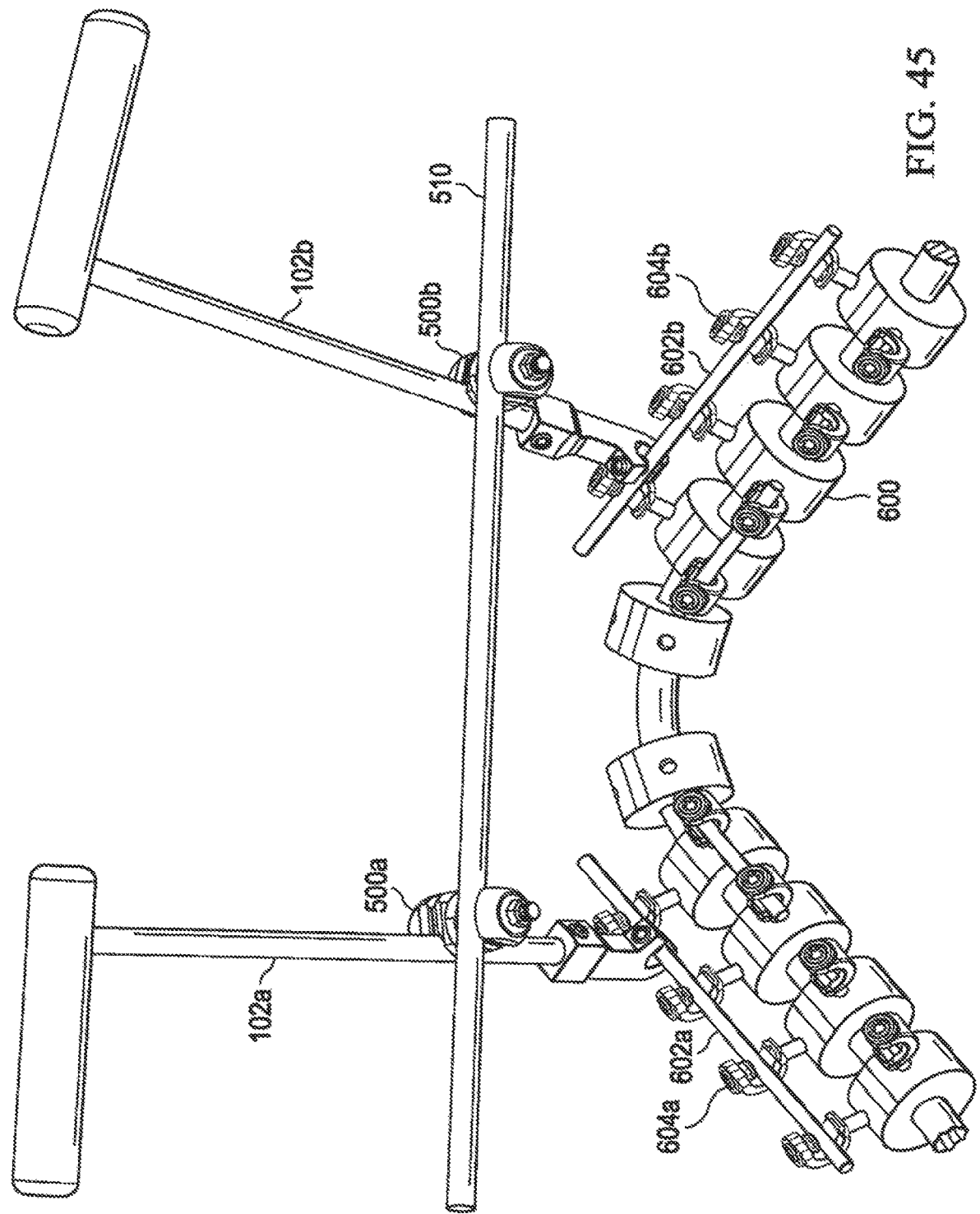
FIG. 45 is a side view of one embodiment of a rod clamp of the present invention in operation.

FIG. 45 is a view of one embodiment of a rod clamp of the present invention in operation. The image illustrates the first rod manipulator 102a connected to the first rod clamp 500a. The rod 510 extends from the first rod clamp 500a to second rod clamp 500b that is attached to a second rod manipulator 102b. The first rod manipulator 102a is secured to the artificial spine 600 through attachment to the temporary rods 602a and pedicle screws 604a inserted into the artificial spine 600. Similarly, the second rod manipulator 102b is secured to the artificial spine 600 through attachment to the temporary rods 602b and pedicle screws 604b inserted into the artificial spine 600.

Figure 46:
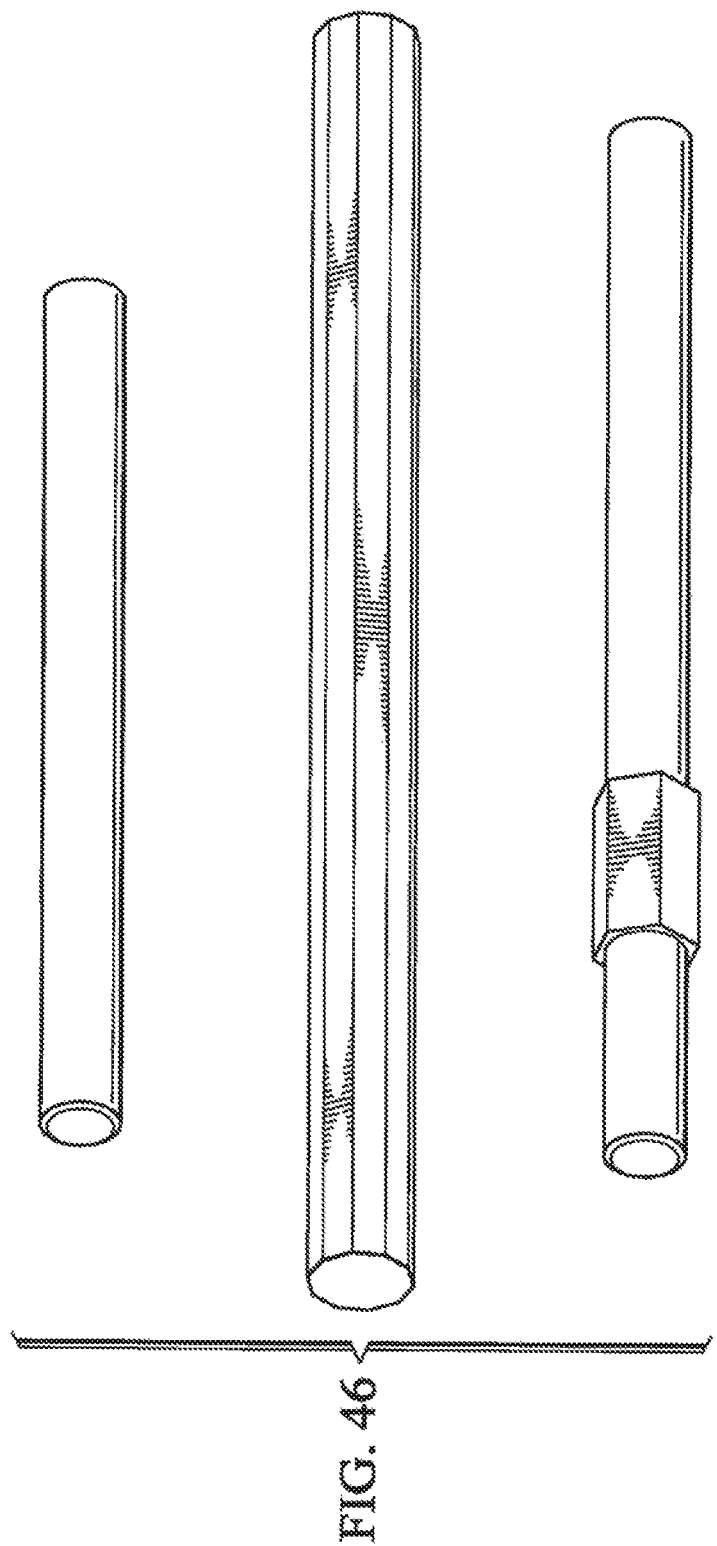
FIG. 46 is a side view of some of the rods used with the present invention.

FIG. 46 is a view of some of the rods used with the present invention. The link contains a cross hole into which the provisional rod is inserted and then locked into place with a setscrew. The cross hole can be configured to capture provisional rods of several different diameters. In addition, it can be configured to capture provisional rods that are faceted or splinned to enhance rotational stability.

Figure 47:
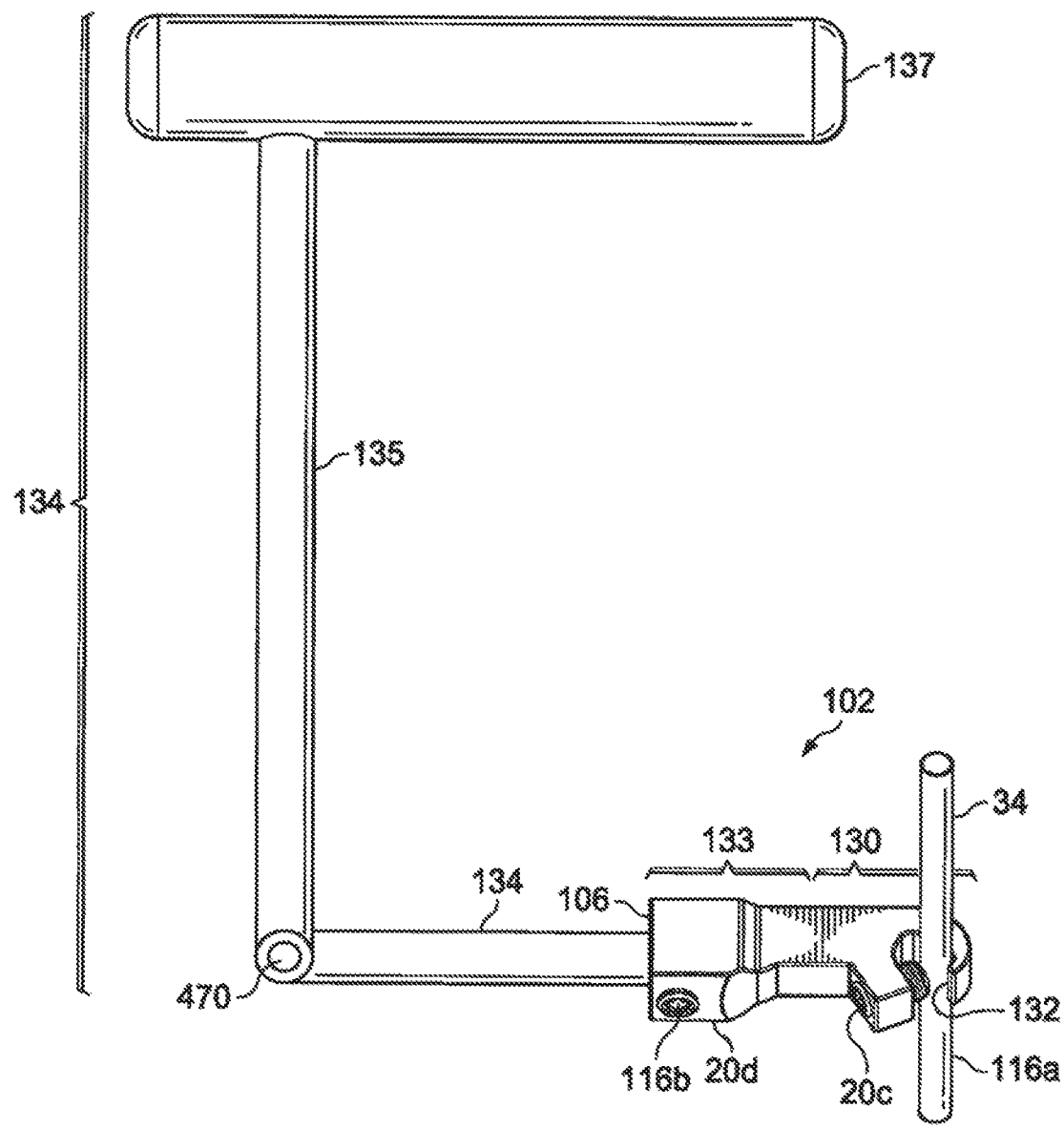
FIG. 47 is a side view of one embodiment of the rod manipulator having an adjustable joint in the handle ending in a "T" handle.

FIG. 47 is a side view of one embodiment of the rod manipulator 102 having an adjustable joint 470 in the handle 134 ending in a "T" handle 137. The rod manipulator 102 provides a means to torque the links about their axes, in addition to bending forces and axial pushing or pulling forces. In situations where the anatomy precludes placing the links at the appropriate angle to correct the deformity, the prior art device cannot be used to good advantage. By providing the links with a T-handle which enables twisting, the planar restriction of the device is eliminated. An intuitive combination of bending, twisting and displacement now enable true three dimensional spinal deformity correction. In this view screw is 116 are shown as well as first joint 106. The rod manipulator 102 includes a head 130 that has an opening 132 that first a rod 34 for spinal fixation. The screw 116a is used to engage and retain the rod 34. The rod manipulator 102 includes a body portion 133 that includes the first joint 106. The first joint 106 includes an aperture (not shown) to accept a rod or tool. In one embodiment, the handle 134 is inserted into the aperture (not shown) and secured by tightening screw is 116b in aperture 20d. The handle includes a shaft 135 attached at one end to the first joint 106 and a second bar or "T" bar 137. Furthermore, other shapes and configurations may be used. The rod manipulator 102 may be used in conjunction with existing spinal screw and rod fixation systems. In this view, screw 116 is shown, as well as first joint 106. This embodiment allows the attachment of a link that has already been secured to the spine. The rod manipulator 102 includes a head 130 that has an opening 132 that first a rod 34 for spinal fixation. The screw 116a in aperture 20c is used to engage and retain the rod 34. The rod manipulator 102 includes a body portion 133 that includes the first joint 106. The first joint 106 includes an aperture (not shown) to accept a rod or tool. In one embodiment, the handle 134 is inserted into the aperture (not shown) and secured by tightening screw is 116b in aperture 20d. The rod manipulator 102 may be used in conjunction with existing spinal screw and rod fixation systems. The adjustable joint 470 allows the relative angle between the head 130 and the handle 134 ending in a "T" handle 137 be adjusted as needed by rotating the adjustable joint 470 to the desired position. The adjustable joint 470 may have a locking mechanism that is depressed to allow adjustment and unlocking and released to lock in place. The size and thickness of rods may be varied depending on the type of surgery, tensile strength required and preference of the user.

FIGS. 48A and 48B are images of the joint adapted into a joint of a larger device. FIG. 48A is an image of the first gear 200 positioned in the head 264 of the first side 266 of the device aligned with the second gear 226 positioned in the head 268 of the second half of the device 270. The first gear 200 includes two or more teeth 204 and a central aperture 258 that is aligned with the positioning cylinder 228 that serves to align the two or more teeth 204 with the two or more second teeth 248. FIG. 48B is an image of the first gear 200 positioned in the head 264 of the first side 266 of the device mated to the second gear 226 positioned in the head 268 of the second half of the device 270. The first gear 200 includes two or more teeth 204 and a central aperture (not shown) that receives the positioning cylinder (not shown) that serves to align the two or more teeth 204 with the two or more second teeth 248.

FIG. 49 is an exploded isometric image of the joint adapted into a larger device. FIG. 49 is an exploded isometric left image that includes a joint 470 having a first body 472 that mates to a second body 474. The first body 472 includes a first connection end 476 adjacent a first head 278. The first head 478 includes a gear cavity 480 positioned within the first head 478 to receive a spring, spacer or washer 482 (optional) and a first gear 484 that is positioned between the body back portion 486 and the front face 488. The first gear 484 includes a first gear back 490 opposite a first gear face 492 that includes two or more first gear teeth 494 extending from the periphery of the first gear face 492 across the face toward the center that are suitable to allow friction between surfaces. In the center of the first gear 484 is a first alignment aperture 496 to aid in the alignment of the first gear 484. The second body 474 includes a second connection end 498 adjacent a second head 501. The second head 500 includes a release recess 502 that extends from the outside inwardly into at least a portion of the second head 500. Within the release recess 502 there are numerous release apertures 504 that extend from the release recess 502 through the second head 501. A release spring/washer 506 is positioned within the release recess 502. A release mechanism 508 is placed in contact with the spring/washer 506 and the release pins 511 are passed through the numerous release apertures 504 and is secured by the retaining clip 512.

Figure 50:
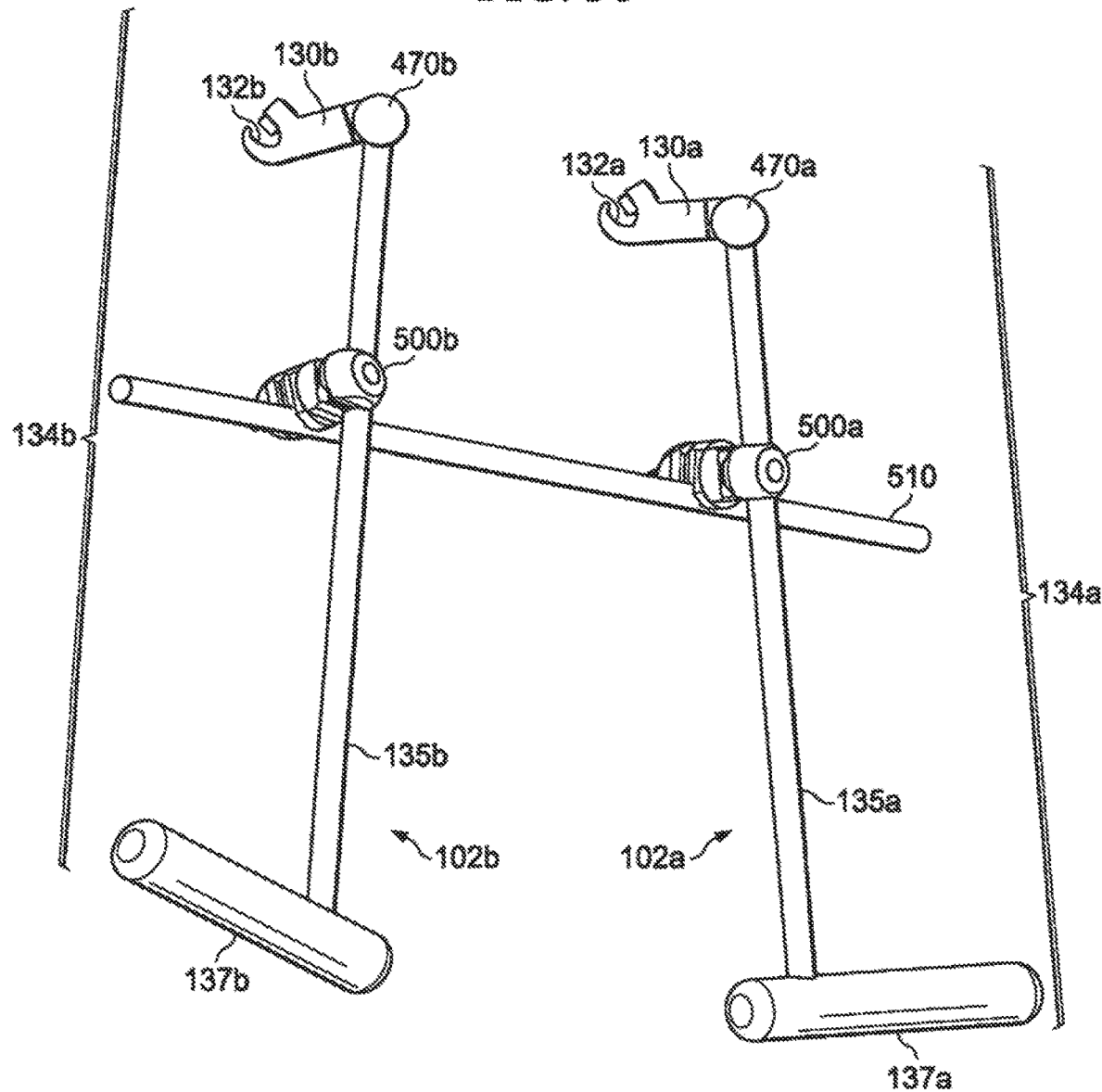
FIG. 50 is a view of one embodiment of a rod clamp of the present invention in operation.

FIG. 50 is a view of one embodiment of a rod clamp of the present invention in operation. The image illustrates the first rod manipulator 102a connected to the first rod clamp 500a. The rod 510 extends from the first rod clamp 500a to second rod clamp 500b that is attached to a second rod manipulator 102b. The rod manipulator 102a and 102b have an adjustable joint 470a and 470b in shaft 135a and 135b attached at one end to a head 130a and 130b that has an opening 132a and 132b for spinal fixation and a bar or "T" bar 137a and 137b at a second end. The rod manipulators 102a and 102b provides a means to torque the links about their axes, in addition to bending forces and axial pushing or pulling forces. In situations where the anatomy precludes placing the links at the appropriate angle to correct the deformity, the prior art device cannot be used to good advantage. By providing the links with a T-handle which enables twisting, the planar restriction of the device is eliminated. An intuitive combination of bending, twisting and displacement now enable true three dimensional spinal deformity correction.

Figure 51:
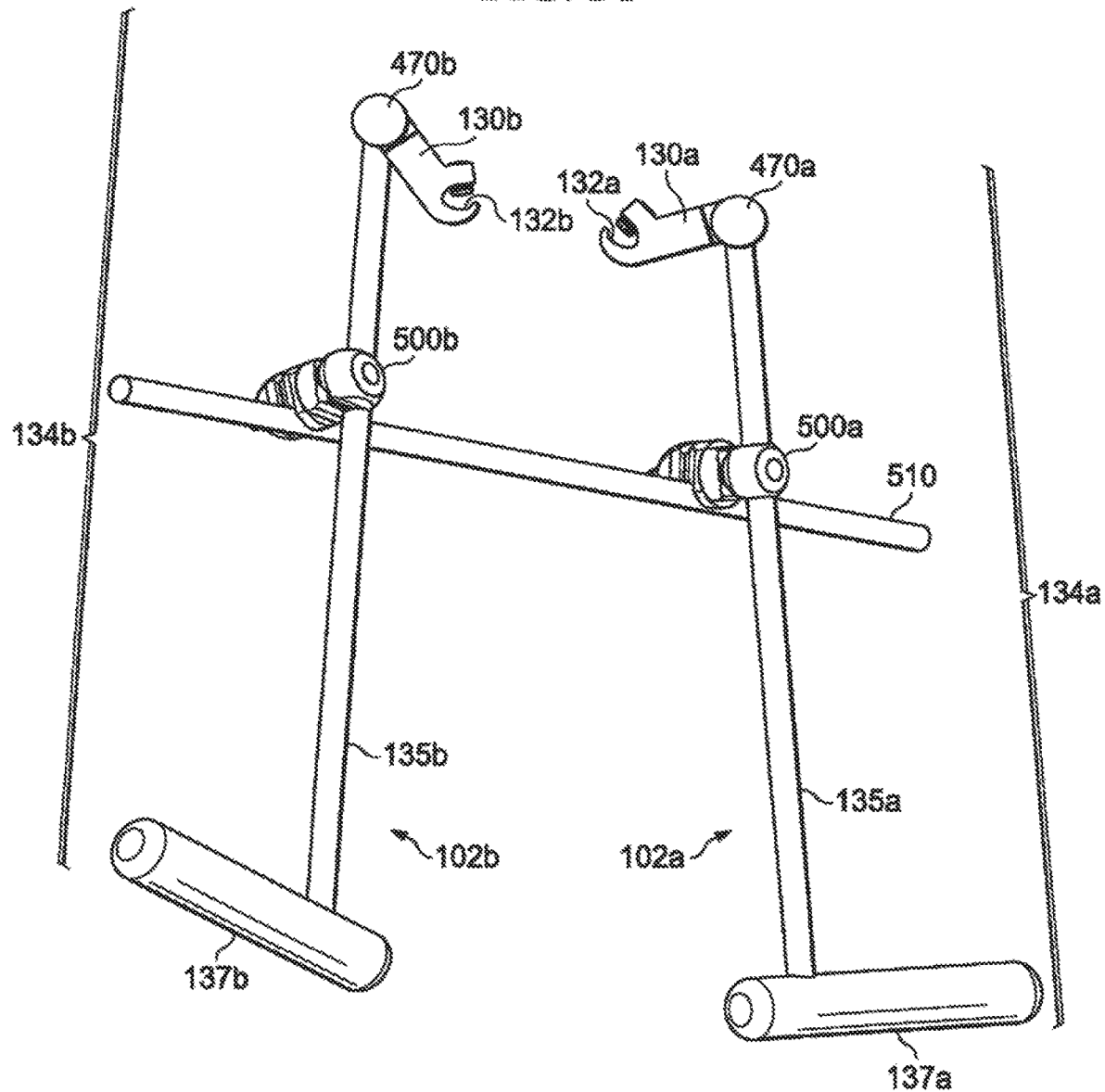
FIG. 51 is a view of another embodiment of a rod clamp of the present invention in operation.

FIG. 51 is a view of another embodiment of a rod clamp of the present invention in operation. The image illustrates the first rod manipulator 102a connected to the first rod clamp 500a. The rod 510 extends from the first rod clamp 500a to second rod clamp 500b that is attached to a second rod manipulator 102b. The rod manipulator 102a and 102b have an adjustable joint 470a and 470b in shaft 135a and 135b attached at one end to a head 130a and 130b that has an opening 132a and 132b for spinal fixation and a bar or "T" bar 137a and 137b at a second end. The rod manipulators 102a and 102b provides a means to torque the links about their axes, in addition to bending forces and axial pushing or pulling forces. In situations where the anatomy precludes placing the links at the appropriate angle to correct the deformity, the prior art device cannot be used to good advantage. By providing the links with a T-handle which enables twisting, the planar restriction of the device is eliminated. An intuitive combination of bending, twisting and displacement now enable true three dimensional spinal deformity correction.

Figure 52:
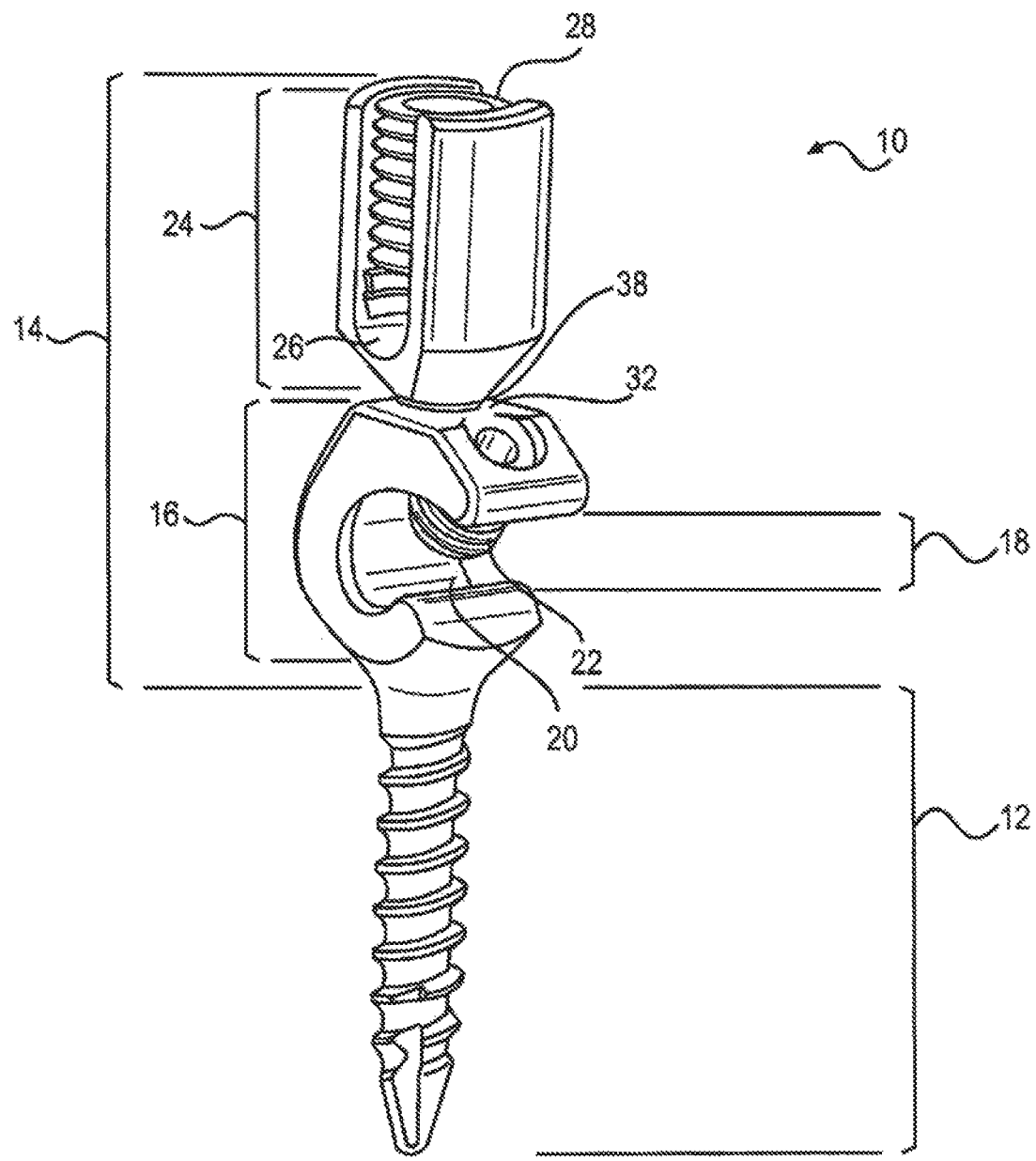
FIG. 52 shows an isometric view of one embodiment of the pedicle screw having a removable upper rod coupling.

FIG. 52 shows an isometric view of one embodiment of the pedicle screw having a removable upper rod coupling. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod (not shown). The lower rod coupling 16 also includes a bore 20, through which a permanent rod fastener 22 can be inserted to fasten a permanent rod (not shown). As in the case of the lower rod opening 18, the material of the pedicle screw 10 surrounding the bore 20 will also be sufficiently strong to retain and affix a permanent rod (not shown). The upper rod coupling 24 has an upper rod opening 26. The upper rod coupling 24 is formed to permit the user to insert a temporary rod (not shown) using a temporary rod fastener 28. The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 53:
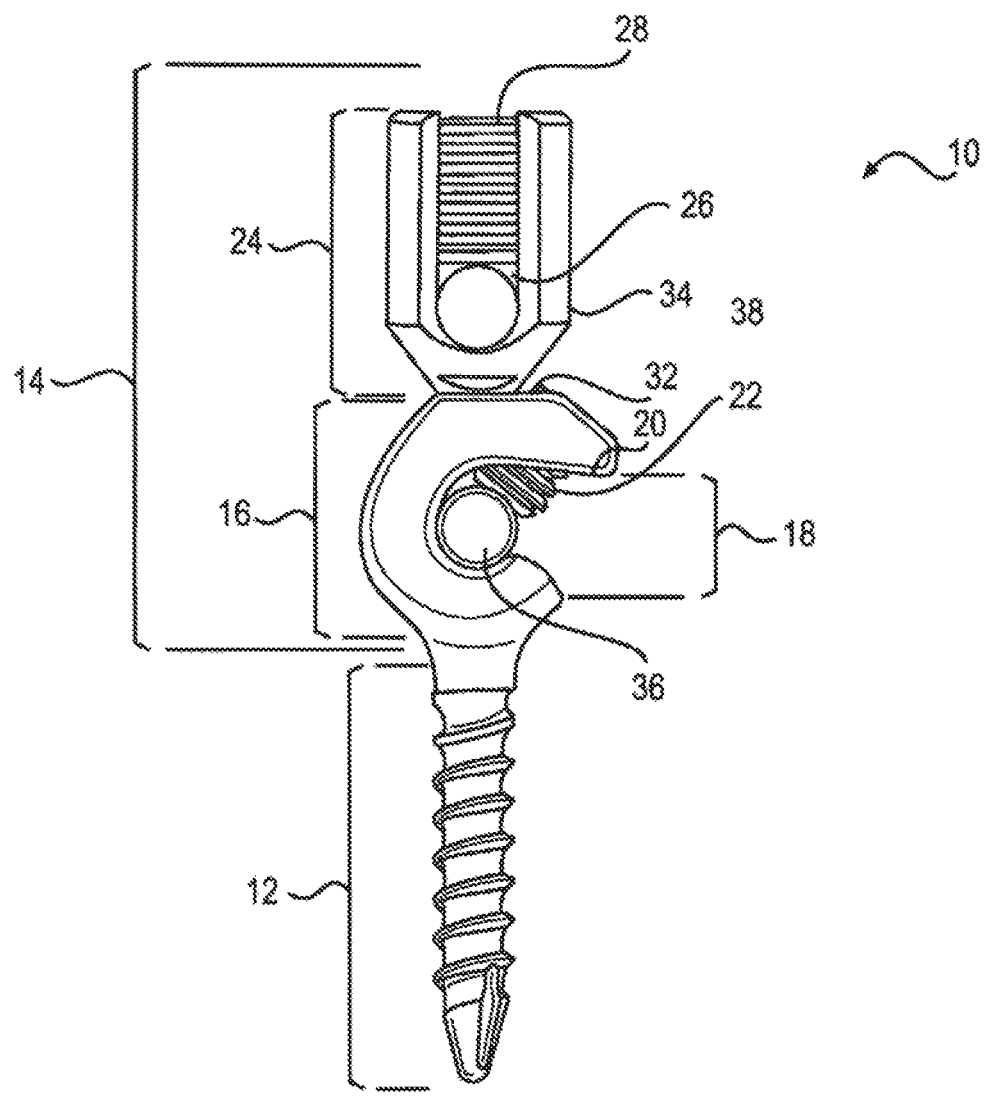
FIG. 53 shows a side view of one embodiment of the pedicle screw having a removable upper rod coupling.

FIG. 53 shows a side view of one embodiment of the pedicle screw having a removable upper rod coupling. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36. The lower rod coupling 16 also includes a bore 20, through which a permanent rod fastener 22 can be inserted to fasten a permanent rod 36. As in the case of the lower rod opening 18, the material of the pedicle screw 10 surrounding the bore 20 will also be sufficiently strong to retain and affix a permanent rod 36. The upper rod coupling 24 has an upper rod opening 26. The upper rod coupling 24 is formed to permit the user to insert a temporary rod 34 using a temporary rod fastener 28. The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 54:
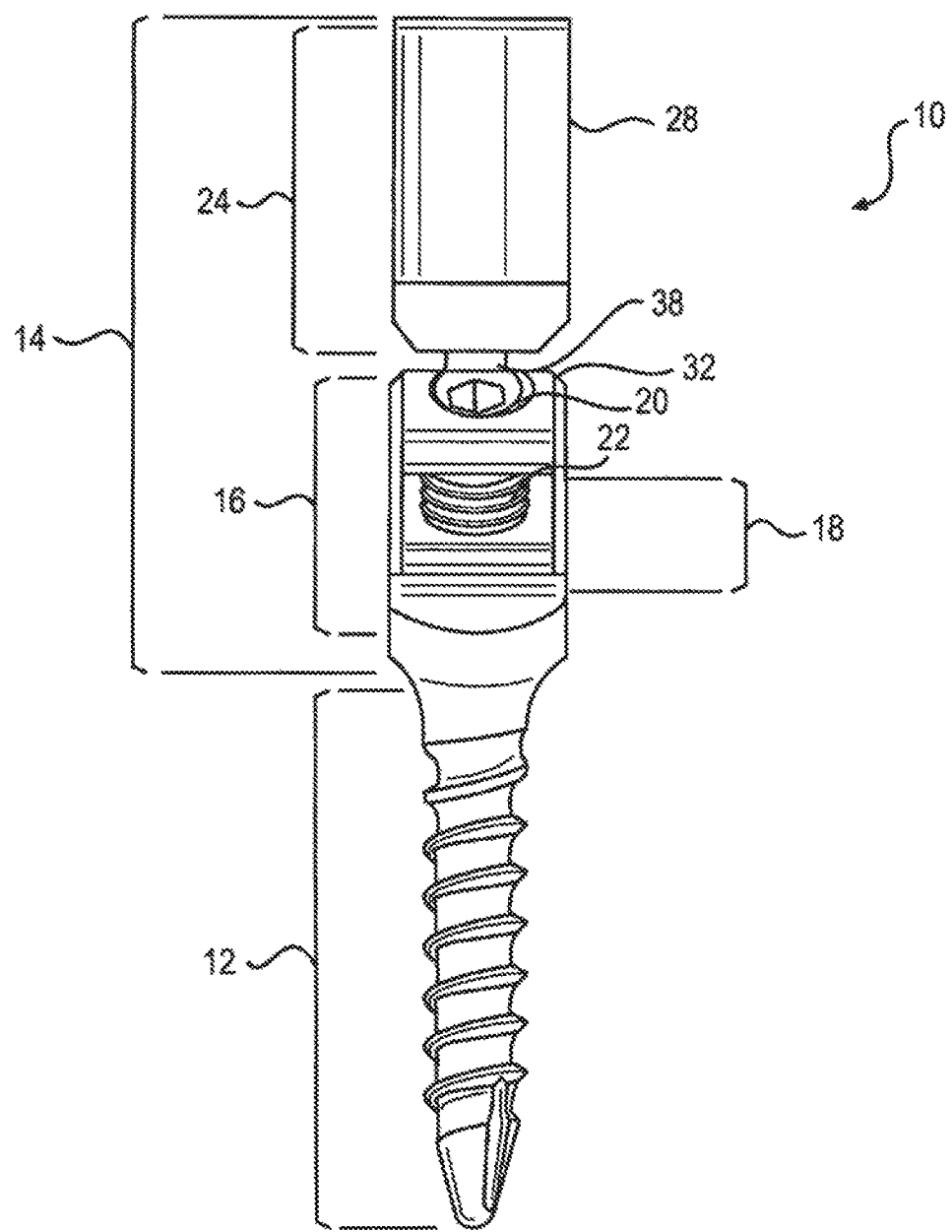
FIG. 54 shows a front view of one embodiment of the pedicle screw having a removable upper rod coupling.

FIG. 54 shows a front view of one embodiment of the pedicle screw having a removable upper rod coupling. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod (not shown). The lower rod coupling 16 also includes a bore 20, through which a permanent rod fastener 22 can be inserted to fasten a permanent rod (not shown). As in the case of the lower rod opening 18, the material of the pedicle screw 10 surrounding the bore 20 will also be sufficiently strong to retain and affix a permanent rod (not shown). The upper rod coupling 24 has an upper rod opening (not shown). The upper rod coupling 24 is formed to permit the user to insert a temporary rod (not shown) using a temporary rod fastener 28. The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 55:
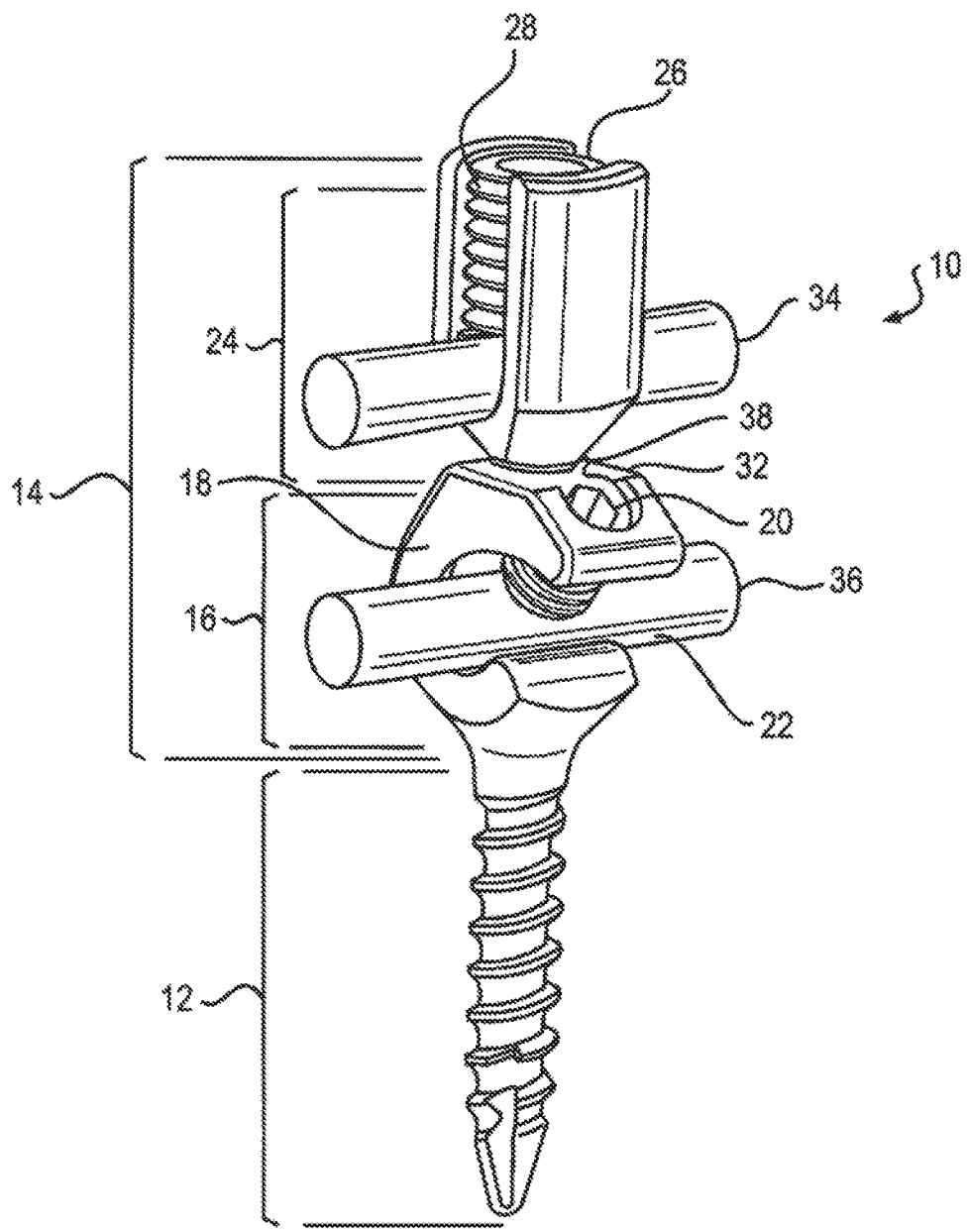
FIG. 55 shows an isometric view of one embodiment of the pedicle screw having a removable upper rod coupling showing the permanent rod and temporary rod.

FIG. 55 shows an isometric view of one embodiment of the pedicle screw having a removable upper rod coupling showing the permanent rod and temporary rod. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36. The lower rod coupling 16 also includes a bore 20, through which a permanent rod fastener 22 can be inserted to fasten a permanent rod 36. As in the case of the lower rod opening 18, the material of the pedicle screw 10 surrounding the bore 20 will also be sufficiently strong to retain and affix a permanent rod 36. The upper rod coupling 24 has an upper rod opening 26. The upper rod coupling 24 is formed to permit the user to insert a temporary rod 34 using a temporary rod fastener 28. The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 56:
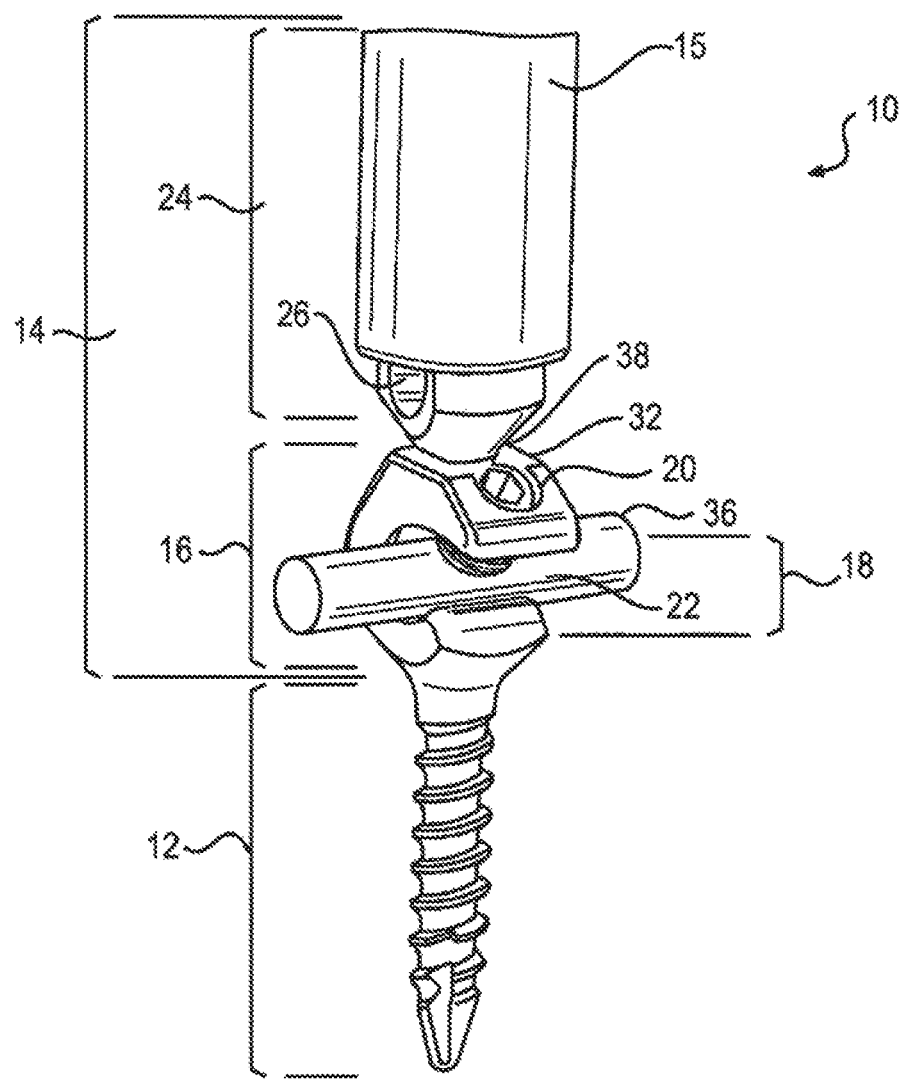
FIG. 56 shows an isometric view of one embodiment of the pedicle screw having a removable upper rod coupling showing temporary rod with the upper rod coupling removal tool.

FIG. 56 shows an isometric view of one embodiment of the pedicle screw having a removable upper rod coupling showing temporary rod with the upper rod coupling removal tool. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36. The lower rod coupling 16 also includes a bore 20, through which a permanent rod fastener 22 can be inserted to fasten a permanent rod 36. As in the case of the lower rod opening 18, the material of the pedicle screw 10 surrounding the bore 20 will also be sufficiently strong to retain and affix a permanent rod 36. The upper rod coupling 24 has an upper rod opening 26. The upper rod coupling 24 is formed to permit the user to insert a temporary rod (not shown) using a temporary rod fastener (not shown). The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. The upper rod coupling removal tool 15 is used by positioning it about the upper rod coupling 24 to break at the transition 32 and at breakpoint 38 between the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 57:
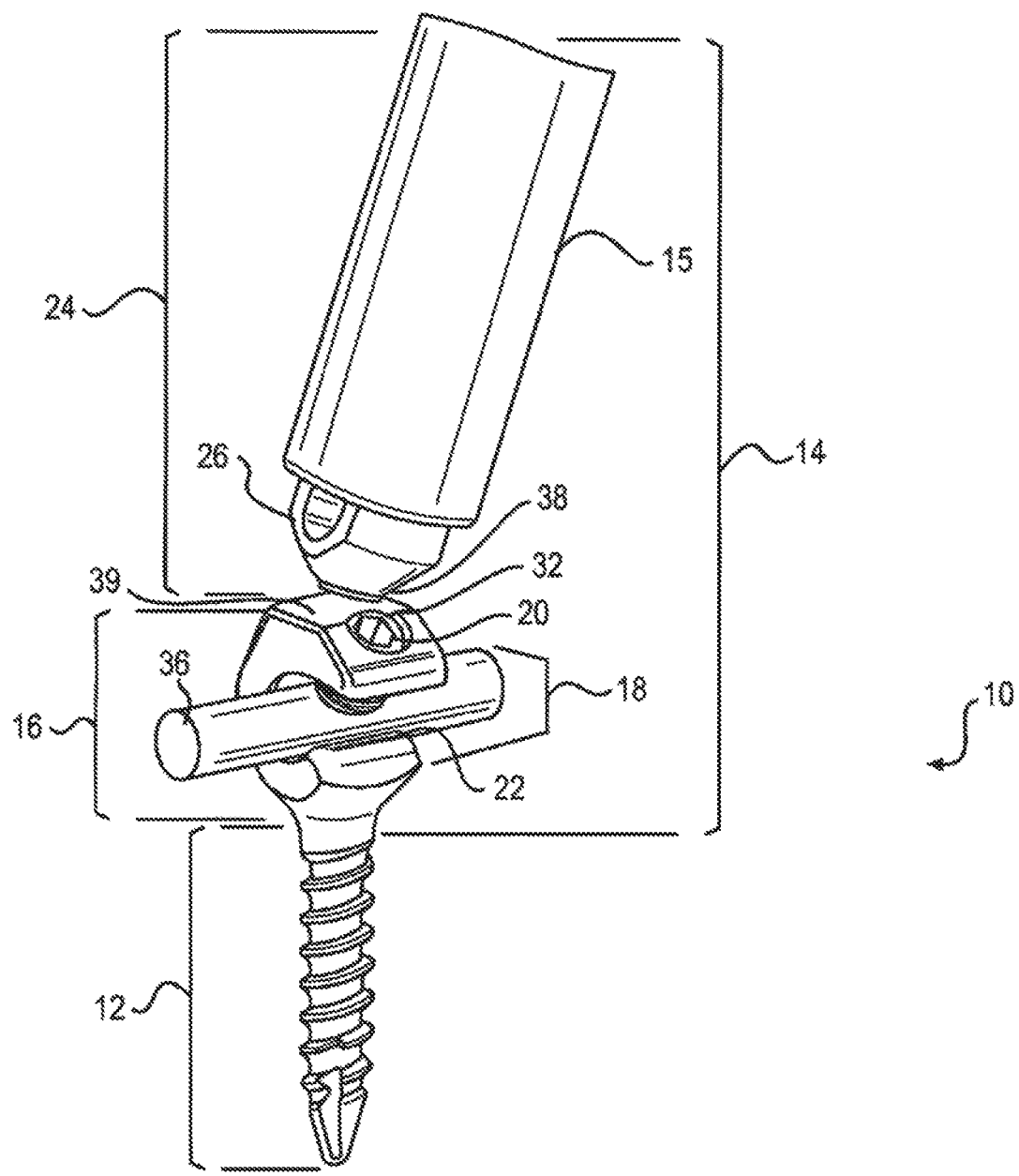
FIG. 57 shows an isometric view of one embodiment of the pedicle screw having a removable upper rod coupling showing temporary rod with the upper rod coupling removal tool.

FIG. 57 shows an isometric view of one embodiment of the pedicle screw having a removable upper rod coupling showing temporary rod with the upper rod coupling removal tool. The pedicle screw 10 includes a bone fastener 12 and a rod coupling head 14. The rod coupling head 14 includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36. The lower rod coupling 16 also includes a bore 20, through which a permanent rod fastener 22 can be inserted to fasten a permanent rod 36. As in the case of the lower rod opening 18, the material of the pedicle screw 10 surrounding the bore 20 will also be sufficiently strong to retain and affix a permanent rod 36. The upper rod coupling 24 has an upper rod opening 26. The upper rod coupling 24 is formed to permit the user to insert a temporary rod (not shown) using a temporary rod fastener (not shown). The lower coupling 16 and upper rod coupling 24 will often be made of unitary construction. For illustration purposes, and not necessarily as an element or limitation, a transition 32 is denoted. In unitary embodiments, the transition 32 provides for the breakage between the lower coupling 16 and the upper rod coupling 24 at breakpoint 38 for the total separation of the lower coupling 16 and the upper rod coupling 24. The upper rod coupling removal tool 15 is used by positioning it about the upper rod coupling 24 to break 39 at the transition 32 and at breakpoint 38 between the lower coupling 16 and the upper rod coupling 24. When made in a unitary construction, the pedicle screw 10 may be machined, sintered, cast, welded or glued as long as the pedicle screw is of sufficient strength for the bone fixation application.

Figure 58:
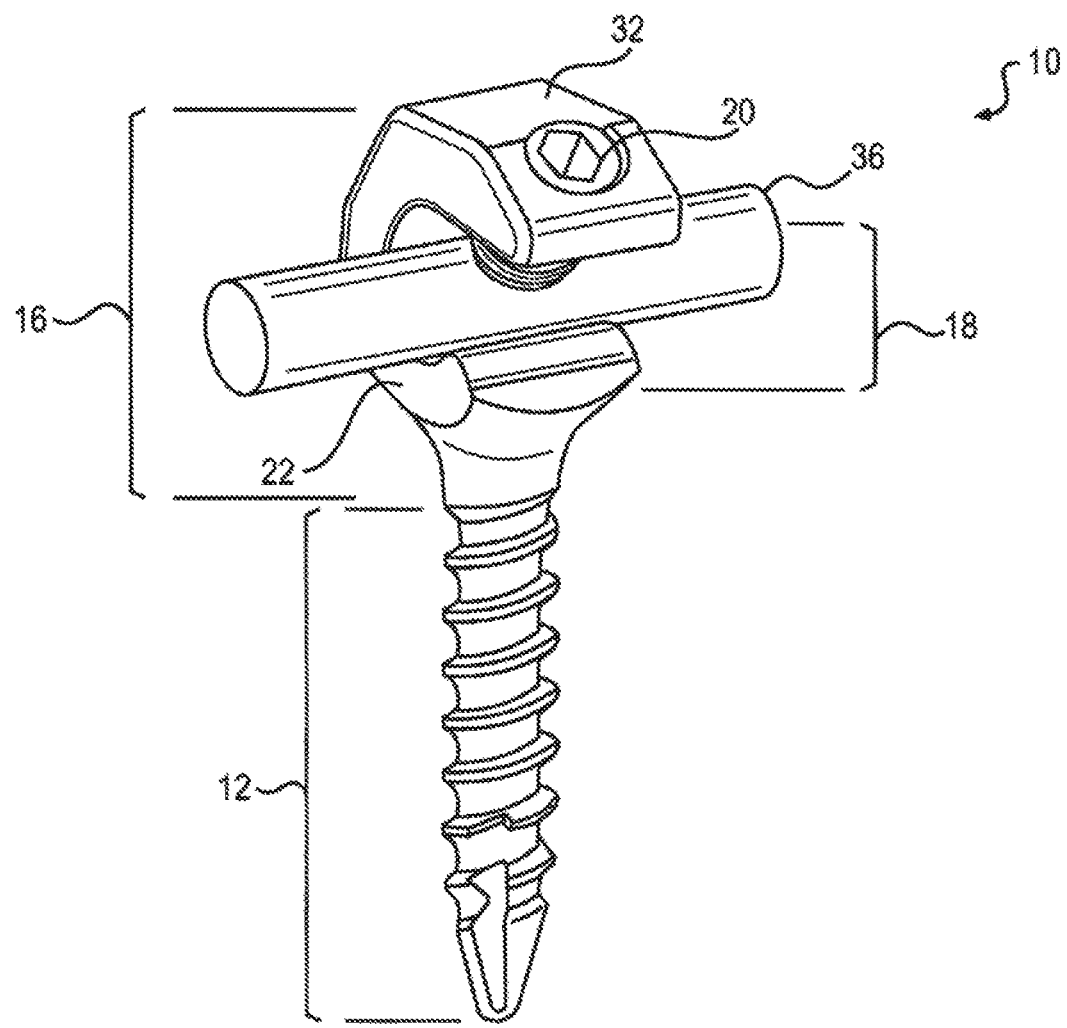
FIG. 58 shows an isometric view of one embodiment of the pedicle screw showing the permanent rod with the upper rod coupling removed.

FIG. 58 shows an isometric view of one embodiment of the pedicle screw showing the permanent rod with the upper rod coupling removed. The pedicle screw 10 includes a bone fastener 12 and a rod coupling head 14 (not shown). The rod coupling head 14 (not shown) includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36. The lower rod coupling 16 also includes a bore 20, through which a permanent rod fastener 22 can be inserted to fasten a permanent rod 36. As in the case of the lower rod opening 18, the material of the pedicle screw 10 surrounding the bore 20 will also be sufficiently strong to retain and affix a permanent rod 36. The upper rod coupling (not shown) has been removed. The transition 32 provides for the breakage between the lower coupling 16 and the upper rod coupling (not shown) for the total separation of the lower coupling 16 and the upper rod coupling (not shown). When made in a unitary construction, the pedicle screw 10 may be machined, sintered, cast, welded or glued as long as the pedicle screw is of sufficient strength for the bone fixation application.

Figure 59:
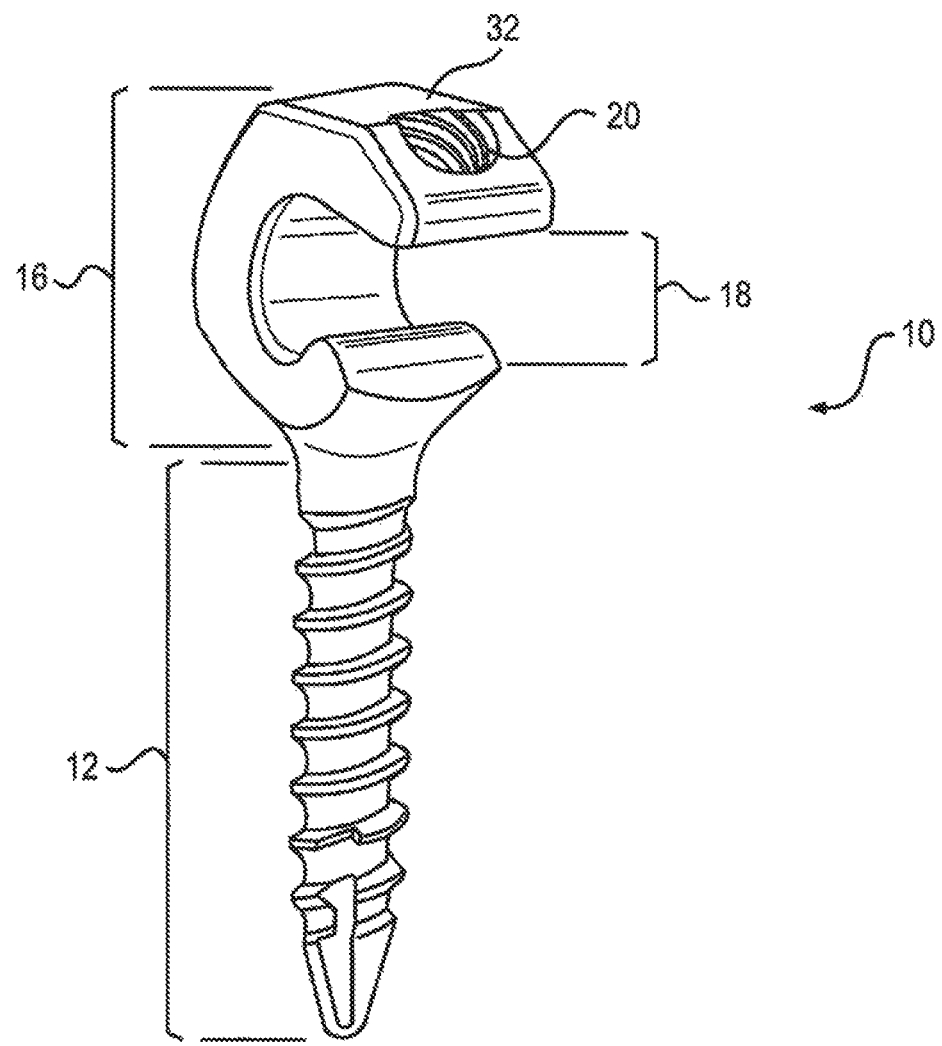
FIG. 59 shows an isometric view of one embodiment of the pedicle screw with the upper rod coupling removed.

FIG. 59 shows an isometric view of one embodiment of the pedicle screw with the upper rod coupling removed. The pedicle screw 10 includes a bone fastener 12 and a rod coupling head 14 (not shown). The rod coupling head 14 (not shown) includes a lower rod coupling 16 having a lower rod opening 18. The lower rod opening 18 may have any angle so long as the material of the pedicle screw 10 that surrounds the lower rod opening 18 is sufficiently strong to retain and affix a permanent rod 36 (not shown). The lower rod coupling 16 also includes a bore 20, through which a permanent rod fastener (not shown) can be inserted to fasten a permanent rod (not shown). As in the case of the lower rod opening 18, the material of the pedicle screw 10 surrounding the bore 20 will also be sufficiently strong to retain and affix a permanent rod (not shown). The upper rod coupling (not shown) has been removed. The transition 32 provides for the breakage between the lower coupling 16 and the upper rod coupling (not shown) for the total separation of the lower coupling 16 and the upper rod coupling (not shown). When made in a unitary construction, the pedicle screw 10 may be machined, sintered, cast, welded or glued as long as the pedicle screw is of sufficient strength for the bone fixation application.

The rod manipulators may be used in conjunction with existing spinal screw and rod fixation systems or may be used in conjunction with the pedicle screw. The size and thickness of rods may be varied depending on the type of surgery, tensile strength required and preference of the user.

The new rod link frame is strong enough and rigid enough that, in many cases, it can be used alone on one side of the spine to achieve and hold a correction while a permanent rod is inserted on the other side. This means that standard pedicle screws, configured to hold a single rod can be used and the device is adaptable to a broad range of spinal implant systems.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A system for spinal fixation comprising:
  a permanent rod;
  a temporary rod; and
  a bone screw comprising:
    a bone fastener portion;
    a permanent rod coupling comprising a lateral rod opening adapted to receive the permanent rod;
    a temporary rod coupling comprising a temporary rod channel adapted to receive the temporary rod, wherein the temporary rod coupling further comprises an upper rod fastener mated to an upper threaded opening, wherein the upper rod fastener is configured to engage the temporary rod positioned in the temporary rod channel; and a notched breakaway portion positioned between the permanent rod coupling and the temporary rod coupling and configured to allow breaking off of the temporary rod coupling from the permanent rod coupling, wherein the temporary rod coupling is disposed above the permanent rod coupling.

2. The system of claim 1, wherein the permanent rod coupling further comprises a permanent rod fastener mated to fit a threaded bore to extend into the lateral rod opening, wherein the permanent rod fastener is configured to engage the permanent rod positioned in the lateral rod opening, and wherein the permanent rod fastener, the upper rod fastener, or both are threaded.

3. The system of claim 2, wherein the lateral rod opening and the temporary rod channel are generally perpendicular.

4. The system of claim 2, wherein the temporary rod channel and the bone fastener portion are generally parallel.

5. The system of claim 2, wherein the lateral rod opening and the bone fastener portion are generally perpendicular.

6. The system of claim 1, wherein the bone fastener portion is permanently attached to the permanent rod coupling.

7. The system of claim 1, wherein the bone fastener portion is semi-permanently attached to the permanent rod coupling to allow the permanent rod coupling to be positioned at a variable angle relative to the bone fastener.

8. The system of claim 1, wherein the bone fastener portion includes a threaded portion configured to engage bone.

9. The system of claim 1, wherein the permanent rod is insertable into the lateral rod opening along a direction transverse to a longitudinal axis of the permanent rod and transverse to a longitudinal axis of the bone fastener portion.

10. A system for spinal fixation comprising:
a permanent rod;
a temporary rod; and
a bone screw comprising:
a bone fastener portion;
a permanent rod coupling adapted to receive the permanent rod;
a temporary rod coupling adapted to receive the temporary rod; and
a notched breakaway portion positioned between the permanent rod coupling and the temporary rod coupling and configured to allow breaking off of the temporary rod coupling from the permanent rod coupling, wherein the temporary rod coupling is initially disposed above the permanent rod coupling, and wherein the permanent rod is positioned in a lateral rod opening and the temporary rod is temporarily positioned in a temporary rod channel during a bone realignment, and wherein an upper threaded opening extends into the temporary rod channel, and an upper rod fastener is configured to mate to the upper threaded opening, wherein the upper rod fastener is configured to engage the temporary rod positioned in the temporary rod channel.

11. The system of claim 10, wherein the permanent rod coupling further comprises a permanent rod fastener and the permanent rod fastener, the upper rod fastener or both are threaded.

12. The system of claim 10, wherein the lateral rod opening and the temporary rod channel are generally perpendicular.

13. The system of claim 10, wherein the temporary rod channel and the bone fastener portion are generally parallel.

14. The system of claim 10, wherein the lateral rod opening and the bone fastener portion are generally perpendicular.

15. The system of claim 10, wherein the bone fastener portion is permanently attached to the permanent rod coupling.

16. The system of claim 10, wherein the bone fastener portion is semi-permanently attached to the permanent rod coupling to allow the permanent rod coupling to be positioned at a variable angle relative to the bone fastener.

17. The system of claim 10, wherein a threaded bore extends into the lateral rod opening, and a permanent rod fastener is configured to mate to fit the threaded bore to extend into the lateral rod opening, wherein the permanent rod fastener is configured to engage the permanent rod positioned in the lateral rod opening.

* * * * *